(12) United States Patent
Bono et al.

(10) Patent No.: US 9,120,819 B2
(45) Date of Patent: Sep. 1, 2015

(54) FGF-RECEPTOR AGONIST DIMERIC COMPOUNDS

(75) Inventors: Francoise Bono, Paris (FR); Nathalie Guillo, Paris (FR); Jean-Pierre Maffrand, Paris (FR); Pierre Fons, Paris (FR); Jacob-Alsboek Olsen, Frankfurt (DE); Gilles Anne-Archard, Paris (FR)

(73) Assignee: SANOFI, Paris (FR)

( * ) Notice: Subject to any disclaimer, the term of this patent is extended or adjusted under 35 U.S.C. 154(b) by 664 days.

(21) Appl. No.: 12/171,373

(22) Filed: Jul. 11, 2008

(65) Prior Publication Data

US 2009/0069368 A1 Mar. 12, 2009

Related U.S. Application Data

(63) Continuation of application No. PCT/FR2007/000051, filed on Jan. 12, 2007.

(30) Foreign Application Priority Data

Jan. 13, 2006 (FR) ..................................... 06 00317

(51) Int. Cl.
*C07D 519/00* (2006.01)
*C07D 209/02* (2006.01)
*A61K 31/435* (2006.01)
*C07D 221/02* (2006.01)
*A61K 47/48* (2006.01)

(52) U.S. Cl.
CPC ............ *C07D 519/00* (2013.01); *A61K 31/435* (2013.01); *A61K 47/481* (2013.01); *C07D 209/02* (2013.01); *C07D 221/02* (2013.01)

(58) Field of Classification Search
None
See application file for complete search history.

(56) References Cited

U.S. PATENT DOCUMENTS

| | | | |
|---|---|---|---|
| 4,400,387 A | 8/1983 | Rosseels et al. | |
| 7,442,708 B2 * | 10/2008 | Badorc et al. | 514/299 |
| 7,553,845 B2 * | 6/2009 | Alcouffe et al. | 514/299 |
| 2005/0203126 A1 | 9/2005 | Badorc | |
| 2006/0199962 A1 | 9/2006 | Badorc | |

FOREIGN PATENT DOCUMENTS

| WO | WO 03/084956 A1 | 10/2003 |
|---|---|---|
| WO | WO 2005/028476 A1 | 3/2005 |

OTHER PUBLICATIONS

Rotaru, et al., Synthesis of New Non-Symmetrical Substituted 7,7'-Bisindolizines by the Direct Reaction of 4,4'-Bipyridinium-Ylides with Dimeethyl Acetylenedicarboxylate, J. Hetero. Chem., 41,; 2004; pp. 893-897.
Seed, B., Making agonists of antagonists, Chem & Biology, Nov. 1994; 1: pp. 125-129.
International Search Report dated Jun. 19, 2007.

* cited by examiner

*Primary Examiner* — Jeffrey S Lundgren
*Assistant Examiner* — Meghan Finn
(74) *Attorney, Agent, or Firm* — Morrison & Foerster LLP

(57) ABSTRACT

FGF receptor agonist compounds corresponding to the general formula: M1-L-M2 are disclosed in which M1 and M2, which may be identical or different, each represent, independently of one another, a monomer unit M, and L represents a linker group, wherein the monomer unit is of the general formula I.

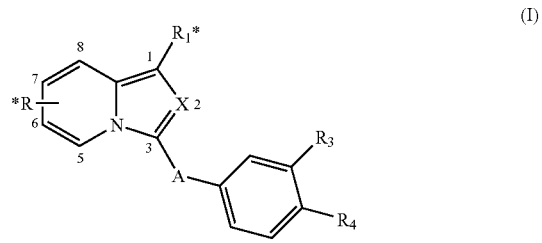

(I)

15 Claims, No Drawings

FGF-RECEPTOR AGONIST DIMERIC COMPOUNDS

The present invention relates to novel heterocyclic compounds that induce Fibroblast Growth Factor receptor (or FGFR) dimerization, to the process for the preparation thereof and to the therapeutic uses thereof. The present invention relates in particular to novel compounds with a dimeric structure, as FGFR agonists.

Angiogenesis is a process for generating new blood capillaries. When a blood vessel is obstructed, angiogenesis, associated with capillary dilation (arteriogenesis), improves the revascularization of the obstructed zone. It has been shown, in vitro and in vivo, that several growth factors (such as Fibroblast Growth Factors or FGFs) stimulate this process.

FGFs are a family of polypeptides synthesized by a large number of cells during embryonic development and by cells of adult tissues under various pathological conditions.

FGF2 (or b-FGF) is the first and the most well-characterized of these growth factors. FGF2 is an 18 kD protein which induces proliferation, migration and protease production by endothelial cells in culture and neovascularization in vivo. FGF2 interacts with endothelial cells by means of two classes of receptors, high-affinity receptor tyrosine kinases (FGFRs) and low-affinity heparan sulphate proteoglycan (HSPG) type receptors located at the cell surface and in extracellular matrices. Thus, FGF2 and its receptors represent very relevant targets for therapies aimed at activating or inhibiting angiogenic processes.

As a result, potent antagonists of the binding of FGFs to their receptor tyrosine kinases (FGFRs), such as indolizine derivatives, are described in international Patent Applications WO2003084956 and WO2005028476, and imidazo[1,5-a]pyridine derivatives in international Patent Application WO2006097625.

Moreover, it is known that cell surface receptor tyrosine kinases transmit information through the plasma membrane in particular by mechanisms of dimerization of the extracellular domains of these receptors. Known ligands capable of activating these dimerization mechanisms are typically natural compounds such as FGFs, PDGF (Platelet-Derived Growth Factor), VEGF (Vascular Endothelial Growth Factor), EPO (Erythropoietin), G-CSF (Granulocyte-Colony Stimulating Factor) or TPO (Thrombopoietin), cytokines or insulin.

Once dimerized, some of these receptors bring about a signal cascade which results, via cell proliferation and migration, in the formation of new vessels and therefore in an activation of angiogenesis.

B. Seed (*Chemistry and Biology*, November, 1994, 1, 125-129) puts forward the general principle that it would be possible to construct cell receptor agonists by dimerization of natural or slightly modified compounds having an antagonistic action with respect to these same cell receptors. These conceptual recommendations are not supported or illustrated by any specific molecule, in particular low-molecular-weight synthetic molecules. Articles such as S. A. Qureshi (PNAS, 1999, vol. 96, no. 21, 12156-12161), B. E. Welm (The Journal of Cell Biology, 2002, vol. 157, 4, 703-714), K. Koide (J. Am. Chem. Soc., 2001, 123, 398-408) describe nonpeptide compounds or chemical inducers of dimerization (CIDs), these compounds acting on chimeric receptors and not on endogenous receptors. They do not present any results showing that a CID makes it possible to activate the signalling pathway of an endogenous receptor.

Furthermore, Ariad (WO96/13613, WO97/31898 and WO97/31899) has developed Rapamycin derivative dimers which are capable of multimerizing chimeric FKBP (FK506 binding protein) proteins containing immunophilin derivative domains.

The Applicant has now found novel synthetic molecules capable of activating the formation of new blood vessels (or angiogenesis) by inducing FGF receptor dimerization.

The aim of the invention is to propose novel FGF receptor agonist compounds with a dimeric structure.

These compounds lead to a dimerization of FGF receptors which causes activation thereof and, in the end, activation of angiogenesis.

A subject of the present invention is FGF receptor agonist compounds corresponding to the formula:

$$M_1\text{-L-}M_2$$

in which $M_1$ and $M_2$, which may be identical or different, are each, independently of one another, a monomer unit M, and L is a linker group that links $M_1$ and $M_2$ covalently.

A subject of the present invention is FGF receptor agonist compounds as defined above, characterized in that said linker group L comprises from 1 to 25 links.

A subject of the present invention is FGF receptor agonist compounds as defined above, characterized in that said monomer unit corresponds to the formula M which follows:

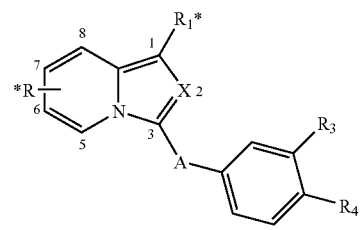

in which,

X is N or C—$R_2$*,

A is a —CO— or —SO$_2$— radical,

* indicates the linkage site of L with, firstly, the monomer unit $M_1$ and, secondly, with the monomer unit $M_2$; said linkage site of each monomer unit $M_1$ or $M_2$ being located on one of the substituents R, $R_1$ or $R_2$;

R is a hydrogen atom, a halogen atom, a linear or branched alkyl radical containing from 1 to 5 carbon atoms, a hydroxyl radical, or a radical of formula:

—CO$_2$R$_5$

—CO—NR$_6$R$_7$

—O-Alk

—O-Alk-CO$_2$R$_5$

—O-Alk-CO—NR$_6$R$_7$

—O-Alk-NR$_6$R$_7$

—O-Alk-Ph

—NR$_6$R$_7$

—NH—SO$_2$-Alk

—NH—CO-Alk, or

—NH—CO$_2$-Alk in which:

$R_5$ is a hydrogen atom, a linear or branched alkyl radical containing from 1 to 5 carbon atoms or a benzyl radical;

$R_6$ and $R_7$, which may be identical or different, are each a hydrogen atom, a linear or branched alkyl radical containing from 1 to 5 carbon atoms or a benzyl radical;

Alk is a linear or branched alkyl radical having from 1 to 5 carbon atoms or a linear or branched alkylene radical having from 1 to 5 carbon atoms;

Ph is a phenyl radical optionally substituted with one or more halogen atoms, with one or more hydroxyl radicals, with one or more linear or branched alkoxy radicals containing from 1 to 5 carbon atoms, or with one or more —$COOR_5$ radicals;

$R_1$ is a hydrogen atom, a halogen atom, a hydroxyl radical, a cyano radical, a linear or branched alkyl radical containing from 1 to 5 carbon atoms or a radical of formula:

—$CO_2R_5$

—CO—$NR_6R_7$

—CO—NH-Alk-$CO_2R_5$

—CO—NH-Ph

—O-Alk

—O-Alk-$CO_2R_5$

—O-Alk-CO—$NR_6R_7$

—O-Alk-$OR_5$

—O-Alk-Ph

—O-Ph

—$NR_6R_7$

—NH—$SO_2$-Alk

—NH—CO-Alk

—NH—CO-Alk-$CO_2R_5$

—NH—CO-Alk-CO—$NR_6R_7$

—NH—$CO_2$-Alk

—NH—CO-Ph, or an aryl or heteroaryl radical containing 5 or 6 atoms selected from C, N, O and S, optionally substituted with one or more halogen atoms, with one or more linear or branched alkyl radicals containing from 1 to 5 carbon atoms, with one or more linear or branched alkoxy radicals containing from 1 to 5 carbon atoms, or with one or more —$CO_2R_5$ or —CO—$NR_6R_7$ radicals in which Alk, Ph, $R_5$, $R_6$ and $R_7$ are as defined with respect to the group R;

$R_2$ is a linear or branched alkyl radical containing from 1 to 5 carbon atoms, a cycloalkyl radical containing from 3 to 6 carbon atoms or a phenyl radical optionally substituted with one or more halogen atoms, with one or more carboxyl radicals, with one or more linear or branched alkoxy radicals containing from 1 to 5 carbon atoms, with one or more hydroxyl radicals, with one or more benzyloxy radicals, or with one or more alkoxycarbonyl radicals containing from 2 to 6 carbon atoms;

$R_3$ and $R_4$ are, independently of one another, a hydrogen atom, a hydroxyl radical, an amino radical, a nitro radical or a radical of formula:

—$CO_2R_5$

—CO—$NR_6R_7$

—CO—NHOH

—O-Alk

—O-Alk-$NR_6R_7$

—O-Alk-CO—$NR_6R_7$

—NHOH

—$NR_6R_7$

—N($R_8$)—CO-Alk

—N($R_8$)—CO—$CF_3$

—N($R_8$)—CO-Ph

—N($R_8$)—$CO_2$-Alk

—N($R_8$)—$SO_2$-Alk

—N($R_8$)—CO-Alk-$NR_6R_7$

—N($R_8$)—$SO_2$-Alk-$NR_6R_7$, or

—NH-Alk-$R_6R_7$ in which $R_8$ is a hydrogen atom or an -Alk-$COOR_5$ radical, and Alk, $R_5$, $R_6$ and $R_7$ are as defined with respect to the group R;

or else $R_3$ and $R_4$ form, together with the carbon atoms of the phenyl ring to which they are attached, a six-membered ring containing a nitrogen atom and another heteroatom such as oxygen;

in the form of a base or an addition salt with an acid or with a base, and also in the form of a hydrate or of a solvate.

A subject of the present invention is particularly compounds as defined above, comprising the monomer unit of formula M in which A is a —CO— radical.

A subject of the present invention is particularly compounds as defined above, comprising the monomer unit of formula M in which:

X=C—$R_2$;

R on the 6-, 7- or 8-position of the indolizine is a hydrogen atom, a halogen atom, a hydroxyl radical or a radical of formula:

—$COOR_5$

—CO—$NR_6R_7$

—O-Alk

—O-Alk-$CO_2R_5$

—O-Alk-$NR_6R_7$

—$NR_6R_7$

—NH—$SO_2$-Alk

—NH—CO-Alk, or

—NH—$CO_2$-Alk in which:
- R$_5$ is a hydrogen atom, a linear or branched alkyl radical containing from 1 to 5 carbon atoms or a benzyl radical;
- R$_6$ and R$_7$, which may be identical or different, are each a hydrogen atom, a linear or branched alkyl radical containing from 1 to 5 carbon atoms or a benzyl radical,
- Alk is a linear or branched alkyl radical containing from 1 to 5 carbon atoms or a linear or branched alkylene radical containing from 1 to 5 carbon atoms;
- Ph is a phenyl radical optionally substituted with one or more halogen atoms, with one or more hydroxyl radicals, with one or more linear or branched alkoxy radicals containing from 1 to 5 carbon atoms, or with one or more —COOR$_5$ radicals;
- R$_1$ is a hydrogen atom, a halogen atom, a hydroxyl radical, a cyano radical or a radical of formula:

—CO$_2$R$_5$

—CO—NR$_6$R$_7$

—CO—NH-Alk-CO$_2$R$_5$

—CO—NH-Ph

—O-Alk

—O-Alk-CO$_2$R$_5$

—O-Alk-CO—NR$_6$R$_7$

—O-Alk-NR$_6$R$_7$

—O-Alk-OR$_5$

—O-Alk-Ph

—NR$_6$R$_7$

—NH—SO$_2$-Alk

—NH—CO-Alk

—NH—CO-Alk-CO$_2$R$_5$

—NH—CO-Alk-CO—NR$_6$R$_7$

—NH—CO$_2$-Alk

—NH—CO-Ph, or an aryl or heteroaryl radical containing 5 or 6 atoms selected from C, N, O and S, optionally substituted with one or more halogen atoms, with one or more linear or branched alkyl radicals containing from 1 to 5 carbon atoms, with one or more linear or branched alkoxy radicals containing from 1 to 5 carbon atoms, or with one or more —CO$_2$R$_5$ or —CO—NR$_6$R$_7$ radicals in which Alk, Ph, R$_5$, R$_6$ and R$_7$ are as defined with respect to the group R;
- R$_2$ is a linear or branched alkyl radical containing from 1 to 5 carbon atoms, a cycloalkyl radical containing from 3 to 6 carbon atoms or a phenyl radical optionally substituted with one or more halogen atoms, with one or more alkoxy radicals containing from 1 to 5 carbon atoms, with one or more carboxyl radicals or with one or more alkoxycarbonyl radicals containing from 2 to 6 carbon atoms;
- R$_3$ and R$_4$, which may be identical or different are each a hydrogen atom, a hydroxyl radical, an alkoxy radical containing from 1 to 5 carbon atoms, an amino radical, a nitro radical, or a radical of formula:

—NR$_6$R$_7$

—NH—CO-Alk

—NH—SO$_2$-Alk

—CO$_2$R$_5$

—CO—NR$_6$R$_7$, or

—CO—NHOH in which Alk, Ph, R$_5$, R$_6$ and R$_7$ are as defined with respect to the group R.

A subject of the present invention is more particularly compounds as defined above, comprising the monomer unit of formula M in which:

X=C—R$_2$;

R on the 6-, 7- or 8-position of the indolizine is a hydrogen atom, a hydroxyl radical, a carboxyl radical or a radical of formula:

—O-Alk

—O-Alk-CO$_2$R$_5$

—O-Alk-CO—NR$_6$R$_7$

—O-Alk-NR$_6$R$_7$

—O-Alk-Ph

—NR$_6$R$_7$

—NH—SO$_2$-Alk, or

—NH—CO-Alk in which:
- R$_5$ is a hydrogen atom, an alkyl radical containing from 1 to 5 carbon atoms or a benzyl radical;
- R$_6$ and R$_7$, which may be identical or different, are each a hydrogen atom, a linear or branched alkyl radical containing from 1 to 5 carbon atoms or a benzyl radical;
- Alk is a linear or branched alkyl radical or alkylene radical containing from 1 to 5 carbon atoms;
- Ph is a phenyl radical optionally substituted with one or more halogen atoms, with one or more hydroxyl radicals, with one or more alkoxy radicals containing from 1 to 5 carbon atoms, or with one or more —COOR$_5$ radicals;
- R$_1$ is a halogen atom, a hydroxyl radical, a carboxyl radical or a radical of formula:

—O-Alk

—O-Alk-CO$_2$R$_5$

—O-Alk-Ph

—O-Ph

—NR$_6$R$_7$

—NH—CO-Ph, or an aryl or heteroaryl radical containing 5 or 6 atoms selected from C, N, O and S, optionally substituted with one or more halogen atoms, with one or more linear or branched alkyl radicals containing from 1 to 5 carbon atoms, with one or more linear or branched alkoxy radicals containing from 1 to 5 carbon atoms, or with one or more —$CO_2R_5$ or —CO—$NR_6R_7$ radicals in which Alk, Ph, $R_5$, $R_6$ and $R_7$ are as defined with respect to the group R;

$R_2$ is an alkyl radical containing from 1 to 5 carbon atoms or a cycloalkyl radical containing from 3 to 6 carbon atoms;

$R_3$ and $R_4$, which may be identical or different, are each a linear or branched alkoxy radical containing from 1 to 5 carbon atoms, an amino radical, a carboxyl radical, a hydroxyl radical, a radical of formula CO—$NR_6R_7$, or a radical of formula —NH—$SO_2$-Alk, in which Alk, $R_6$ and $R_7$ are as defined with respect to the group R.

A subject of the present invention is more particularly compounds as defined above, comprising the monomer unit of formula M in which:

X=C—$R_2$;

R on the 6- or 8-position of the indolizine is a hydrogen atom or a hydroxyl radical;

$R_1$ is a hydroxyl radical, or a radical of formula:

—O-Alk

—O-Alk-Ph

—$NR_6R_7$, or

—NH—CO-Ph in which Alk, Ph, $R_6$ and $R_7$ are as defined above;

$R_2$ is an alkyl radical containing from 1 to 5 carbon atoms;

$R_3$ is a linear or branched alkoxy radical containing from 1 to 5 carbon atoms or a carboxyl radical;

$R_4$ is an amino radical.

A subject of the present invention is particularly compounds as defined above, comprising the monomer unit of formula M in which:

X=N;

R on the 5-, 6-, 7- or 8-position of the imidazo[1,5-a] pyridine is a hydrogen atom, a halogen atom, a linear or branched alkyl radical containing from 1 to 5 carbon atoms, a hydroxyl radical or a radical of formula:

—$CO_2R_5$

—CO—$NR_6R_7$

—O-Alk

—O-Alk-$CO_2R_5$

—O-Alk-CO—$NR_6R_7$

—O-Alk-$NR_6R_7$

—O-Alk-Ph

—$NR_6R_7$

—NH—$SO_2$-Alk

—NH—CO-Alk, or

—NH—$CO_2$-Alk in which:

$R_5$ is a hydrogen atom, a linear or branched alkyl radical containing from 1 to 5 carbon atoms or a benzyl radical;

$R_6$ and $R_7$, which may be identical or different, are each a hydrogen atom, a linear or branched alkyl radical containing from 1 to 5 carbon atoms or a benzyl radical;

Alk is a linear or branched alkyl radical containing from 1 to 5 carbon atoms or a linear or branched alkylene radical containing from 1 to 5 carbon atoms;

Ph is a phenyl radical optionally substituted with one or more halogen atoms, with one or more hydroxyl radicals, with one or more linear or branched alkoxy radicals containing from 1 to 5 carbon atoms, or with one or more —$COOR_5$ radicals;

—$R_1$ is a hydrogen atom, a halogen atom, a cyano radical or a radical of formula:

—$CO_2R_5$

—CO—NH-Ph

—$NR_6R_7$

—NH—$SO_2$-Alk

—NH—CO-Alk

—NH—$CO_2$-Alk

—NH—CO-Ph, or an aryl or heteroaryl radical containing 5 or 6 atoms selected from C, N, O and S, optionally substituted with one or more halogen atoms, with one or more linear or branched alkyl radicals containing from 1 to 5 carbon atoms, with one or more linear or branched alkoxy radicals containing from 1 to 5 carbon atoms, or with one or more —$CO_2R_5$ or —CO—$NR_6R_7$ radicals, in which Alk, Ph, $R_5$, $R_6$ and $R_7$ are as defined with respect to the group R;

$R_3$ and $R_4$, which may be identical or different, are each a hydrogen atom, a hydroxyl radical, a linear or branched alkoxy radical containing from 1 to 5 carbon atoms, an amino radical, a nitro radical, or a radical of formula:

—$NR_6R_7$

—NH—CO-Alk

—NH—$SO_2$-Alk

—$CO_2R_5$

—CO—$NR_6R_7$, or

—CO—NHOH in which Alk, Ph, R5, R6 and R7 are as defined with respect to the group R;

or R3 and R4 form, together with the carbon atoms of the phenyl ring to which they are attached, a 6-membered carbon-based ring containing a nitrogen atom and another heteroatom such as oxygen.

A subject of the present invention is more particularly compounds as defined above, comprising the monomer unit of formula M in which:

X=N;

R on the 6-, 7- or 8-position of the imidazo[1,5-a]pyridine is a hydrogen atom, a halogen atom, a hydroxyl radical, a carboxyl radical or a radical of formula:

—CO—$NR_6R_7$

—O-Alk

—O-Alk-$CO_2R_5$

—O-Alk-Ph

—$NR_6R_7$

—NH—$SO_2$-Alk, or

—NH—CO-Alk in which:
$R_5$ is a hydrogen atom, a linear or branched alkyl radical containing from 1 to 5 carbon atoms or a benzyl radical;
$R_6$ and $R_7$, which may be identical or different, are each a hydrogen atom, a linear or branched alkyl radical containing from 1 to 5 carbon atoms or a benzyl radical;
Alk is a linear or branched alkyl radical containing from 1 to 5 carbon atoms or a linear or branched alkylene radical containing from 1 to 5 carbon atoms;
Ph is a phenyl radical optionally substituted with one or more halogen atoms, with one or more hydroxyl radicals, with one or more linear or branched alkoxy radicals containing from 1 to 5 carbon atoms, or with one or more —$COOR_5$ radicals;
$R_1$ is a hydrogen atom, a halogen atom, a carboxy radical or a radical of formula:

—$NR_6R_7$

—NH—$SO_2$-Alk

—NH—CO-Alk

—NH—CO-Ph, or an aryl or heteroaryl radical containing 5 or 6 atoms selected from C, N, O and S, optionally substituted with one or more halogen atoms, with one or more linear or branched alkyl radicals containing from 1 to 5 carbon atoms, with one or more linear or branched alkoxy radicals containing from 1 to 5 carbon atoms, or with one or more —$CO_2R_5$ or —CO—$NR_6R_7$ radicals,
in which Alk, Ph, $R_5$, $R_6$ and $R_7$ are as defined with respect to the group R;
$R_3$ and $R_4$, which may be identical or different, are each a linear or branched alkoxy radical containing from 1 to 5 carbon atoms, an amino radical, a carboxyl radical, a hydroxyl radical, or a radical of formula CO—$NR_6R_7$ or —NH—$SO_2$-Alk.

A subject of the present invention is more particularly compounds as defined above, comprising the monomer unit of formula M in which:

X=N,

R on the 8-position of the imidazo[1,5-a]pyridine is a hydrogen atom, a hydroxyl radical or a carboxyl radical,
$R_1$ is a hydrogen atom, a radical of formula —NH—CO-Ph, or an aryl or heteroaryl radical containing 5 or 6 atoms selected from C, N, O and S, optionally substituted with one or more —$CO_2R_5$ radicals,
in which Alk, Ph and $R_5$ are as defined above, $R_3$ is a linear or branched alkoxy radical containing from 1 to 5 carbon atoms or a carboxyl radical,
$R_4$ is an amino radical.

In the context of the present invention:
a "halogen atom" is intended to mean: a fluorine, a chlorine, a bromine or an iodine;
a "heteroatom" is intended to mean: a nitrogen, oxygen or sulphur atom;
a "linear or branched alkyl group" is intended to mean: a linear or branched, saturated aliphatic group. By way of examples, mention may be made of methyl, ethyl, propyl, isopropyl, butyl, isobutyl, methylcyclopropyl, pentyl, 2,2-dimethylpropyl, sec-butyl and tert-butyl groups;
a "linear or branched alkylene group" is intended to mean: an alkyl group as above, which is divalent, saturated, and linear or branched. By way of example, mention may be made of methylene, ethylene and propylene radicals;
a "linear or branched alkelyne group" is intended to mean: a linear or branched aliphatic group containing one or more ethylenic unsaturations;
a "linear or branched alkynyl group" is intended to mean: a linear or branched aliphatic group containing one or more acetylenic unsaturations;
a "linear or branched alkoxy group" is intended to mean: an —O-alkyl group, where the alkyl group is as defined above;
a "ring" or a "cycloalkyl group" is intended to mean: a cyclic alkyl group containing from 3 to 6 carbon atoms, and all the carbon atoms of which are involved in the ring. Mention may, for example, be made of cyclopropyl, cyclobutyl, cyclopentyl and cyclohexyl groups;
a "polycycle" is intended to mean: a group comprising two or more cycloalkyl groups as defined above;
a "heterocycle" is intended to mean: a cycloalkyl group as defined above and comprising one or more heteroatoms such as O, N and/or S;
an "aryl group" is intended to mean: a monocyclic aromatic group, for example a phenyl group;
a "heteroaryl group" is intended to mean: a cyclic aromatic group comprising 5 or 6 atoms and comprising one or more heteroatoms as defined above. By way of example of heteroaryl groups, mention may be made of a thienyl, furyl, pyrrolyl, imidazolyl or pyridinyl.

The Agonist Dimers

The agonists of formula $M_1$-L-$M_2$ according to the invention comprise two monomer units of formula M, called $M_1$ and $M_2$, which may be identical or different, each selected as having an FGFR antagonist activity.

The compounds of formula $M_1$-L-$M_2$ can exist in the form of bases or salified with pharmaceutically acceptable acids or bases. Such addition salts are also part of the invention.

The compounds according to the invention can also exist in the form of hydrates or solvates, i.e. in the form of associations or of combinations with one or more molecules or water or with a solvent. Such hydrates and solvates are also part of the invention.

The Linker Group

L is a linker group that links $M_1$ and $M_2$ covalently such that the distance between the two monomers $M_1$ and $M_2$ allows the dimerization of two FGF receptors. Said linker group preferably comprises from 1 to 25 links. Said linker group L more particularly comprises from 8 to 20 links. The term "links" is intended to mean only the bonds between atoms that make it possible to connect the monomer units $M_1$ and $M_2$.

The linker group L is characterized by a flexibility that allows each monomer unit of the compound of formula $M_1$-L-

M₂ to establish contact with the extracellular binding sites of the FGFR transmembrane receptors.

L is attached, firstly, to a monomer unit of formula M₁ by an atom placed on any one of the substituents R, R₁ or R₂ and attached, secondly, to the other monomer unit of formula M₂ by an atom placed on any one of the substituents R, R₁ or R₂, with M₁ and M₂ being identical or different.

A subject of the present invention is more particularly compounds as defined above, characterized in that:

L connects the 2 monomer units M₁ and M₂ by the radical R₁ or;

L connects the 2 monomer units M₁ and M₂ by the radical R₂ or;

L connects the 2 monomer units M₁ and M₂ by the radical R in its 8-position or;

L connects the 2 monomer units M₁ and M₂ by the radical R in its 7-position or;

L connects the 2 monomer units M₁ and M₂ by the radical R in its 6-position or;

L connects the 2 monomer units M₁ and M₂, firstly, by the radical R in its 8-position and, secondly, by the radical R in its 7- or 6-position, or;

L connects the 2 monomer units M₁ and M₂, firstly, by the radical R in its 7-position and, secondly, by the radical R in its 6-position, or;

L connects the 2 monomer units M₁ and M₂, firstly, by the radical R₂ and, secondly, by the radical R₁, or;

L connects the 2 monomer units M₁ and M₂, firstly, by the radical R₁ and, secondly, by the radical R in its 8-position.

The connecting atoms that are located on any one of the substituents R, R₁ and R₂ of the monomer unit of formula M may be O, N, C or S atoms.

The junctions between L and the monomer units may be C—O, C—N, C—C or C—S bonds. These bonds can be selected from functional groups such as esters, amides, ethers, carbamates, ureas, sulphonamides, thioethers, sulphones and thioureas, or else via alkyl-alkyl, alkyl-aryl or aryl-aryl C—C bonds.

The linker groups L suitable for the invention can be selected from structures of the type of aliphatic radicals that may be linear or branched and optionally interrupted with one or more heteroatoms such as O, N and/or S, one or more rings, one or more polycycles, one or more heterocycles (such as piperazine), or one or more aryls (such as phenyl) or heteroaryls (such as pyridine).

The linker groups L can optionally comprise one or more functions such as amide, urea, thiourea, carbamate, carbonate, sulphonamide, thiocarbamate, ester, thioester, ketone, N-sulphamate, guanidine, sulphone and/or sulphoxide.

The branches in the linker group L can themselves comprise aliphatic radicals that may be linear or branched and optionally interrupted with one or more heteroatoms such as O, N and/or S, one or more rings, one or more polycycles, one or more heterocycles, or one or more aryls or heteroaryls, and/or optionally one or more functions such as amide, urea, thiourea, carbamate, sulphonamide, thiocarbamate, ester, thioester, ketone, hydroxyl, O-sulphate, N-sulphamate, guanidine, sulphone and/or sulphoxide.

The linker groups L may be more particularly selected from the following radicals:

a linear or branched alkylene radical containing from 2 to 25 carbon atoms, a linear or branched alkenyl group containing from 2 to 25 carbon atoms, or a linear or branched alkynyl group containing from 2 to 25 carbon atoms;

or a radical selected from the formulae:

(A)

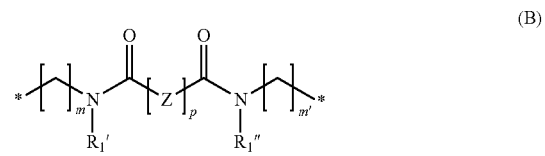
(B)

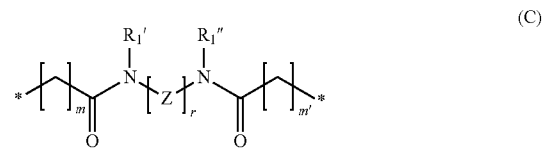
(C)

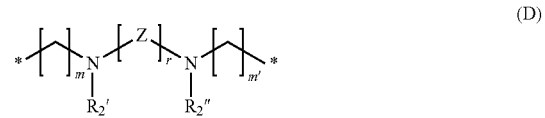
(D)

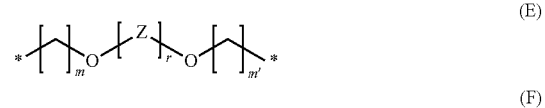
(E)

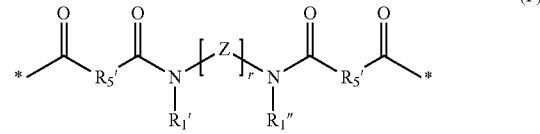
(F)

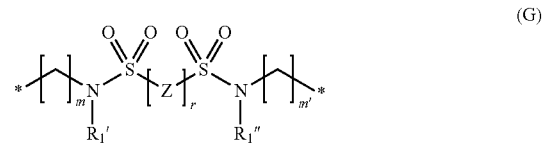
(G)

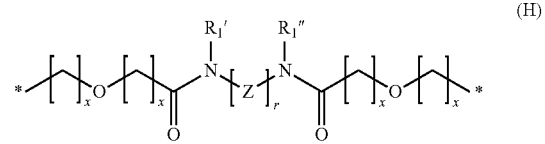
(H)

in which
* indicates the atom for connection of L with the monomer unit M on one of the substituents R, R₁ or R₂;

Z is a bond or a carbonyl radical or a linear, branched or cyclic, saturated, unsaturated or partially unsaturated alkylene radical containing from 1 to 6 carbon atoms that is optionally substituted with 1 or 2 carbonyl radicals, or else a radical —[CH₂]ₛ—[—CH—(CH₂)_q—OR₃']—[CH₂]ₛ—
—[CH₂]ₛ—[—CH—(CH₂)_q—NR₃'R₄']—[CH₂]ₛ—
—[CH₂—CH₂—O]_t—CH₂—CH₂— phenyl or alkylphenylalkyl, the phenyl group being optionally substituted with one or more alkoxy radicals containing from 1 to 5 carbon atoms, or heteroaryl or alkylheteroarylalkyl, the heteroaryl group being optionally substituted with one or more alkoxy radicals containing from 1 to 5 carbon atoms, n is an integer from 1 to 7,
m and m' are identical or different and are an integer from 0 to 8,
p is an integer from 0 to 11,
r is an integer from 1 to 11,
q is an integer from 0 to 5, s is an integer from 0 to 5,
t is an integer from 0 to 5,
x is an integer from 1 to 5,
m, m', n, p, r, s, t and x being such that the number of links of the linker group L does not exceed 25,
$R_1'$ and $R_1''$, which may be identical or different, are a hydrogen atom, or a linear or branched alkyl radical containing from 1 to 5 carbon atoms,
$R_2'$ and $R_2''$, which may be identical or different, are a hydrogen atom, a linear or branched alkyl radical containing from 1 to 5 carbon atoms, a benzyl radical or a sulphate group,
it being possible for $R_1'$ and $R_1''$ and also $R_2'$ and $R_2''$ to be optionally linked so as to form a ring, $R_3'$ and $R_4'$, which may be identical or different, are each a hydrogen atom, a linear or branched alkyl radical containing from 1 to 5 carbon atoms, a benzyl radical or a sulphate group,
R' is a linear or branched alkyl radical containing from 1 to 5 carbon atoms.

The Monomer Units

The monomer units of formula M as defined above are FGF receptor ligands that have an antagonist activity with respect to FGF2.

For the preparation of the monomers of formula M in which A is —CO— or —SO$_2$—, reference will be made to WO2003084956 and WO2005028476 when X is C—R$_2$, and to WO2006097625 when X is N.

The synthesis of the dimers is carried out by dimerization of monomeric compounds of formula M, M being an antagonist compound that itself has a free connecting atom, or an antagonist compound in which one of the possible connecting atoms is freed either by a chemical reaction based on the antagonist itself, or because it is a synthesis intermediate of the antagonist compound.

The present invention also relates to a process for preparing the dimers of formula M$_1$-L-M$_2$, comprising the reaction of at least one reactant of a monomer unit of formula M-W with a reactant of formula U-L-U', where M and L have the same meaning as above, it being possible for U and U' to be identical or different, W being located on one of the substituents R, R$_1$ or R$_2$ as defined above, W and U and also W and U' are each a functional group capable of reacting with one another so as to form a covalent bond of C—C, C—O, C—N, C—C or C—S type. These bonds can be selected from functional groups such as esters, amides, ethers, carbamates, ureas, sulphonamides, thioethers, sulphones and thioureas or else via alkyl-alkyl, alkyl-aryl or aryl-aryl C—C bonds.

W, U and U' may, for example, be an amino, hydroxyl, carboxyl, chloroformate, isocyanate, thiol, thioisocyanate, amido, carbamate, halogen, sulphonyl chloride, acid chloride, acid fluoride, alkene or alkyne group or an organometallic reactant such as a boronic ester or a boronic acid.

The reactants U-L-U' described above are commercially available or can be prepared by methods described in the literature or by methods selected from those known to those skilled in the art. The preparations of the reactants U-L-U' used in the preparation of the dimers of the present invention are mentioned or described in the experimental section (Examples R1 to R66).

The reactants U-L-U' that can be used in the present invention are alkylating agents known to those skilled in the art, such as dihalogenated derivatives, acylating agents such as activated dicarboxylic acids in the presence of a coupling agent, acid dichlorides, acid difluorides, dichloroformates, diisocyanates, dithioisocyanates, organometallic reactants such as boronic diesters or diboronic acids, or sulphonylating agents such as sulphonyl dichlorides. Said coupling agents may in particular be coupling agents of phosphonium type, such as (benzotriazol-1-yloxy)tripyrrolidinophosphonium hexafluorophosphate (PyBOP), benzotriazol-1-yloxytris (dimethylamino)phosphonium hexafluorophosphate (BOP) or O-benzotriazol-1-yl-N,N,N',N'-tetramethyluronium tetrafluoroborate (TBTU), or coupling agents of carbodiimide type, such as 1-(3-dimethylaminopropyl)-3-ethylcarbodiimide hydrochloride (EDCI).

For example, the dicarboxylic acids are prepared from a carboxylic acid, m being as defined above, such as {4-[(benzyloxy)carbonyl]phenoxy}acetic acid (described in Patent Application WO2001060813) or [3-(ethoxycarbonyl)phenoxy]acetic acid (A. Banerjee, M. M. Adak, S. Das, S. Banerjee, S. Sengupta, Indian Chem. Soc., 1987, 64, 1, 34-37), which is activated in the form of an acid chloride or with a coupling agent such as BOP in the presence of a weak base such as triethylamine, then which is reacted with a diamine $R_1'$, $R_1''$ Z and r being as defined above. The target dicarboxylic acids are obtained after saponification.

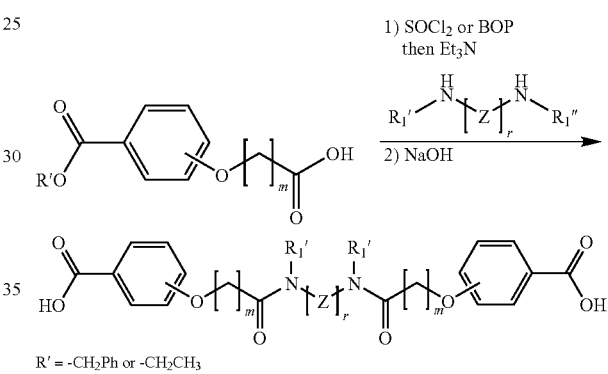

The dicarboxylic acids are also obtained by reaction of a diamine, with $R_1'$ and m being as defined above, such as ethyl 3-(2-aminoethoxy)benzoate, with either a dicarboxylic acid with Z and p being as defined above, in the presence of a coupling agent such as BOP or EDCI and of a weak base such as triethylamine, or with a sulphonyl dichloride with Z and r being as defined above, in the presence of a base such as triethylamine. The target dicarboxylic acids are obtained after saponification.

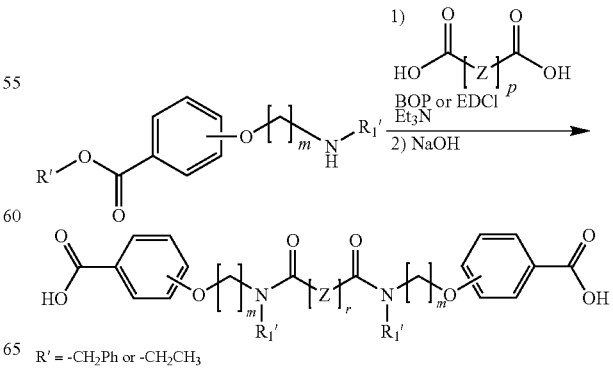

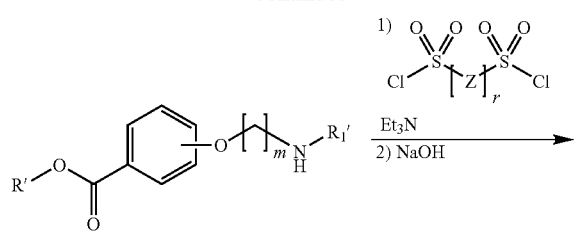

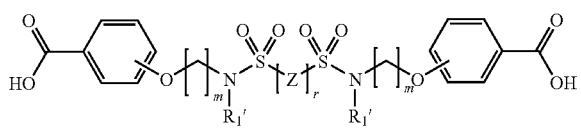

The dicarboxylic acids are also obtained by alkylation of an amine with $R_2'$, $R_2''$, Z and r being as defined above, with a halogenated derivative with m being as defined above, such as ethyl 3-(2-iodoethoxy)benzoate or ethyl 4-(2-iodoethoxy)benzoate [CAS 56703-36-7] in the presence of a base such as potassium carbonate. The target dicarboxylic acids are obtained after saponification.

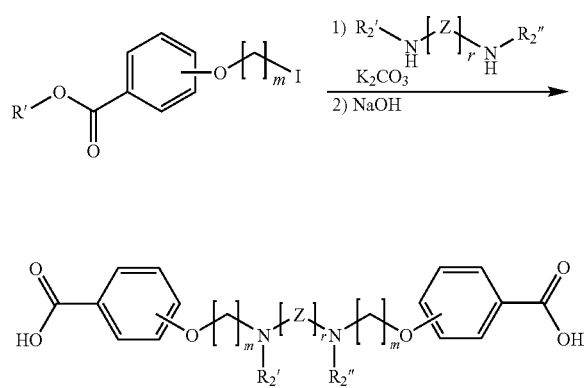

R' = -CH$_2$CH$_3$

The dicarboxylic acids are also obtained by reaction of a diamine with $R_1'$, $R_1''$, Z and r being as defined above, on an anhydride with $R_5'$ and x being as defined above, according to the protocol described in R. E. Asay et al., *J. Heterocyclic Chem.*, 1977, 14(1), 85-90).

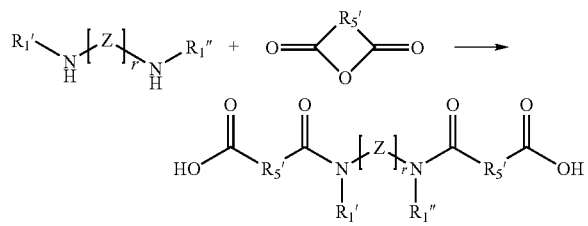

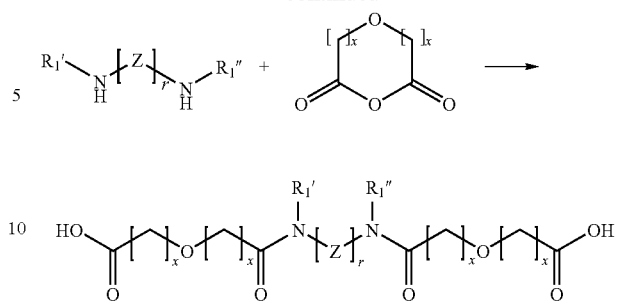

By adjusting the stoichiometry of the reactants, it is also possible to prepare the dicarboxylic acids as above with a linker of formula (B), (C), (D), (G) in which m and m' are different.

The boronic diesters used in the dimerization reactions via Suzuki coupling (*Synth. Commun.*, 1891, 11, 513) are obtained by alkylation of a hydroxyl derivative such as 3-(4,4,5,5-tetramethyl-1,3,2-dioxaborolan-2-yl)phenol or 4-(4,4,5,5-tetramethyl-1,3,2-dioxaborolan-2-yl)phenol with a dihalogenated derivative in the presence of a base such as potassium carbonate.

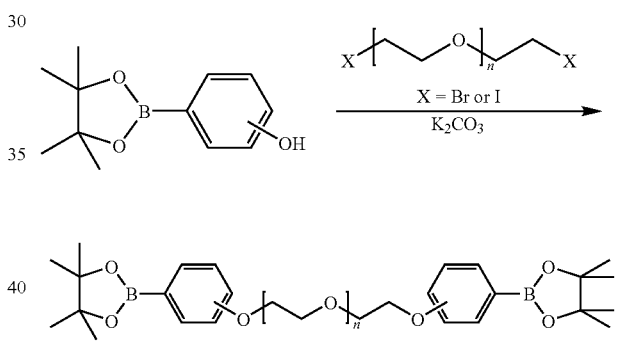

The monomers M can be dimerized to give:
 homodimers in the case where $M_1$ and $M_2$ are identical, as are their atoms for connection with the linker group L;
 heterodimers in the case where $M_1$ and $M_2$ are identical and their atoms for connection with the linker group L are different, and also in the case where $M_1$ and $M_2$ are different.

The monomers M can be dimerized to give homodimers or heterodimers of formula $M_1$-L-$M_2$ via different synthetic pathways as illustrated in the schemes which follow.

The methods and schemes described below apply to and can be generalized for the compounds M-W with A, X, R, $R_1$, $R_2$, $R_3$ and $R_4$ as defined above and the linker group L as defined above, unless otherwise mentioned.

Method I). When it is desired to dimerize a monomer M-W, in which R or $R_1$ is or has an amino function W, such a monomer M-W can be used to carry out an acylation using a diacylating agent such as an activated dicarboxylic acid in the presence of a suitable coupling agent such as BOP or PyBOP, or an acid dichloride or an acid difluoride, and a weak base such as triethylamine or pyridine.

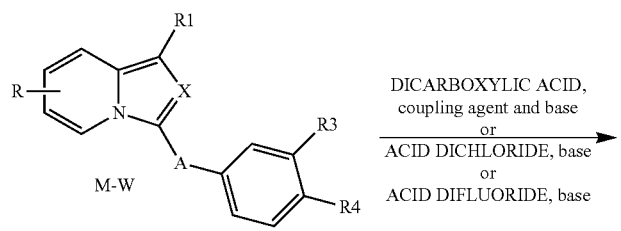
R or $R_1$ or $R_2$ has/is an -$NH_2$ group
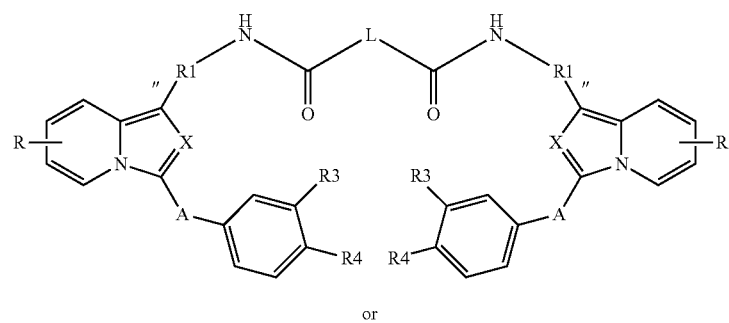
or
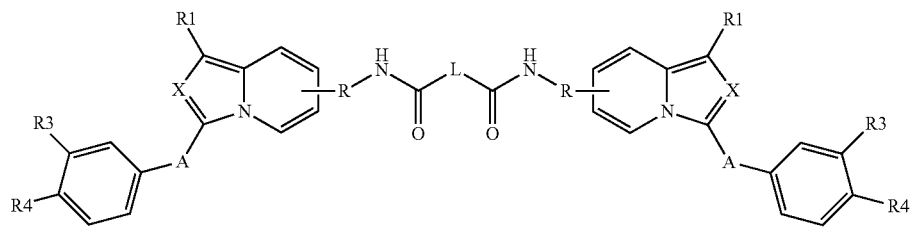
Illustrations of the case where $R_1$=$NH_2$:
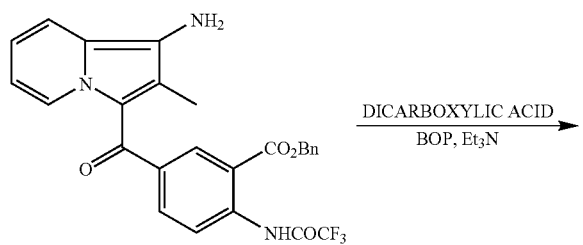
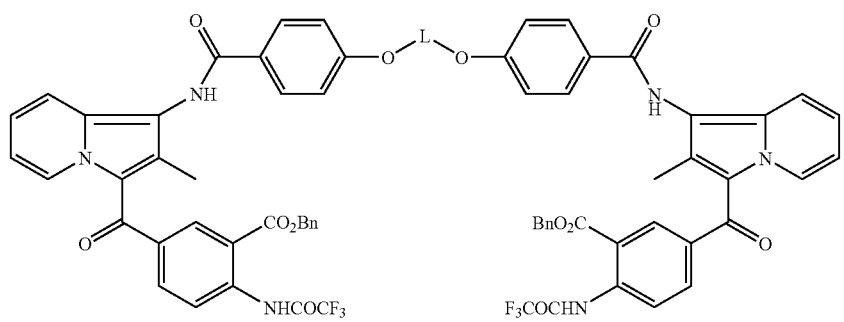

-continued
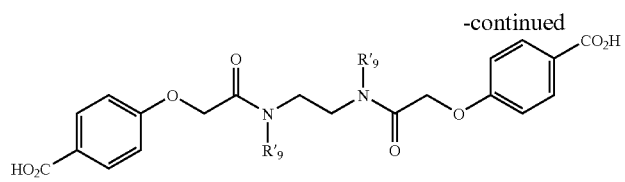
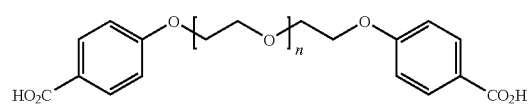
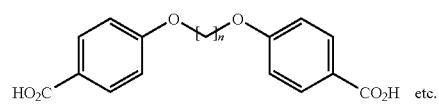 etc.
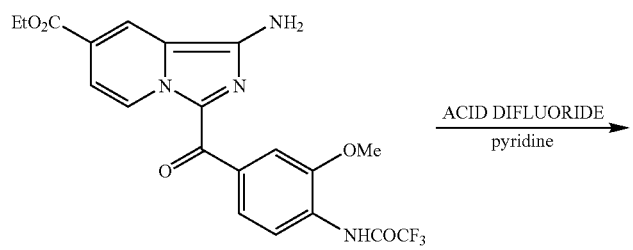 →[ACID DIFLUORIDE / pyridine]
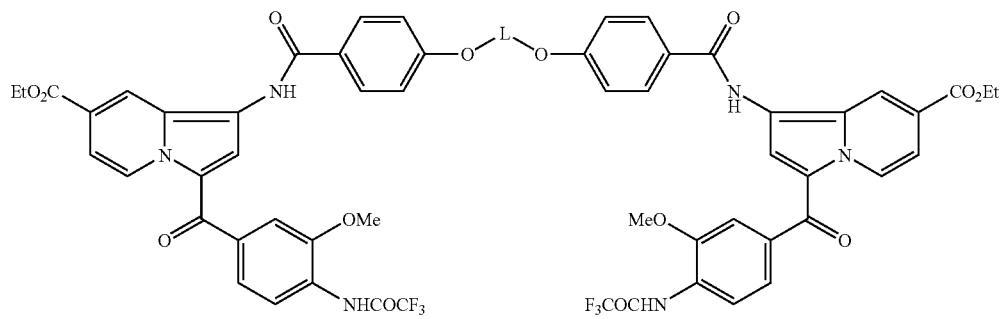
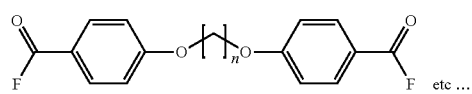 etc ...
Illustration of the case where $R_1$ possesses $NH_2$:
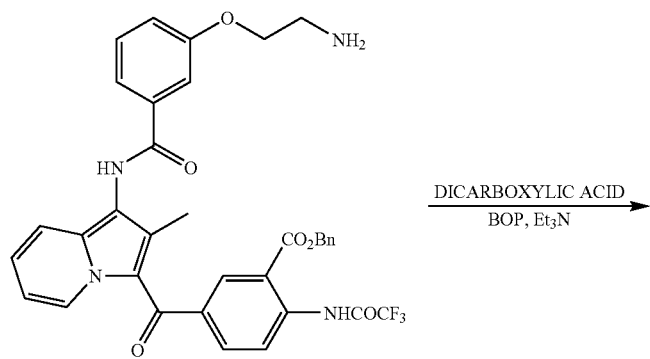 →[DICARBOXYLIC ACID / BOP, Et₃N]

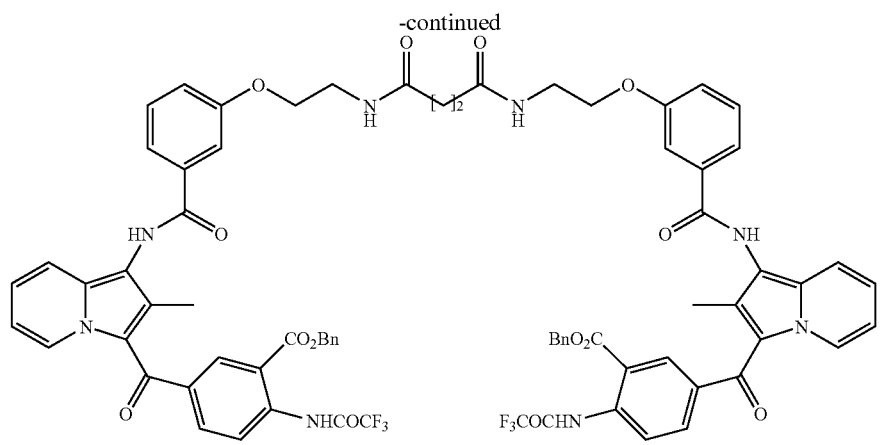

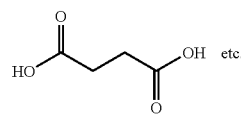

Method (II). When it is desired to dimerize monomer units M-W, with R, $R_1$, $R_2$, $R_3$ or $R_4$ being or having a carboxylic acid, and in which R or $R_1$ is or has an amino function W, such a monomer M-W can be reacted with a silylation agent such as trimethylsilyl chloride and a weak base such as triethylamine in order to protect the carboxylic acid function in the form of a silyl ester and to activate the amino function W in the form of a silylated amine, and then an acylation reaction can be carried out using a diacylating agent, such as an activated dicarboxylic acid in the presence of a suitable coupling agent such as BOP or PyBOP, or an acid dichloride or an acid difluoride, and a weak base such as triethylamine, followed by a hydrolysis in an acidic medium.

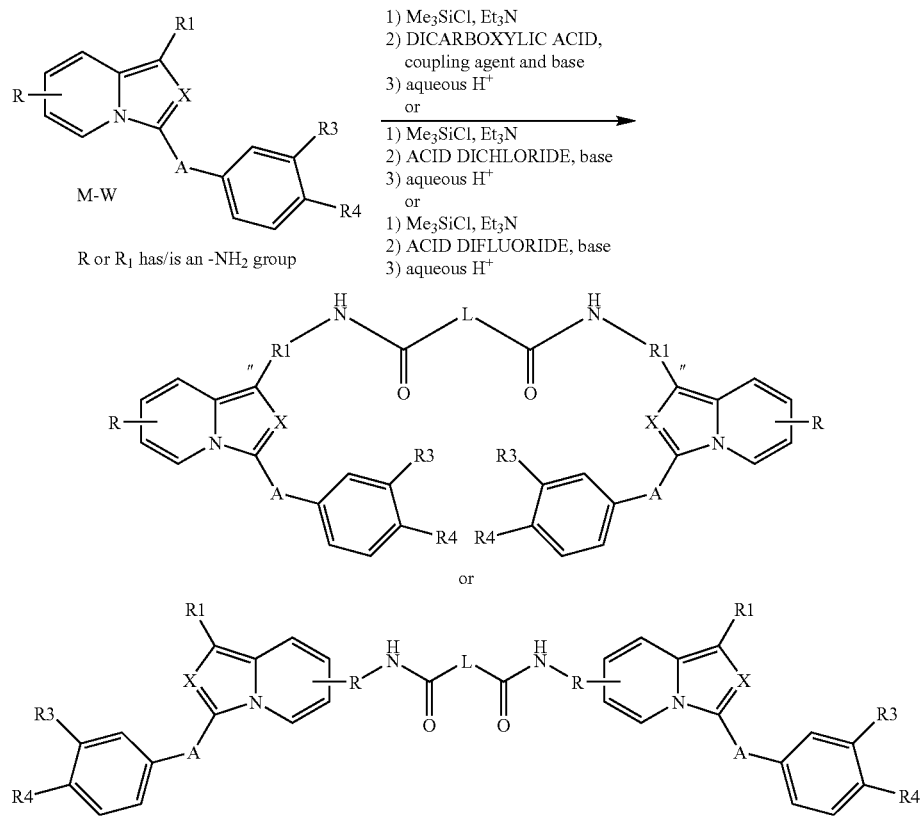

Illustrations of the case where M has a carboxylic acid function and where $R_1=NH_2$:

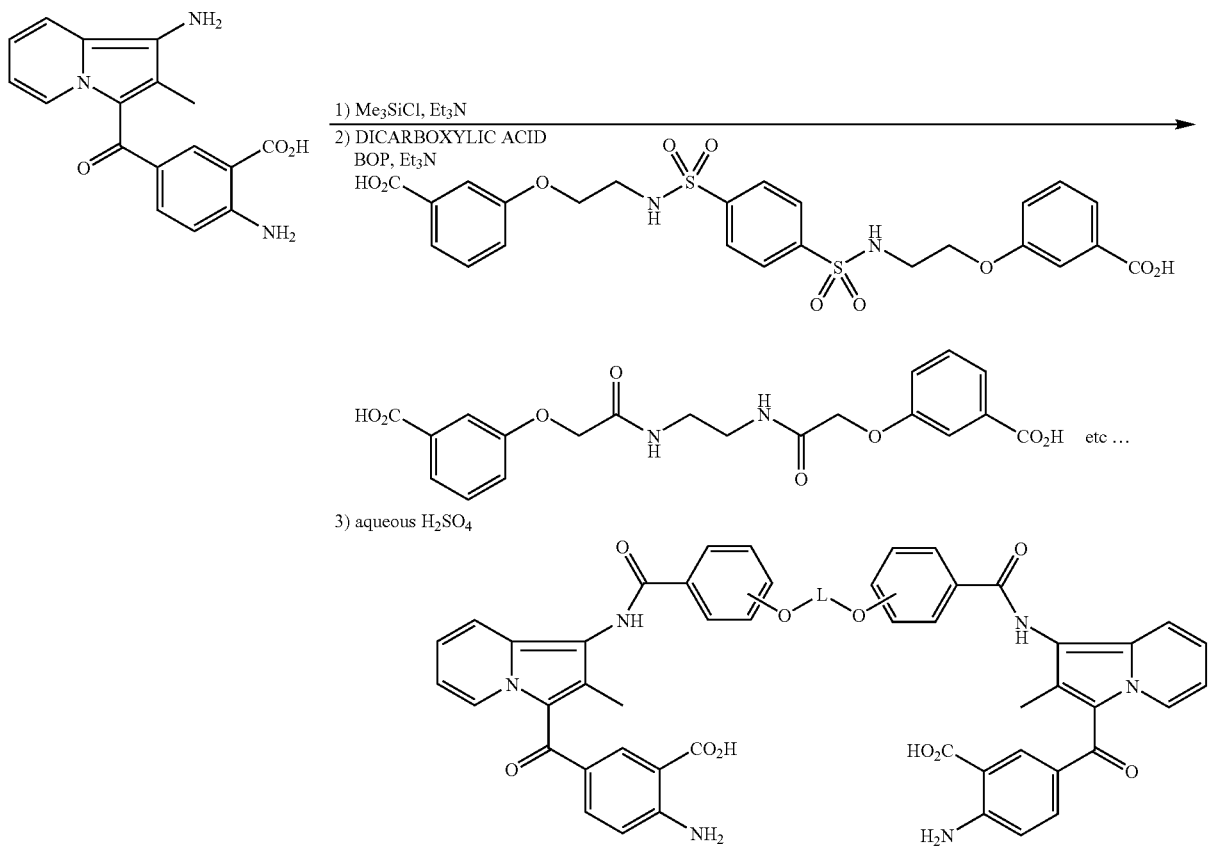

3) aqueous $H_2SO_4$

Method III). When it is desired to dimerize a monomer M-W, in which R, $R_1$ or $R_2$ is or has a carboxylic acid function W, use may be made of such a monomer M-W for carrying out an acylation using, for example, a diamine, a suitable coupling agent such as BOP, PyBOP or TBTU, and a weak base such as triethylamine:

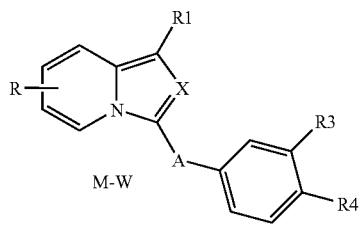

-continued

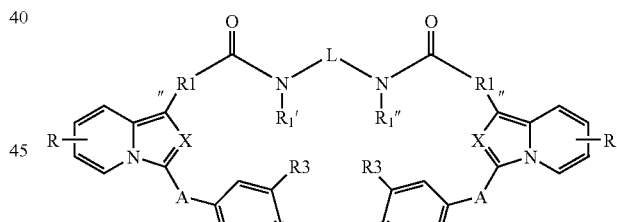

R or $R_1$ or $R_2$ has/is a —$CO_2H$ group or

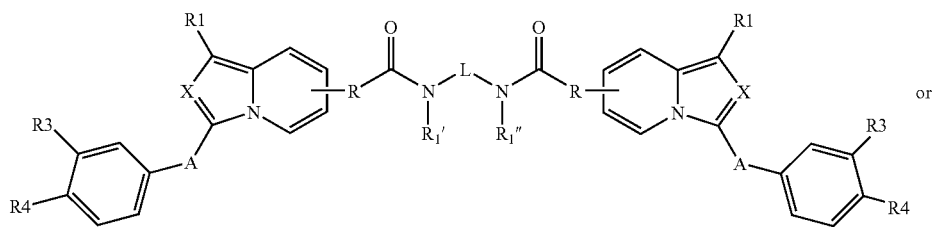

-continued
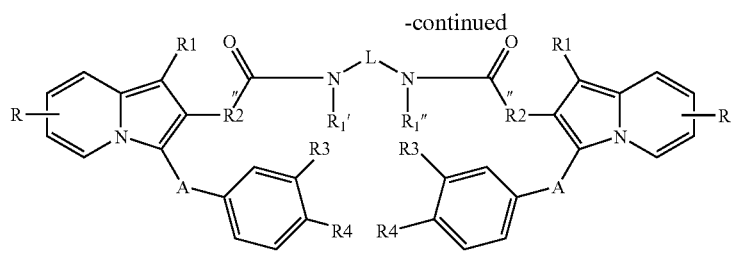
Illustrations of the case where $R_1$ possesses —$CO_2H$:
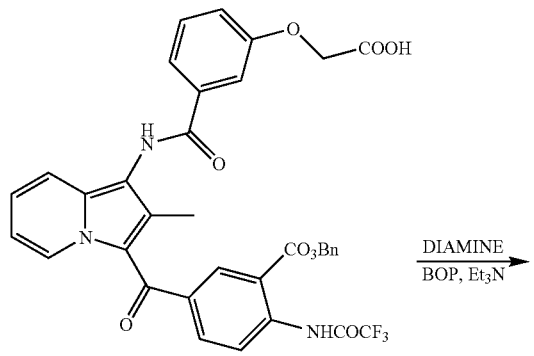
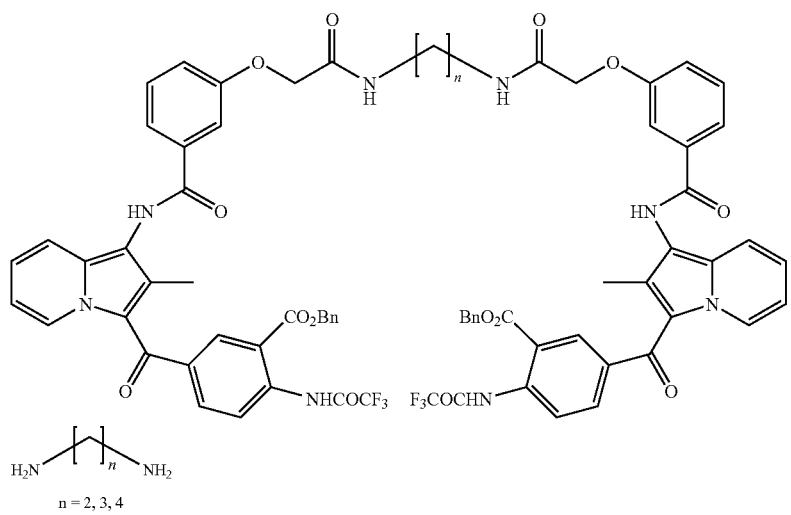
Illustration of the case where R possesses —$CO_2H$:
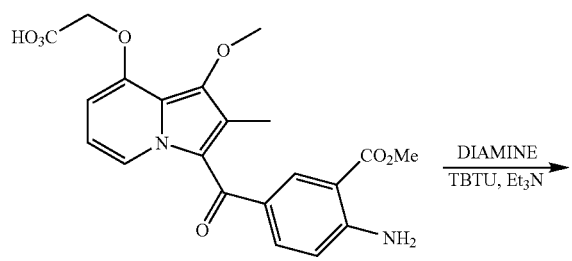

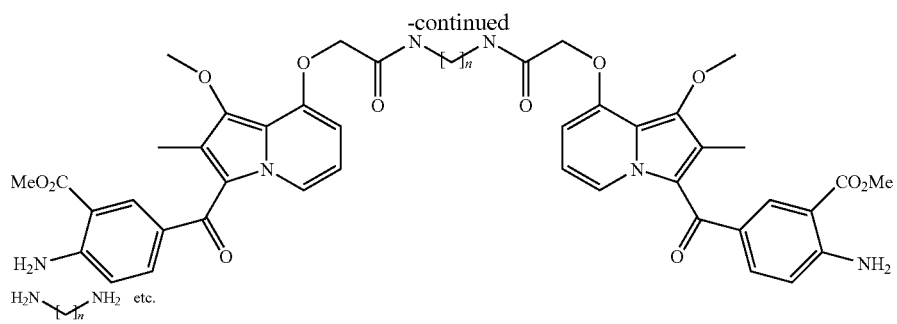
Illustration of the case where R=CO₂H:
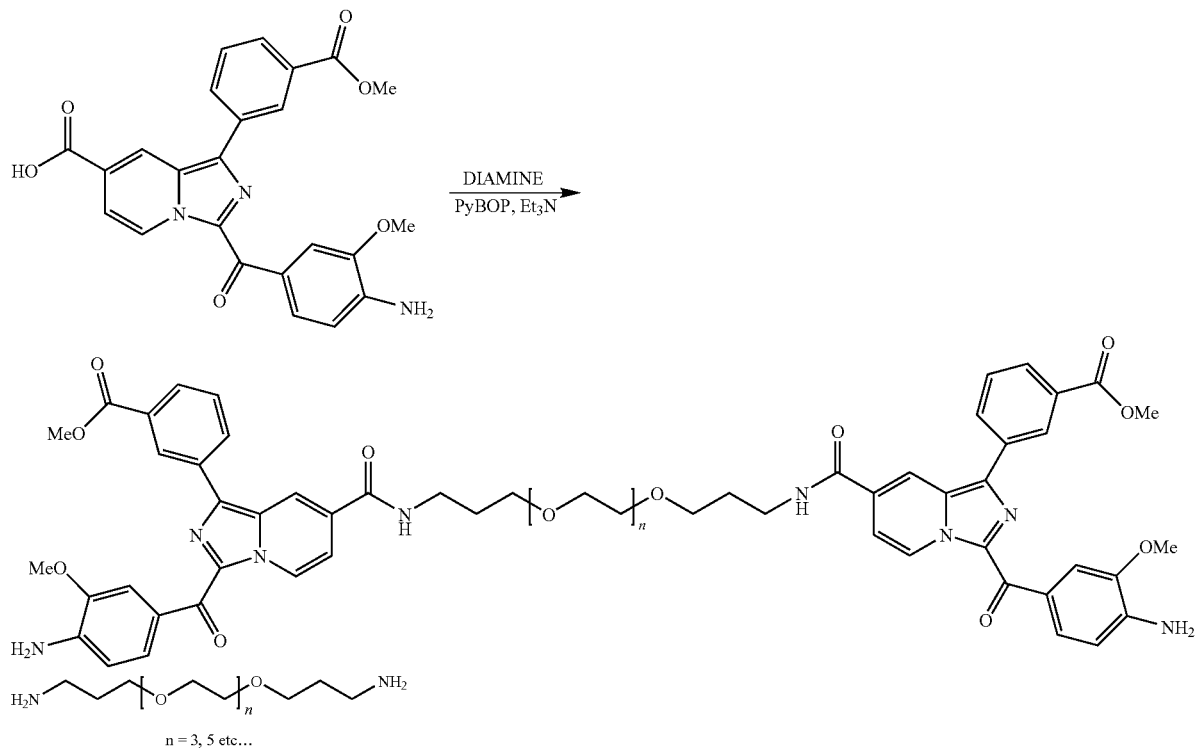
Method IV). When it is desired to dimerize a monomer M-W, in which R, R₁ or R₂ is or has a hydroxyl, amino, amido, carbamate or sulphonamido function W, use may be made of such a monomer M-W for carrying out an alkylation using a dihalogenated derivative and a base such as sodium hydride or potassium hexamethyldisilylamide:
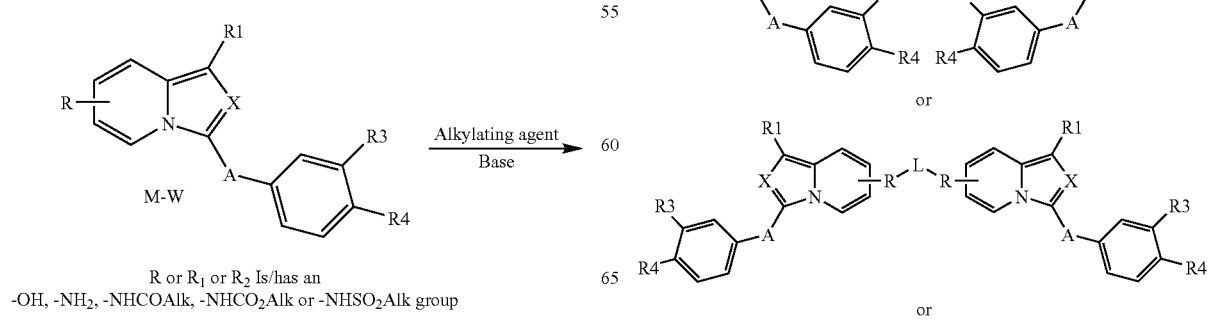

-continued
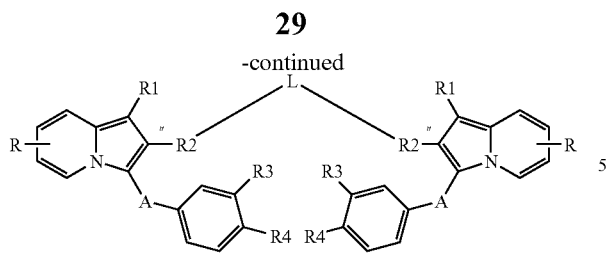
Illustrations of the case where R₁ possesses —OH:
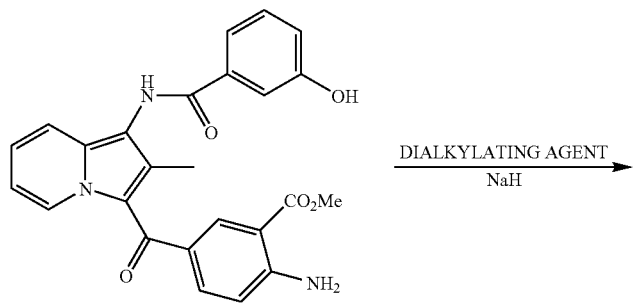
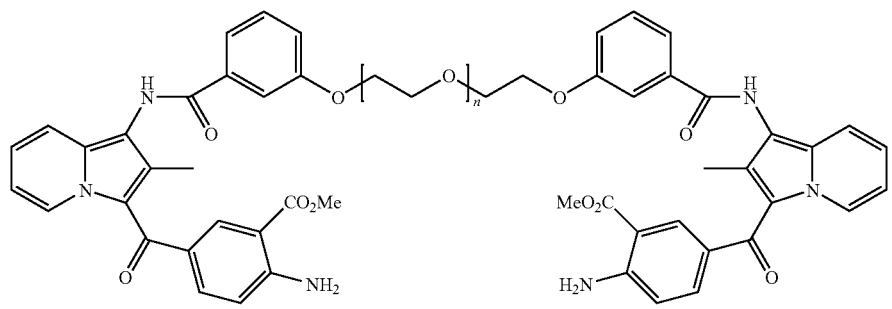
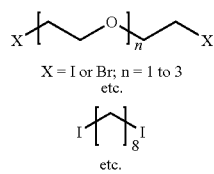
X = I or Br; n = 1 to 3
etc.
etc.
Illustrations of the case where R=—OH:
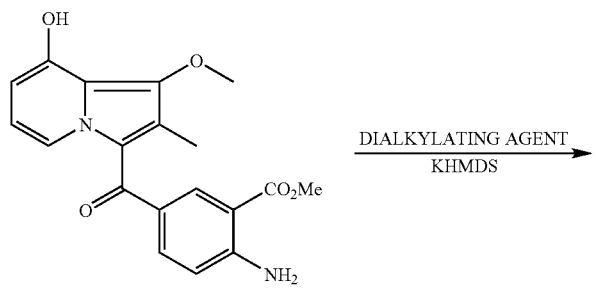

Method V). When it is desired to dimerize a monomer M-W, in which R, $R_1$ or $R_2$ is or has a halogen, use may be made of such a monomer M-W for carrying out a coupling reaction with a catalyst such as palladium, for example a SUZUKI coupling (*Synth. Commun.*, 1891, 11, 513) with a suitable diboronic acid or boronic diester in the presence of a catalyst such as palladium chloride (dppf) and a base such as potassium phosphate:

Illustrations of the case where $R_1$=halogen:

Method VI). A homodimer can also be obtained by carrying out the reactions described in the methods above on a single compound $M_1$-W (by adjusting the stoichiometry of the reactants $M_1$-W and U-L-U'), and then reacting the intermediate $M_1$-L-U' obtained, with a second compound $M_2$-W ($M_2$ identical to $M_1$):

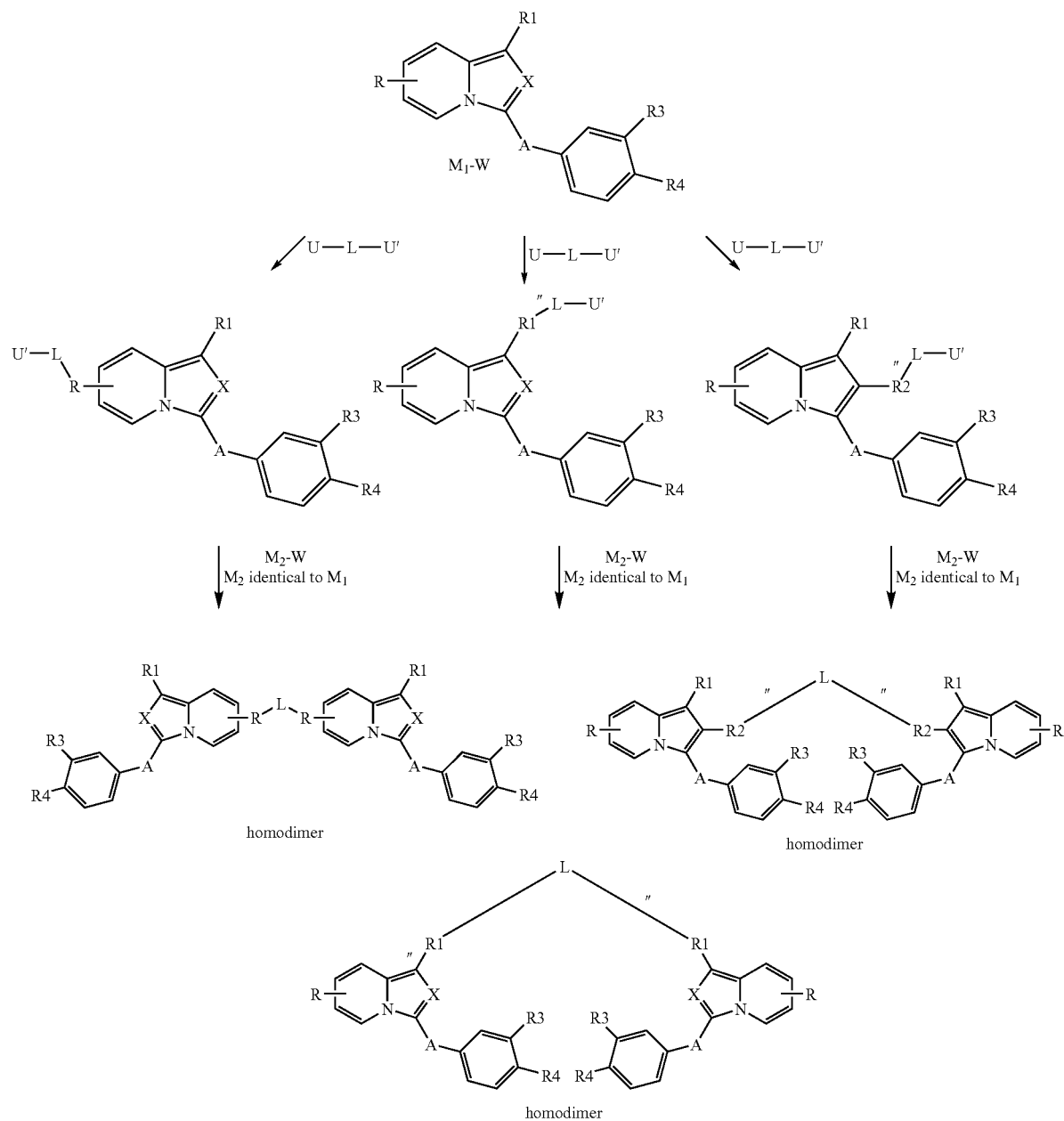
Illustration of a case of two-stage homodimerization:
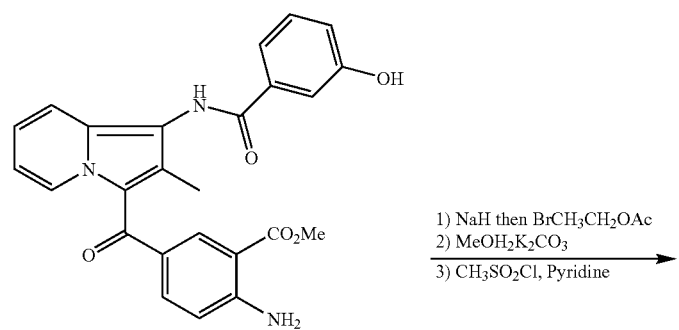
1) NaH then BrCH₃CH₂OAc
2) MeOH₂K₂CO₃
3) CH₃SO₂Cl, Pyridine -continued
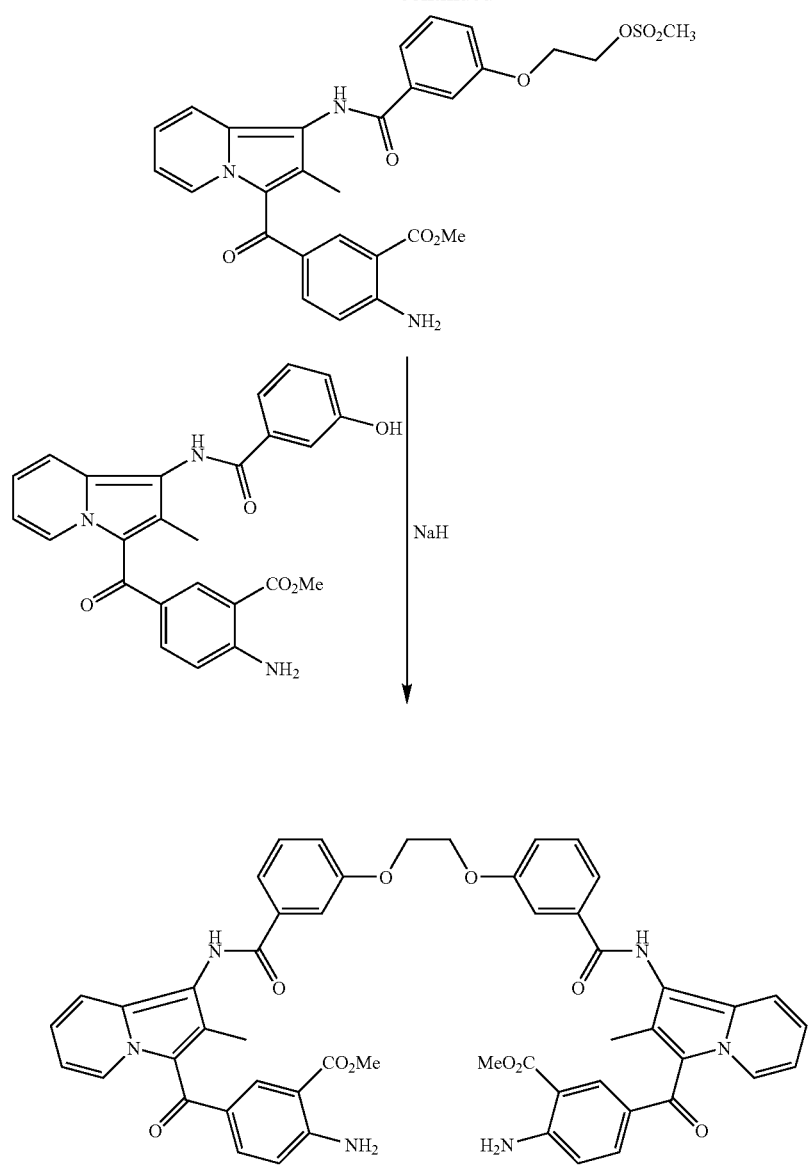
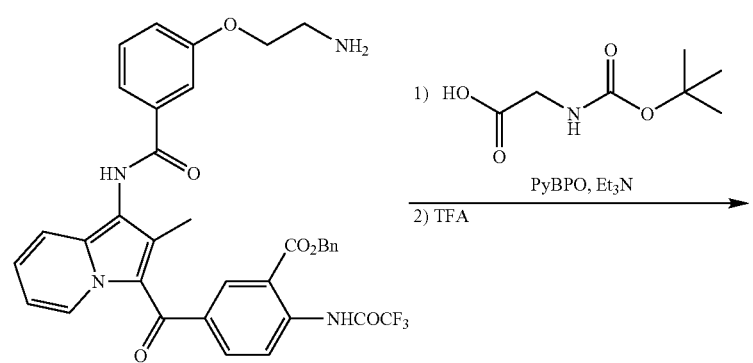

-continued

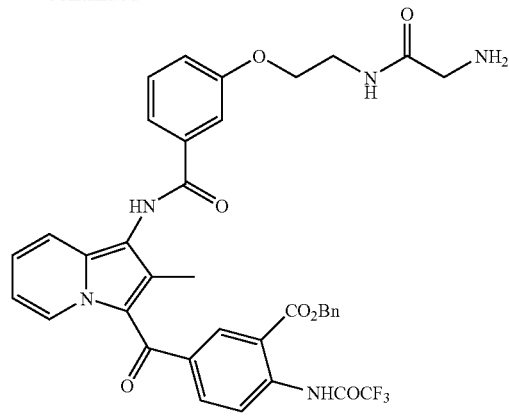

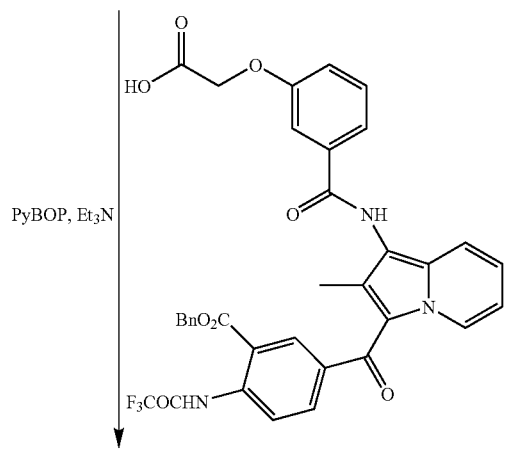

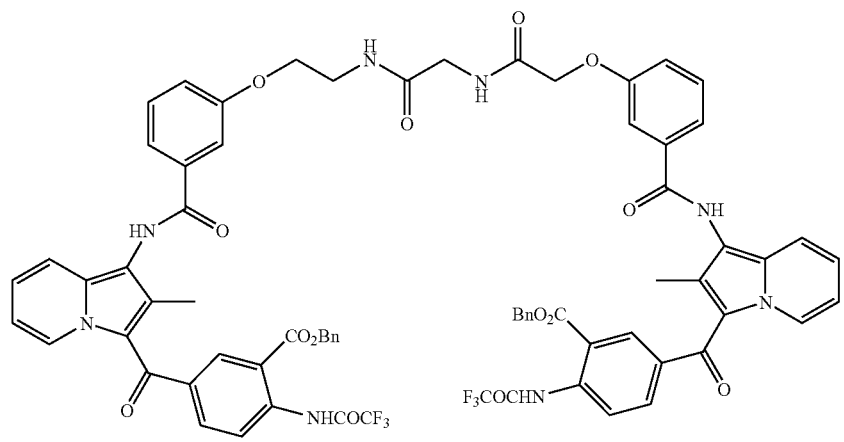

Method VII). A heterodimer can be obtained by carrying out the reactions described in the methods above on a single compound of formula $M_1$-W (by adjusting the stoichiometry of the reactants $M_1$-W and U-L-U') and then reacting the intermediate $M_1$-L-U' obtained, with a second compound of formula $M_2$-W (different from the first) so as to obtain a heterodimer either of homogeneous type (each monomer unit belongs to the same indolizine family X=C—$R_2$ or imidazo [1,5-a]pyridine family X=N) or of heterogeneous type (one monomer unit belongs to the indolizine family X=C—$R_2$ and the other to the imidazo[1,5-a]pyridine family X=N).

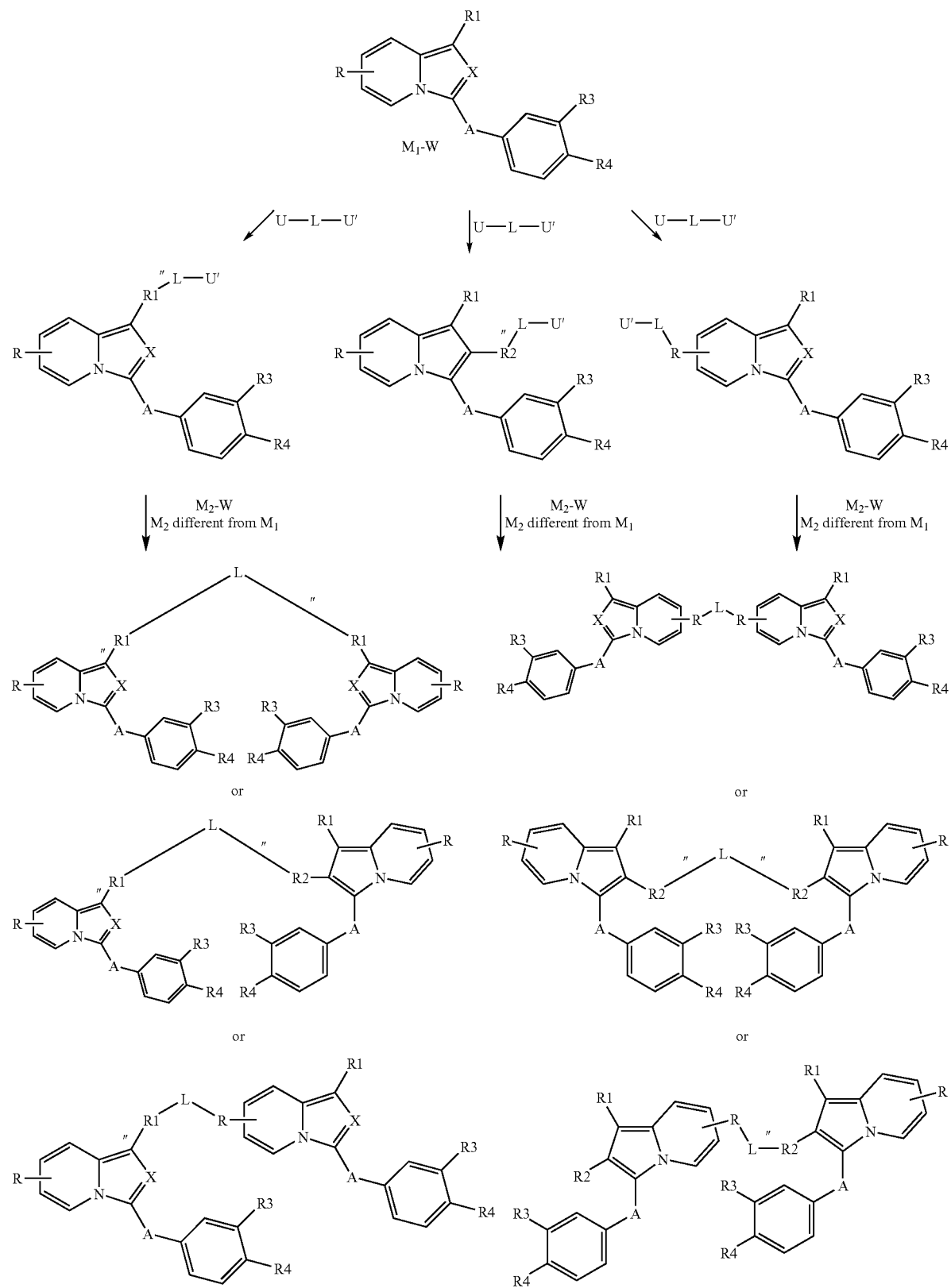

Illustration of the preparation of heterodimers:
The case of a homogeneous heterodimer:
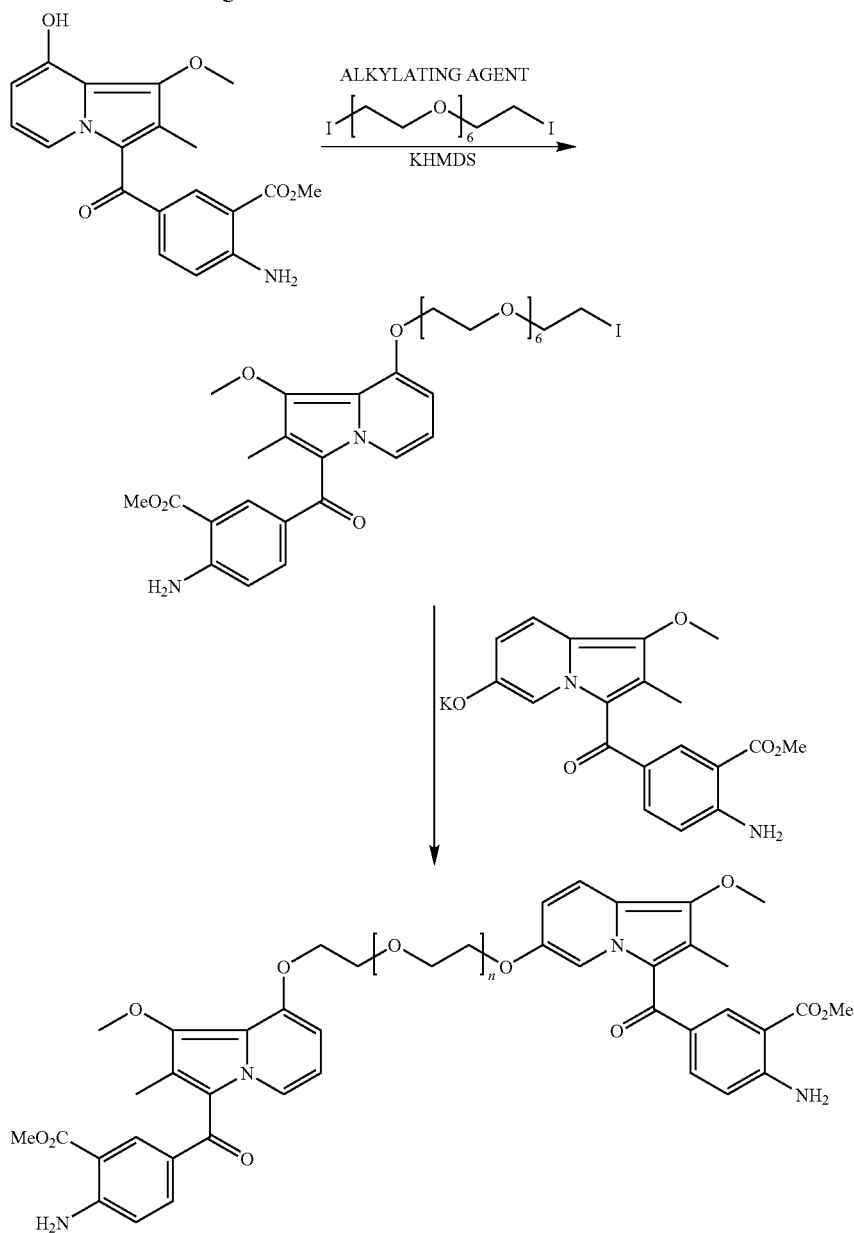
The case of a heterogeneous heterodimer:
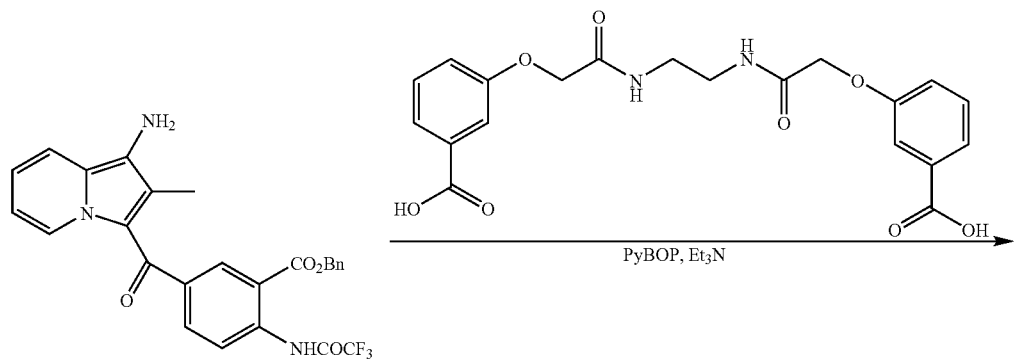

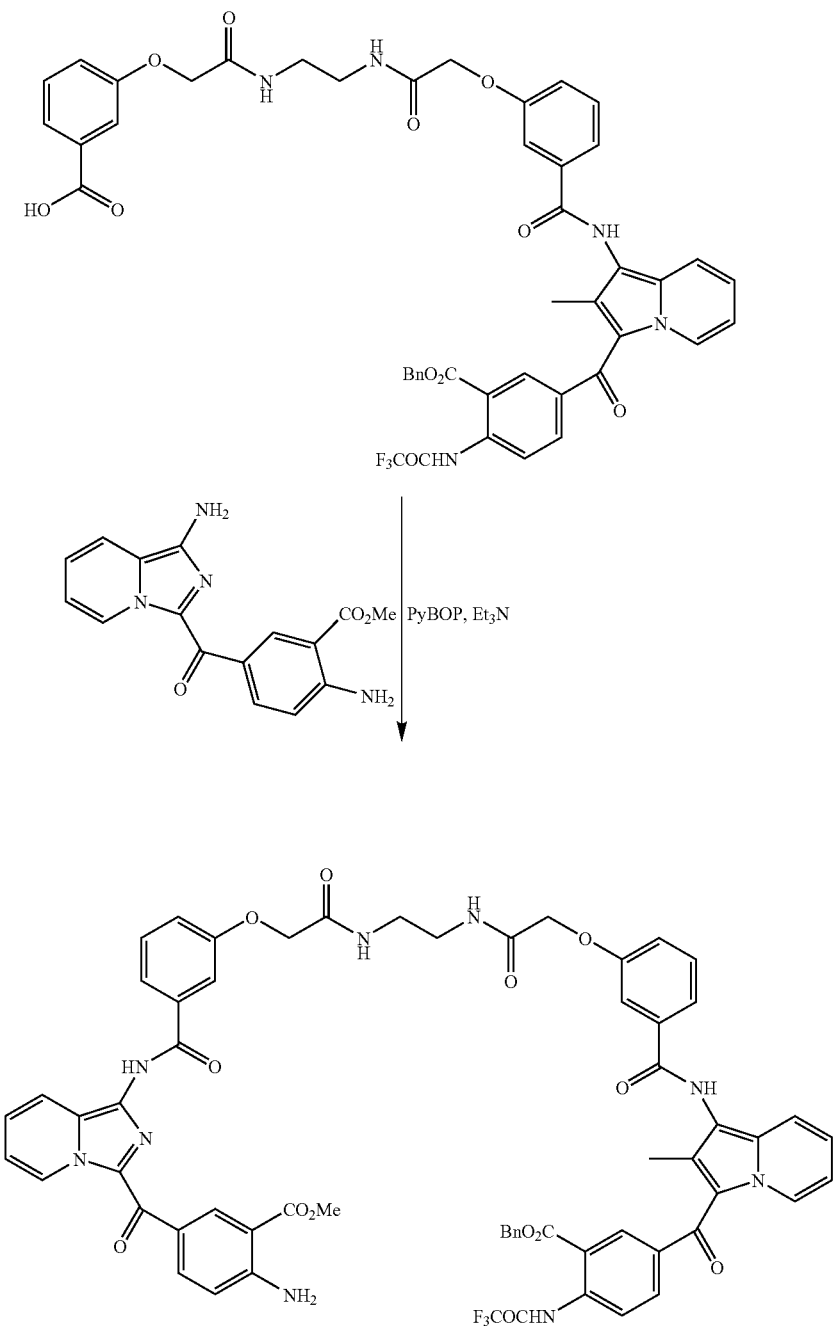

After the dimerization stage carried out according to one of the methods described above, one or more suitable deprotection stages are carried out so as to obtain the target agonist.

When R, $R_1$, $R_3$ and/or $R_4$ have a benzyl ester function, a reduction with palladium-on-charcoal in the presence of a hydrogen donor such as ammonium formate makes it possible to obtain the carboxylic acid as illustrated below:

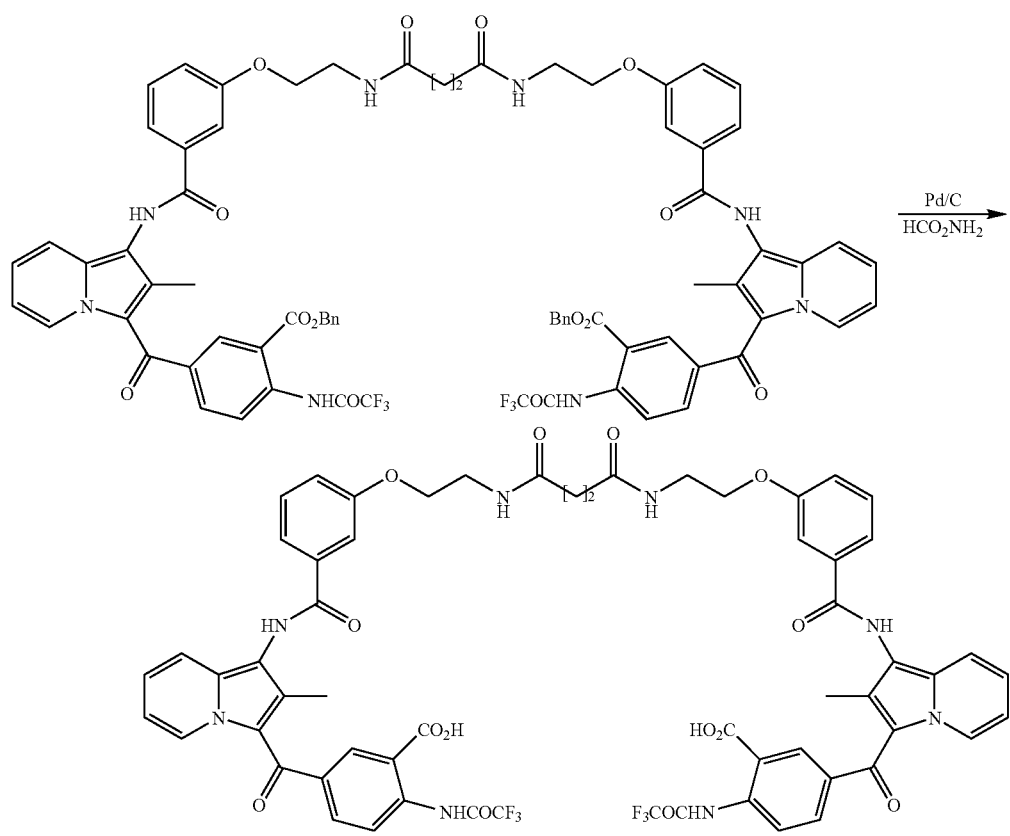
When R, $R_1$, $R_3$ and/or $R_4$ have a tert-butyl carbamate function, a deprotection with an acid such as trifluoroacetic acid provides the amine as illustrated below:
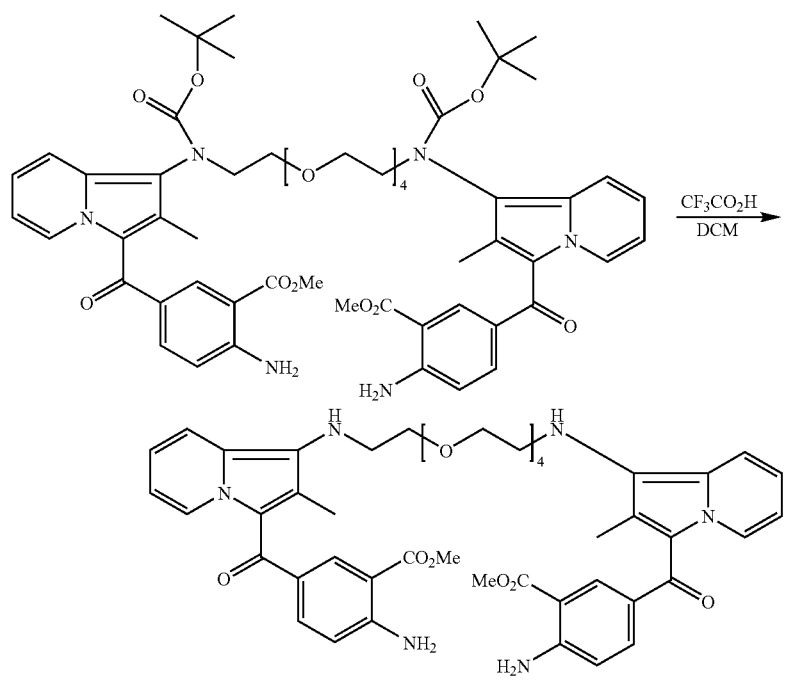

When R, $R_1$, $R_3$ and/or $R_4$ have an ester function and/or an amido function (such as acetamido, trifluoroacetamido), a hydrolysis in a basic medium with, for example, sodium hydroxide or lithium hydroxide, followed by an acidification, provides the target dimers, as illustrated below:
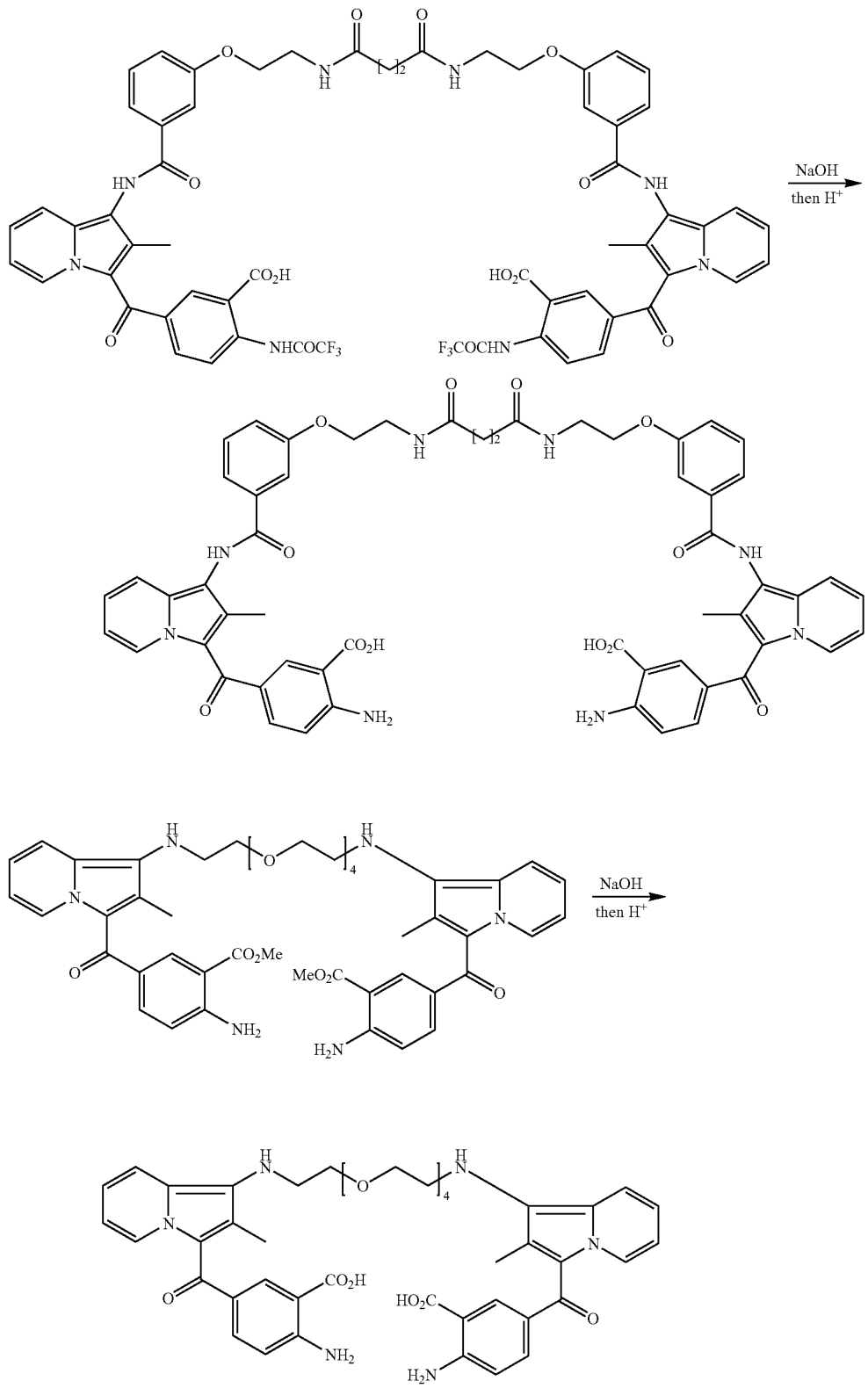

-continued

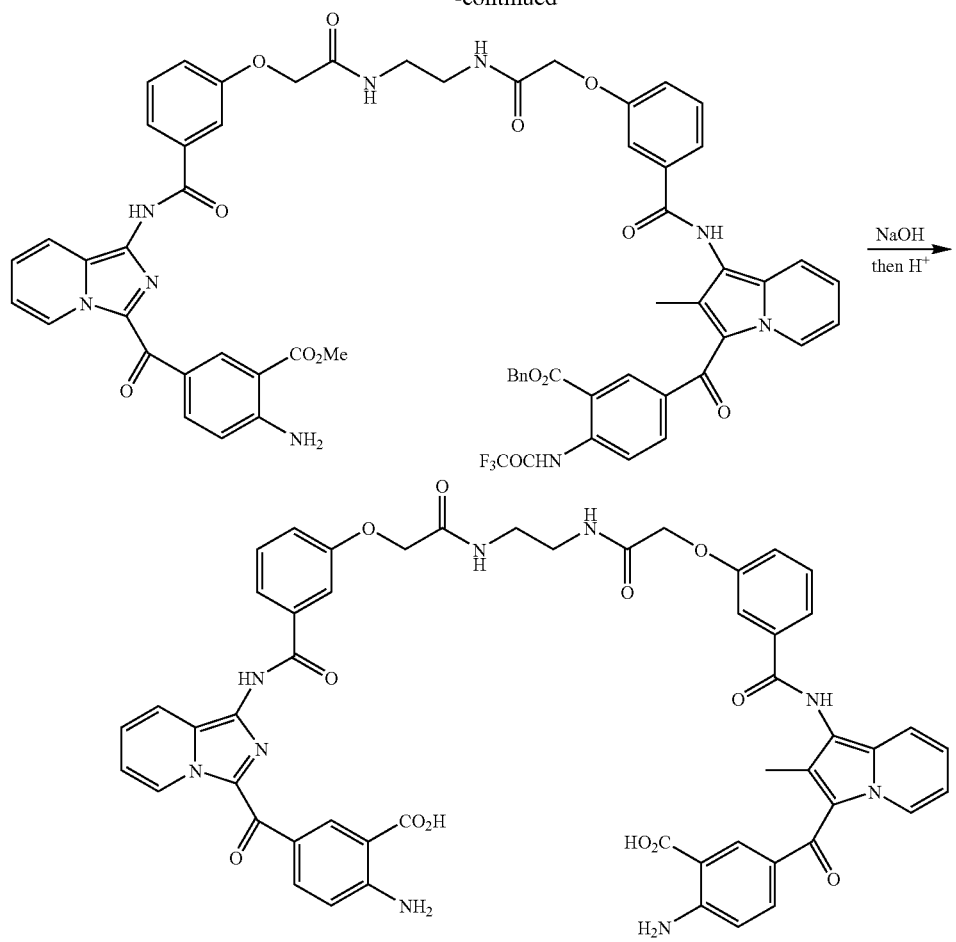

Among the compounds that are the subject of the invention, mention may be made of:

disodium salt of 3,3'-{3,6,9,12,15-pentaoxaheptadecane-1,17-diylbis[oxy(1-methoxy-2-methylindolizine-8,3-diyl)carbonyl]}bis(6-aminobenzoic acid)

disodium salt of 3,3'-(3,6,9,12,15-pentaoxaheptadecane-1,17-diylbis{oxy[3-(4-amino-3-methoxybenzoyl)imidazo[1,5-a]pyridine-8,1-diyl]})dibenzoic acid disodium salt of 3,3'-{3,6,9,12,15,18-hexaoxaicosane-1,20-diylbis[oxy(1-methoxy-2-methylindolizine-6,3-diyl)carbonyl]}bis(6-aminobenzoic acid)

disodium salt of 3,3'-{3,6,9,12,15-pentaoxaheptadecane-1,17-diylbis[oxy(1-methoxy-2-methylindolizine-6,3-diyl)carbonyl]}bis(6-aminobenzoic acid)

disodium salt of 3,3'-{3,6,9,12,15,18-hexaoxaicosane-1,20-diylbis[oxy(2-methylindolizine-1,3-diyl)carbonyl]}bis(6-aminobenzoic acid)

disodium salt of 3,3'-{ethane-1,2-diylbis[oxyethane-2,1-diyloxy-3,1-phenylenemethyleneoxy(2-methylindolizine-1,3-diyl)carbonyl]}bis(6-aminobenzoic acid)

disodium salt of 3,3'-{octane-1,8-diylbis[oxy-3,1-phenylenecarbonylimino(2-methylindolizine-1,3-diyl)carbonyl]}bis(6-aminobenzoic acid)

disodium salt of 3,3'-{ethane-1,2-diylbis[oxyethane-2,1-diyloxy-3,1-phenylenecarbonylimino(2-methylindolizine-1,3-diyl)carbonyl]}bis(6-aminobenzoic acid)

disodium salt of 3,3'-{(1,4-dioxobutane-1,4-diyl)bis[iminoethane-2,1-diyloxy-3,1-phenylenecarbonylimino(2-methylindolizine-1,3-diyl)carbonyl]}bis(6-aminobenzoic acid)

disodium salt of 3,3'-{carbonyl bis[iminoethane-2,1-diyloxy-3,1-phenylenecarbonylimino(2-methylindolizine-1,3-diyl)carbonyl]}bis(6-aminobenzoic acid)

disodium salt of 3,3'-{ethane-1,2-diylbis[imino(2-oxoethane-2,1-diyl)oxy-3,1-phenylenecarbonylimino(2-methylindolizine-1,3-diyl)carbonyl]}bis(6-aminobenzoic acid)

disodium salt of 3,3'-{propane-1,3-diylbis[imino(2-oxoethane-2,1-diyl)oxy-3,1-phenylenecarbonylimino(2-methylindolizine-1,3-diyl)carbonyl]}bis(6-aminobenzoic acid)

disodium salt of 3,3'-{butane-1,4-diylbis[imino(2-oxoethane-2,1-diyl)oxy-3,1-phenylenecarbonylimino(2-methylindolizine-1,3-diyl)carbonyl]}bis(6-aminobenzoic acid)

disodium salt of 3,3'-{ethane-1,2-diylbis[imino(2-oxoethane-2,1-diyl)oxy-4,1-phenylenecarbonylimino(2-methylindolizine-1,3-diyl)carbonyl]}bis(6-aminobenzoic acid)

disodium salt of 3,3'-{ethane-1,2-diylbis[oxyethane-2,1-diyloxy-4,1-phenylenecarbonylimino(2-methylindolizine-1,3-diyl)carbonyl]}bis(6-aminobenzoic acid)

disodium salt of 3,3'-{oxybis[ethane-2,1-diyloxyethane-2,1-diyloxy-4,1-phenylene(2-methylindolizine-1,3-diyl)carbonyl]}bis(6-aminobenzoic acid)

disodium salt of 3,3'-{ethane-1,2-diylbis[oxyethane-2,1-diyloxy-3,1-phenylene(2-methylindolizine-1,3-diyl)carbonyl]}bis(6-aminobenzoic acid)

disodium salt of 3,3'-{oxybis[ethane-2,1-diyloxyethane-2,1-diyloxy-3,1-phenylene(2-methylindolizine-1,3-diyl)carbonyl]}bis(6-aminobenzoic acid)

disodium salt of 3,3'-{hexane-1,6-diylbis[imino(2-oxoethane-2,1-diyl)oxy-3,1-phenylene(2-methylindolizine-1,3-diyl)carbonyl]}bis(6-aminobenzoic acid)

disodium salt of 3,3'-{hexane-1,6-diylbis[imino(2-oxoethane-2,1-diyl)oxy-4,1-phenylene(2-methylindolizine-1,3-diyl)carbonyl]}bis(6-aminobenzoic acid)

disodium salt of 2-amino-5-[(1-{[3-(2-{[2-({[3-({[3-(4-amino-3-carboxybenzoyl)imidazo[1,5-a]pyridin-1-yl]amino}carbonyl)phenoxy]acetyl}amino)ethyl]amino}-2-oxoethoxy)benzoyl]amino}-2-methylindolizin-3-yl)carbonyl]dibenzoic acid.

Thus, the compounds of the invention have an FGF receptor agonist activity. They thus bring about the dimerization of the receptor and, by virtue of their low toxicity and their pharmacological and biological properties, the compounds of the present invention represent a therapy of choice in pathologies related to the activation of angiogenesis.

Ischaemia is a decrease in the arterial circulation in an organ, resulting in a reduction in the oxygen concentration in the damaged tissues. In post-ischaemic revascularization mechanisms, two main mechanisms are involved: angiogenesis and arteriogenesis. Angiogenesis is the process by which new capillary vessels are generated from pre-existing vessels. Arteriogenesis contributes to the development (increase in size and in calibre) of the collateral vessels around the zone rendered ischaemic or avascular zone.

Among the growth factors involved in these revascularization processes, the FGF family, and in particular FGF-2, has been the most widely described (Post, M. J., Laham, R., Sellke, F. W. & Simons, M. Therapeutic angiogenesis in cardiology using protein formulations. Cardiovasc Res 49, 522-31, 2001). FGF2 is an 18 KDalton protein that induces proliferation, migration and protease production by endothelial cells in culture. FGF2 also induces neovascularization in vivo and the development of collateral vessels after ligaturing of a vessel in pharmacological models.

FGF2 interacts with endothelial cells by means of two classes of receptors, high-affinity receptor tyrosine kinases (FGF-R1, -R2, -R3, -R4) and low-affinity heparan sulphate proteoglycan type receptors that are located at the cell surface and are an integral part of the extracellular matrices. Although the paracrine role of FGF2 on endothelial cells has been largely described, FGF2 could also intervene on these cells through an autocrine process: FGF2 stimulates the production of other angiogenic factors (in particular VEGF) (Janowska-Wieczorek, A., Majka, M., Ratajczak, J. & Ratajczak, M. Z. Autocrine/paracrine mechanisms in human hematopoiesis. Stem Cells 19, 99-107, 2001) and the synthesis of proteases on endothelial cells (including plasminogen activator and metalloproteinases) required for digestion of the extracellular matrix during angiogenic processes (Carmeliet, P. Mechanisms of angiogenesis and arteriogenesis. Nat Med 6, 389-95, 2000). Moreover, FGF2 exhibits a proliferative and migratory activity on other cell types involved in vessel maturation: smooth muscle cells, fibroblasts and pericytes. Thus, FGF2 and its receptors represent very relevant targets for therapies aimed at inducing the processes of angiogenesis and of arteriogenesis (Khurana, R. & Simons, M. Insights from angiogenesis trials using fibroblast growth factor for advanced arteriosclerotic disease. Trends Cardiovasc Med 13, 116-22, 2003). Several pieces of evidence demonstrate that FGF2 is also involved in the differentiation of angioblasts into endothelial progenitor cells and thus contribute to revascularization after an occlusion (Burger, P. E. et al. Fibroblast growth factor receptor-1 is expressed by endothelial progenitor cells. Blood 100, 3527-35, 2002).

Although, in the zone rendered ischaemic, subsequent hypoxic phenomena induce the expression of angiogenic factors (in particular VEGF and FGF2), the natural angiogenic and arteriogenic compensatory processes are often not sufficient. Two explanations are possible: the production of angiogenic cytokines is inadequate or their responses are reduced. Moreover, patients requiring post-ischaemic revascularization are often elderly and exhibit pathological characteristics (diabetes, hypercholesterolaemia, etc.) that limit the role of angiogenic cytokines after ischaemia. It has been shown that these patients respond to the administration of exogenous angiogenic and arteriogenic cytokines. Thus, strategies aimed at increasing the response of the cells of the vascular tree are strategies suitable for increasing post-ischaemic revascularization and in particular cardiac or coronary artery revascularization (Freedman, S. B. & Isner, J. M. Therapeutic angiogenesis for ischemic cardiovascular disease. J Mol Cell Cardiol 33, 379-93, 2001; Freedman, S. B. & Isner, J. M. Therapeutic angiogenesis for coronary artery disease. Ann Intern Med 136, 54-71, 2002).

The compounds presented in this invention are potent and selective FGFR agonists. Their abilities to induce angiogenesis has been demonstrated in vitro and in vivo.

One of the applications of the compounds of the invention is post-ischaemic treatment after occlusion at the cardiac level or at the level of peripheral arteries. As regards the treatment of cardiac ischaemia, one of the most promising clinical trials is a trial where FGF-2 was sequestered in microspheres of alginate in the presence of heparin (Laham, R. J. et al. Local perivascular delivery of basic fibroblast growth factor in patients undergoing coronary bypass surgery: results of a phase I randomized, double-blind, placebo-controlled trial. Circulation 100, 1865-71, 1999). These microspheres were implanted close to the ischaemic locus in the myocardium. After 90 days, all the patients treated with FGF2 showed no ischaemic cardiac symptom. In comparison, in the control group, 3 of the 7 patients had persistent symptoms at 90 days and 2 patients had to resort to vascular surgery. Interestingly, the benefit from the therapy was maintained after 3 years of follow-up. These observations suggest that compounds that mimic FGF2 can represent a therapy of choice for the treatment of the consequences of cardiac ischaemia.

Three clinical trials on the injection of FGF2 into the coronary artery have been carried out in the treatment of coronary artery narrowing (Laham, R. J. et al. Intracoronary basic fibroblast growth factor (FGF-2) in patients with severe ischemic heart disease: results of a phase I open-label dose escalation study. J Am Coll Cardiol 36, 2132-9, 2000; Simons, M. et al. Pharmacological treatment of coronary artery disease with recombinant fibroblast growth factor-2: double-blind, randomized, controlled clinical trial. Circulation 105, 788-93, 2002; Unger, E. F. et al. Effects of a single intracoronary injection of basic fibroblast growth factor in stable angina pectoris. Am J Cardiol 85, 1414-9, 2000). The result of these three trials shows that intra-coronary infusions of FGF2 are well-tolerated and significantly improve the patients' state. Thus, the compounds described in the invention can find an application in the treatment of diseases associated with coronary artery narrowing, and in particular in the treatment of angina pectoris.

Distal artery diseases, and in particular arterites of the lower limbs, are due to chronic obstruction of the arterioles that irrigate the extremities. The most common symptoms are numbness, weakness and painful stiffness due to distal muscle group fatigue. These phenomena are the result of a decrease in arterial calibre in the extremities, caused by atherosclerosis. These pathologies affect mainly the lower limbs.

In a phase I clinical trial, patients with peripheral artery pathologies resulting in claudication were given injections of FGF2 (Lazarous, D. F. et al. Basic fibroblast growth factor in patients with intermittent claudication: results of a phase I trial. J Am Coll Cardiol 36, 1239-44, 2000). In this context, the FGF2 was well-tolerated in these patients and the clinical data suggest a beneficial effect of the FGF2, in particular on improved walking. These clinical data suggest that the compounds of the invention represent a therapeutic tool of choice for the treatment of diseases associated with a distal artery obstruction.

Buergers disease or thromboangiitis obliterans affects the distal vascular structures and is characterized by distal arteritis of the legs with pain and ulcerations. In this context, an induction of angiogenesis and vasculogenesis would represent a therapy for this pathology. The compounds of said invention represent a therapy of choice for thromboangiitis obliterans.

Glutamate is a putative transmitter of neurons of the dorsal ganglia and bradykinin is a molecule produced during inflammation that may activate and sensitize nociceptive fibres. In this context, FGF2 could modulate inflammatory pain despite the fact that no regulatory effect of FGF2 on nociceptive fibres has been demonstrated in vivo. However, it has been shown that FGF2 completely blocks bradykinin-stimulated glutamate release in vitro (Rydh-Rinder et al. (2001) Regul. Pept. 102:69-79). By virtue of the agonist activity of FGF receptors, the compounds of said invention would be a therapy of choice in the treatment of nociception and thus in the treatment of chronic pain.

Peripheral neuropathy is an axonal or demyelinizing attack on the motor and/or sensory peripheral nerve that leads to desensitization of the distal limbs. One of the consequences of the nerve damage may be a perforating ulcer, which is to be particularly feared when there is considerable damage to the profound sensitivity since, in this case, the body's weight has a tendency to always be carried by the same support points. One of the major secondary complications of diabetes is the chronic development of peripheral neuropathy. In this context, it has been demonstrated that FGF2 induces axonal regeneration that could be a therapy of choice in the treatment of peripheral nerve lesion and therefore in peripheral neuropathy (Basic fibroblast growth factor isoforms promote axonal elongation and branching of adult sensory neurons in vitro. Klimaschewski L, Nindl W, Feurle J, Kavakebi P, Kostron H. Neuroscience. 2004; 126(2): 347-53). By virtue of the FGF receptor agonist activity, the compounds of said invention would represent a treatment of choice in peripheral neuropathy in normal or diabetic patients.

The proliferation and migration of vascular smooth muscle cells contribute to intimal hypertrophy of arteries and thus plays a predominant role in atherosclerosis and in post-angioplasty and post endarterectomy restenosis. It has been demonstrated that an angiogenic factor, VEGF, significantly reduces intimal thickening by accelerating re-endothelialization (Van Belle, E., Maillard, L., Tio, F. O. & Isner, J. M. Accelerated endothelialization by local delivery of recombinant human vascular endothelial growth factor reduces in-stent intimal formation. Biochem Biophys Res Commun 235, 311-6, 1997). Thus a compound such as the compounds of the present invention having pro-angiogenic activity represents a therapy of choice in the treatment of atherosclerosis and in the inhibition of post-angioplasty or post-endarterectomy restenosis.

The vascular network is essential to tissue development and preservation. By promoting the delivery of nutrients, oxygen and cells, the blood vessels help to maintain the functional and structural integrity of tissues. In this context, angiogenesis and vasculogenesis make it possible to preserve and infuse the tissues after ischaemia. Angiogenic growth factors such as VEGF and FGF2 thus promote revascularization for tissue regeneration. The compounds presented in the invention could represent a treatment of choice in treatment for muscle regeneration.

The muscle regeneration processes on dystrophic or normal muscles depend on the provision of cytokines and of angiogenic growth factors at the local level (Fibbi, G., D'Alessio, S., Pucci, M., Cerletti, M. & Del Rosso, M. Growth factor-dependent proliferation and invasion of muscle satellite cells require the cell-associated fibrinolytic system. Biol Chem 383, 127-36, 2002). It has been proposed that the FGF system is an essential system for muscle regeneration, and for myoblast survival and proliferation (Neuhaus, P. et al. Reduced mobility of fibroblast growth factor (FGF)-deficient myoblasts might contribute to dystrophic changes in the musculature of FGF2/FGF6/mdx triple-mutant mice. Mol Cell Biol 23, 6037-48, 2003). FGF2 and the compounds of said invention could be exploited in order to promote cardiac regeneration. They would thus improve myocardial perfusion after ischaemia (Hendel, R. C. et al. Effect of intracoronary recombinant human vascular endothelial growth factor on myocardial perfusion: evidence for a dose-dependent effect. Circulation 101, 118-21, 2000) and also the survival and progression of transplanted myoblasts, and in particular in Duchenne muscular dystrophy.

Angiogenesis is an essential phenomenon during cutaneous wound healing. The new vessels formed provide the oxygen and nutrients necessary for tissue repair. In the case of a diabetic patient, wound healing is a slow and difficult process that exhibits deficiencies in angiogenesis. FGFs are among the growth factors most involved in angiogenic processes during the wound-healing phase. Some FGFs are strongly overregulated in the cells of the dermis after a skin wound. By virtue of their FGF receptor agonist activities, the compounds of said invention would represent a therapy of choice for the treatment of wound healing in normal or diabetic patients.

Bioartificial pancreas transplantation is a very promising technique for the treatment of certain types of diabetes. It has just been clearly demonstrated, in diabetic rats, that the vascularization in the bioartificial pancreases is much greater when the latter are impregnated with microspheres carrying FGF2 (Sakurai, Tomonori; Satake, Akira, Sumi, Shoichiro, Inoue, Kazutomo, Nagata, Natsuki, Tabata, Yasuhiko. The Efficient Prevascularization Induced by Fibroblast Growth Factor 2 With a Collagen-Coated Device Improves the Cell Survival of a Bioartificial Pancreas. Pancreas. 28(3):e70-e79, April 2004). This revascularization thus improves the survival of the bioartificial pancreases implanted and, consequently, the survival of the graft. By virtue of their FGF receptor agonist activities, the compounds of said invention would represent a therapy of choice in improving bioartificial pancreatic graft survival in diabetic patients and, more generally, in improving graft revascularization and, consequently, graft survival.

Pigmentary retinitis is a pathology involving progressive retinal degeneration characterized by photoreceptor degeneration and retinal vessel obliteration. Recently, Lahdenranta et al. (An anti-angiogenic state in mice and humans with retinal photoreceptor cell degeneration. Proc Natl Acad Sci USA 98, 10368-73, 2001) have proposed that angiogenic growth factors regulate neurocoordination and associated vascularization of the retina by functioning simultaneously as photoreceptor survival factors and as an endothelial cell regulator. In this context, the intravitreal injection of FGF2 delays photoreceptor degeneration by acting on retinal survival and angiogenesis (Faktorovich, E. G., Steinberg, R. H., Yasumura, D., Matthes, M. T. & LaVail, M. M. Basic fibroblast growth factor and local injury protect photoreceptors from light damage in the rat. J Neurosci 12, 3554-67, 1992). These observations demonstrate the advantage of the compounds described in the invention as a suitable therapy in retinal degeneration, and in particular in pigmentary retinitis.

In the field of bone repair, one of the essential needs is that of finding agents that stimulate bone formation. Among the main growth factors, it is now clearly established that the systematic administration of FGF2 facilitates bone repair (Acceleration of fracture healing in nonhuman primates by fibroblast growth factor-2. Kawaguchi H, Nakamura K, Tabata Y, Ikada Y, Aoyama I, Anzai J, Nakamura T, Hiyama Y, Tamura M. J Clin Endocrinol Metab. 2001 (February; 86(2), 875-880). The local application of FGF2 in gelatine matrices accelerates bone repair in primates, suggesting that FGF2 would be clinically useful in the treatment of fractures. By virtue of the FGF receptor agonist properties, the compounds of said invention could represent a treatment of choice in bone repair.

Preeclampsia is a pathology of the placenta associated with a deficiency in vascularization (Sherer, D. M. & Abulafia, O. Angiogenesis during implantation, and placental and early embryonic development. Placenta 22, 1-13, 2001). These deficiencies in vascularization are thought to be due to a deficiency in angiogenesis and to lead to disturbances in the placenta that can result in the death of the foetus. The compounds of said invention could be a treatment of choice for overcoming a deficiency in angiogenesis in pre-eclamptic placentas.

In addition to the angiogenesis-inducing effects, growth factors such as VEGF or FGF2 protect endothelial cells against intrinsic and extrinsic inducers of apoptosis. The intrinsic signalling pathway is activated by the mitochondria in response to a stress such as deprivation or damage to the DNA, whereas the extrinsic signalling pathway is induced by the binding of pro-apoptotic factors such as TNF-α or Fas. It has now been clearly described that VEGF and FGF2 are two endothelial cell survival factors (Role of Raf in Vascular Protection from Distinct Apoptotic Stimuli: A Alavi, J. D. Hood, R. Frausto, D. G. Stupack, D. A. Cheresh: Science 4 Jul. 2003: Vol. 301, No. 5629, pp 94-96). Acute respiratory distress syndrome (ARDS) is characterized by cardiovascular and neuropsychiatric problems. In the context of the cardiovascular problems, the patients exhibit considerable vascular lesions and, in particular, substantial induction of apoptosis in endothelial cells. Recently, Hamacher et al. have demonstrated that bronchoalveolar lavage fluids from patients suffering from ARDS exhibit a pro-apoptotic activity against lung microvascular endothelial cells (Tumor necrosis factor-alpha and angiostatin are mediators of endothelial cytotoxicity in bronchoalveolar lavages of patients with acute respiratory distress syndrome. Am J Respir Crit Care Med. 2002 Sep. 1; 166(5): 651-6: Hamacher J, Lucas R, Lijnen H R, Buschke S, Dunant Y, Wendel A, Grau G E, Suter P M, Ricou B). By virtue of their anti-apoptotic activity on endothelial cells, the products of said invention could provide a treatment of choice in vascular improvement in patients suffering from vascular lesions, and in particular patients suffering from ARDS.

The endogenous overregulation of FGF7 (or KGF) and of FGF18 appears to be an important mechanism for promoting the proliferation, migration and protection of hair follicles in pathological cases or subsequent to tumour treatment (Comprehensive Analysis of FGF and FGFR Expression in Skin: FGF18 is Highly Expressed in Hair Follicles and Capable of Inducing Anagen from Telogen Stage Hair Follicles. Mitsuko Kawano, Akiko Komi-Kuramochi, Masahiro Asada, Masashi Suzuki, Junko Oki, Ju Jiang and Toru Imamura). By virtue of their FGF receptor agonist activity, the compounds of said invention could provide a treatment of choice for hair follicle repair protection and in the protection and regulation of hair growth.

The incidence of obesity and of type II diabetes is constantly on the increase and is associated with increased mortality and morbidity. It has been clearly shown that this adiposity is stored mainly in the form of triglycerides. In this context, it has been reported that transgenic mice overexpressing FGF19 (activator of FGFR4) have an increased metabolic rate associated with decreased adiposity (E. Tomlinson, Transgenic mice expressing human fibroblast growth factor-19 display increased metabolic rate and decreased adiposity. Endocrinology, 2002 May; 143(5): 1741-7). In addition, mice not expressing FGFR-4 showed an increased expression of bile acid associated with an increase in CYP7A1, an enzyme associated with the production of this acid. By virtue of their agonist activity on FGF receptors, and in particular FGFR4, the compounds of said invention could promote decreased cholesterol associated with a decrease in adiposity.

According to another of its aspects, a subject of the present invention is therefore the use of a compound as defined above, for the preparation of a medicament for use in the treatment of diseases requiring FGF receptor activation.

A subject of the present invention is more particularly the use of a compound as defined above, for the preparation of a medicament for use in the treatment of cardiac ischaemia, the treatment of diseases associated with narrowing or an obstruction of the arteries, or arteritis, the treatment of angina pectoris, the treatment of thromboangiitis obliterans, the treatment of atherosclerosis, treatment to inhibit post-angioplasty or post-endarterectomy restenosis, wound-healing treatment, treatment for muscle regeneration, treatment for myoblast survival, the treatment of nociception and the treatment of chronic pain, the treatment of peripheral neuropathy, treatment for improving bioartificial pancreatic graft survival in diabetic patients, treatment to bring about a decrease in cholesterol associated with a decrease in adiposity, treatment for improving graft revascularization and graft survival, the treatment of retinal degeneration, the treatment of pigmentary retinitis, the treatment of osteoarthritis, the treatment of pre-eclampsia, the treatment of vascular lesions and of acute respiratory distress syndrome, bone protection treatment, or treatment for hair follicle protection.

According to another of its aspects, a subject of the present invention is therefore a pharmaceutical composition containing, as active ingredient, a compound of formula $M_1$-L-$M_2$ according to the invention or one of its pharmaceutically acceptable salts, optionally in combination with one or more inert and suitable excipients.

Said excipients are selected according to the pharmaceutical form and the method of administration desired: oral, sublingual, subcutaneous, intramuscular, intravenous, transdermal, transmucosal, local or rectal.

The pharmaceutical compositions according to the present invention can be administered, in particular, orally, sublingually, subcutaneously, intramuscularly, intravenously, transdermally, transmucosally, locally or rectally.

In the pharmaceutical compositions of the present invention for oral administration, the active ingredients can be administered in unit administration forms, as a mixture with conventional pharmaceutical supports. The suitable unit administration forms comprise, for example, optionally scored tablets, gelatine capsules, powders, granules and oral solutions or suspensions.

When a solid composition in the form of tablets is prepared, the main active ingredient is mixed with a pharmaceutical carrier such as gelatine, starch, lactose, magnesium stearate, talc, gum arabic, or the like. The tablets can be coated with sucrose or with other suitable substances or else they can be treated such that they have a sustained or delayed activity and that they continuously release a predetermined amount of active ingredient.

A preparation of gelatine capsules is obtained by mixing the active ingredient with a diluent and pouring the mixture obtained into soft or hard gelatine capsules.

A preparation in the form of a syrup or of an elixir can contain the active ingredient together with a sweetener, preferably calorie-free, methylparaben and propylparaben as antiseptics, and also a flavouring and a suitable colourant.

The water-dispersible powders or granules can comprise the active ingredient as a mixture with dispersing agents, wetting agents or suspending agents, such as polyvinylpyrrolidone, along with sweeteners or flavour enhancers.

The active ingredient can also be formulated in the form of microcapsules, optionally with one or more supports or additives.

In the pharmaceutical compositions according to the present invention, the active ingredient can also be in the form of an inclusion complex in cyclodextrins, their ethers or their esters.

The amount of active ingredient to be administered depends, as always, on the degree of progression of the disease, on the age and weight of the patient and on the route of administration.

A subject of the present invention is a pharmaceutical composition as defined above, for use in the treatment of cardiac ischaemia, the treatment of diseases associated with narrowing or an obstruction of the arteries, or arteritis, the treatment of angina pectoris, the treatment of thromboangiitis obliterans, the treatment of atherosclerosis, treatment to inhibit post-angioplasty or post-endarterectomy restenosis, wound-healing treatment, treatment for muscle regeneration, treatment for myoblast survival, the treatment of nociception and the treatment of chronic pain, the treatment of peripheral neuropathy, treatment for improving bioartificial pancreatic graft survival in diabetic patients, treatment to bring about a decrease in cholesterol associated with a decrease in adiposity, treatment for improving graft revascularization and graft survival, the treatment of retinal degeneration, the treatment of pigmentary retinitis, the treatment of osteoarthritis, the treatment of pre-eclampsia, the treatment of vascular lesions and acute respiratory distress syndrome, bone protection treatment, or treatment for hair follicle protection.

Table of the examples:

$M_1$-L-$M_2$ with M of formula as below:

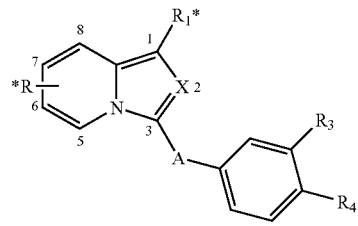

For the examples described below, A is a CO radical.

When R is defined as being an 8-O*, 6-O* radical, this means that R is a hydroxyl radical in the 8- or 6-position of the heterocycle. When R is defined as being a 7-CONH* radical, this means that R is an amido radical in the 7-position of the heterocycle.

| | | | | | | Homodimers | | |
|---|---|---|---|---|---|---|---|---|
| Ex | R | R1 | X | R3 | R4 | L | Salt | Mp (° C.) or MH+/RT (min) |
| 1 | 8-O* | OCH3 | CCH3 | CO2H | NH2 | —(CH2CH2O)6CH2CH2— | 2 Na, 1.5 H2O | 265° C. |
| 2 | 8-O* | OCH3 | CCH3 | CO2H | NH2 | —(CH2CH2O)5CH2CH2— | 2 Na, 3.6 H2O | 201° C. |
| 3 | 8-O* | OCH3 | CCH3 | CO2H | NH2 | —(CH2CH2O)4CH2CH2— | 2 Na, 5.45 H2O | 162° C. |
| 4 | 8-O* | OCH3 | CCH3 | CO2H | NH2 | —(CH2CH2O)3CH2CH2— | 2 Na, 4.8 H2O | 239° C. |
| 5 | 8-O* | OCH3 | CCH3 | CO2H | NH2 | —(CH2CH2O)2CH2CH2— | 2 Na, 2.5 H2O | 252° C. |
| 6 | 8-O* | OCH3 | CCH3 | CO2H | NH2 | —CH2OCH2OCH2— | 2 Na, 7.45 H2O | 258° C. |
| 7 | 8-O* | OCH3 | CCH3 | CO2H | NH2 | —CH2OCNH(CH2)11NHCOCH2— | 2 Na, 3.5 H2O | 220° C. |
| 8 | 8-O* | Ph-3-CO2H | N | —OCH3 | NH2 | —(CH2CH2O)5CH2CH2— | 2 Na, 5 H2O | 209° C. |
| 9 | 8-O* | 4-pyridine | N | —OCH3 | NH2 | —(CH2CH2O)5CH2CH2— | 2.4 HCl, 8.6 H2O | 184° C. |
| 10 | 8-O* | H | N | —OCH3 | NH2 | —(CH2CH2O)5CH2CH2— | 2 HCl, 5 H2O | 80° C. |
| 11 | 6-O* | OCH3 | CCH3 | CO2H | NH2 | —(CH2CH2O)6CH2CH2— | 2 Na, 7.4 H2O | 181° C. |
| 12 | 6-O* | OCH3 | CCH3 | CO2H | NH2 | —(CH2CH2O)5CH2CH2— | 2 Na, 6 H2O | 261-270° C. |
| 13 | 6-O* | OCH3 | CCH3 | CO2H | NH2 | —(CH2CH2O)4CH2CH2— | 2 Na, 5 H2O | 255-260° C. |
| 14 | 6-O* | OCH3 | CCH3 | CO2H | NH2 | —(CH2CH2O)3CH2CH2— | 2 Na, 5 H2O | 232° C. |
| 15 | 6-O* | OCH3 | CCH3 | CO2H | NH2 | —(CH2CH2O)2CH2CH2— | 2 Na, 6.95 H2O | 297-300° C. |
| 16 | 6-O* | OCH3 | CCH3 | CO2H | NH2 | —CH2OCH2OCH2— | 2 Na, 5 H2O | 294-300° C. |
| 17 | H | OCH3 | CPh-4-O* | CO2H | NH2 | —(CH2CH2O)6CH2CH2— | 2 Na, 7.5 H2O | 174° C. |
| 18 | H | OCH3 | CPh-4-O* | CO2H | NH2 | —(CH2CH2O)5CH2CH2— | 2 Na, 6.5 H2O | 168° C. |
| 19 | H | OCH3 | CPh-3-O* | CO2H | NH2 | —(CH2CH2O)6CH2CH2— | 2 Na, 2.65 H2O | 197° C. |
| 20 | H | OCH3 | CPh-3-O* | CO2H | NH2 | —(CH2CH2O)5CH2CH2— | 2 Na, 4.5 H2O | 198° C. |
| 21 | H | O* | CCH3 | CO2H | NH2 | —(CH2CH2O)6CH2CH2— | 2 Na, 5.5 H2O | 224° C. |
| 22 | H | O* | CCH3 | CO2H | NH2 | —(CH2CH2O)5CH2CH2— | 2 Na, 4 H2O | 165° C. |
| 23 | H | O* | CCH3 | CO2H | NH2 | —(CH2CH2O)4CH2CH2— | 2 Na, 4 H2O | 186° C. |
| 24 | H | O* | CCH3 | CO2H | NH2 | —(CH2CH2O)3CH2CH2— | 2 Na, 5 H2O | 226° C. |

-continued

Homodimers

| # | | | | | | Linker | Salt/Hydrate | mp |
|---|---|---|---|---|---|---|---|---|
| 25 | H | O* | CCH$_3$ | CO$_2$H | NH$_2$ | —(CH$_2$CH$_2$O)$_2$CH$_2$CH$_2$— | 2 Na, 4 H$_2$O | 244° C. |
| 26 | H | O* | CCH$_3$ | CO$_2$H | NH$_2$ | —CH$_2$CH$_2$OCH$_2$CH$_2$— | 2 Na, 4 H$_2$O | 277° C. |
| 27 | H | —OCH$_2$Ph-3-O* | CCH$_3$ | CO$_2$H | NH$_2$ | —(CH$_2$CH$_2$O)$_2$CH$_2$CH$_2$— | 2 Na, 2.65 H$_2$O | 188° C. |
| 28 | H | —OCH$_2$Ph-4-O* | CCH$_3$ | CO$_2$H | NH$_2$ | —(CH$_2$CH$_2$O)$_2$CH$_2$CH$_2$— | 2 Na, 3 H$_2$O | 247° C. |
| 29 | H | —OCH$_2$Ph-4-O* | CCH$_3$ | CO$_2$H | NH$_2$ | —(CH$_2$)$_8$— | 2 Na, 3.5 H$_2$O | 239° C. |
| 30 | H | —OCH$_2$Ph-3-O* | CCH$_3$ | CO$_2$H | NH$_2$ | —CH$_2$CONH(CH$_2$)$_2$NHCOCH$_2$— | 2 Na, 3 H$_2$O, +1 acetone | 296° C. |
| 31 | H | O* | CCH$_3$ | CO$_2$H | NH$_2$ | —CH$_2$CONH(CH$_2$)$_2$NHCOCH$_2$— | 2 Na, 3 H$_2$O | 320° C. |
| 32 | H | O* | CCH$_3$ | CO$_2$H | NH$_2$ | —CH$_2$CONH(CH$_2$)$_3$NHCOCH$_2$— | 2 Na, 5 H$_2$O | 264° C. |
| 33 | H | NH* | CCH$_3$ | CO$_2$H | NH$_2$ | —(CH$_2$CH$_2$O)$_4$CH$_2$CH$_2$— | 2 Na, 4 H$_2$O | 193° C. |
| 34 | H | —NHCOPh-3-O* | CCH$_3$ | CO$_2$H | NH$_2$ | —(CH$_2$)$_8$— | 2 Na, 5 H$_2$O +0.35 DMF | 263° C. |
| 35 | H | —NHCOPh-3-O* | CCH$_3$ | CO$_2$H | NH$_2$ | —(CH$_2$CH$_2$O)$_5$CH$_2$CH$_2$— | 2 Na, 5 H$_2$O +0.5 acetone | 252° C. |
| 36 | H | —NHCOPh-3-O* | CCH$_3$ | CO$_2$H | NH$_2$ | —(CH$_2$CH$_2$O)$_4$CH$_2$CH$_2$— | 2 Na, 5 H$_2$O +0.6 acetone | 267-269° C. |
| 37 | H | —NHCOPh-3-O* | CCH$_3$ | CO$_2$H | NH$_2$ | —(CH$_2$CH$_2$O)$_3$CH$_2$CH$_2$— | 2 Na, 4.95 H$_2$O | 312-314° C. |
| 38 | H | —NHCOPh-3-O* | CCH$_3$ | CO$_2$H | NH$_2$ | —(CH$_2$CH$_2$O)$_2$CH$_2$CH$_2$— | 2 Na, 5 H$_2$O +0.5 acetone | 300-310° C. |
| 39 | H | —NHCOPh-3-O* | CCH$_3$ | CO$_2$H | NH$_2$ | —CH$_2$CH$_2$OCH$_2$CH$_2$— | 2 Na, 5 H$_2$O +0.3 acetone | 334-337° C. |
| 40 | H | —NHCOPh-3-O* | CCH$_3$ | CO$_2$H | NH$_2$ | piperazine-1,4-diyl-bis(CH$_2$CH$_2$—) | 2 Na, 5 H$_2$O | 326-328° C. |

-continued

| | | | | | | Homodimers | | |
|---|---|---|---|---|---|---|---|---|
| 41 | H | —NHCOPh-3-O* | CCH$_3$ | CO$_2$H | NH$_2$ | ![structure with OMe, OCH$_2$CH$_2$— and —CH$_2$CH$_2$O— on benzene ring] | 2 Na, 5 H$_2$O +0.3 acetone | 257-259° C. |
| 42 | H | —NHCOPh-3-O* | CCH$_3$ | CO$_2$H | NH$_2$ | —CH$_2$NHCO—(CH$_2$)$_2$CONHCH$_2$— | 2 Na, 5 H$_2$O | 355-361° C. |
| 43 | H | —NHCOPh-3-O* | CCH$_3$ | CO$_2$H | NH$_2$ | —CH$_2$CH$_2$NHCONHCH$_2$CH$_2$— | 2 Na, 4 H$_2$O | 354-359° C. |
| 44 | H | —NHCOPh-3-O* | CCH$_3$ | CO$_2$H | NH$_2$ | —CH$_2$CONH(CH$_2$)$_2$NHCOCH$_2$— | 2 Na, 5 H$_2$O | 339-354° C. |
| 45 | H | —NHCOPh-3-O* | CCH$_3$ | CO$_2$H | NH$_2$ | —CH$_2$CONH(CH$_2$)$_3$NHCOCH$_2$— | 2 Na, 4 H$_2$O | 358-360° C. |
| 46 | H | —NHCOPh-3-O* | CCH$_3$ | CO$_2$H | NH$_2$ | —CH$_2$CONH(CH$_2$)$_4$NHCOCH$_2$— | 2 Na, 5 H$_2$O | 343° C. |
| 47 | H | —NHCOPh-3-O* | CCH$_3$ | CO$_2$H | NH$_2$ | —CH$_2$CO—[piperazine-N,N']—COCH$_2$— | 2 Na, 6 H$_2$O | 346-357° C. |
| 48 | 7-CONH* | —Ph-3-CO$_2$H | N | OCH$_3$ | NH$_2$ | —CH$_2$CH$_2$CH$_2$(OCH$_2$CH$_2$)$_4$OCH$_2$CH$_2$CH$_2$— | 2 Na, 8 H$_2$O | 290-293° C. |
| 49 | 7-CONH* | —Ph-3-CO$_2$H | N | OCH$_3$ | NH$_2$ | —CH$_2$CH$_2$CH$_2$(OCH$_2$CH$_2$)$_2$OCH$_2$CH$_2$CH$_2$— | 2 Na, 8.5 H$_2$O 0.2 acetone | 213° C. |
| 50 | 7-CO$_2$H | —Ph-3-CONH* | N | OCH$_3$ | NH$_2$ | —(CH$_2$)$_9$— | 2 Na, 4.5 H$_2$O | 348-355° C. |
| 51 | H | —NHCOPh-3-O* | CCH$_3$ | CO$_2$H | NH$_2$ | —(CH$_2$)$_7$— | 2 Na, 6.35 H$_2$O | 286° C. |
| 52 | H | —NHCOPh-3-O* | N | CO$_2$H | NH$_2$ | —(CH$_2$)$_8$— | 2 Na, 4.95 H$_2$O | 249° C. |
| 53 | H | —NHCOPh-3-O* | N | CO$_2$H | NH$_2$ | —CH$_2$CONH(CH$_2$)$_2$NHCOCH$_2$— | 2 Na, 7.5 H$_2$O | 281-286° C. |
| 54 | 7-CO$_2$H | —NHCOPh-3-O* | N | OCH$_3$ | NH$_2$ | —(CH$_2$)$_8$— | 2 Lys | RT = 15.34 min (Method A) |
| 55 | H | —NHCOPh-4-O* | CCH$_3$ | OCH$_3$ | NH$_2$ | —CH$_2$CONH(CH$_2$)$_2$NHCOCH$_2$— | 2 HCl | 223° C. |
| 56 | H | —NHCOPh-3-O* | CCH$_3$ | OCH$_3$ | NH$_2$ | —CH$_2$CONHCH$_2$CH(NMe$_2$)CH$_2$—NHCOCH$_2$— | 2 HCl | 183° C. |
| 57 | H | —NHCOPh-3-O* | CCH$_3$ | OCH$_3$ | NH$_2$ | —CH$_2$CONHCH$_2$CH(CH$_2$NMe$_2$)—CH$_2$NHCOCH$_2$— | 3 HCl 4.5 H$_2$O | 194° C. |
| 58 | H | —NHCOPh-3-O* | CCH$_3$ | OCH$_3$ | NH$_2$ | —CH$_2$CONHCH$_2$CH(OH)—CH$_2$NHCOCH$_2$— | 2 HCl 7.5 H$_2$O | 202° C. |
| 59 | H | —NHCOPh-3-O* | CCH$_3$ | OCH$_3$ | NH$_2$ | —CH$_2$CH$_2$N(Me)CH$_2$N(Me)CH$_2$CH$_2$— | 2 HCl 7 H$_2$O | 238° C. |
| 60 | H | —NHCOPh-3-O* | CCH$_3$ | OCH$_3$ | NH$_2$ | —CH$_2$CH$_2$N(Bn)CH$_2$CH$_2$N(Bn)CH$_2$CH$_2$— | 2 HCl 1.5 acetone | 217° C. |
| 61 | H | —NHCOPh-4-O* | CCH$_3$ | OCH$_3$ | NH$_2$ | —CH$_2$CH$_2$N(Me)CH$_2$CH$_2$N(Me)CH$_2$CH$_2$— | 2 HCl 6.95 H$_2$O 8 H$_2$O | 215° C. |

-continued

Homodimers

| # | | R' | R'' | R''' | R'''' | Linker | Salt/Hydrate | mp |
|---|---|---|---|---|---|---|---|---|
| 62 | H | —NHCOPh-3-O* | CCH₃ | OCH₃ | NH₂ | [3,4-dioxocyclobut-1,2-diyl bis(NHCH₂CH₂)] linker | 2 HCl | 217° C. |
| 63 | H | —NHCOPh-3-O* | CCH₃ | OCH₃ | NH₂ | —CH₂CH₂NHCOCONHCH₂CH₂— | — | 225° C. |
| 64 | H | —NHCOPh-4-O* | CCH₃ | CO₂H | NH₂ | —CH₂CONH(CH₂)₂NHCOCH₂— | 2 Na, 5 H₂O | 290-297° C. |
| 65 | H | —NHCOPh-4-O* | CCH₃ | CO₂H | NH₂ | —CH₂CON(CH₃)CH₂CH₂N(CH₃)COCH₂— | 2 Na, 11 H₂O | 296-300° C. |
| 66 | H | —NHCOPh-4-O* | CCH₃ | CO₂H | NH₂ | —(CH₂CH₂O)₃CH₂CH₂— | 2 Na, 7 H₂O | 292-294° C. |
| 67 | H | —NHCOPh-4-O* | CCH₃ | CO₂H | NH₂ | —(CH₂CH₂O)₂CH₂CH₂— | 2 Na, 4.5 H₂O | 308-310° C. |
| 68 | H | —NHCOPh-4-O* | CCH₃ | CO₂H | NH₂ | —CH₂CH₂OCH₂CH₂— | 2 Na, 5 H₂O | 320-322° C. |
| 69 | H | —NHCOPh-4-O* | CCH₃ | CO₂H | NH₂ | —(CH₂)₃— | 2 Na, 7.5 H₂O | 283° C. |
| 70 | H | —NHCOPh-4-O* | CCH₃ | CO₂H | H | —(CH₂)₂— | 2 Na | 306° C. |
| 71 | H | —NHCOPh-3-O* | CCH₃ | CO₂H | NH₂ | —CH₂CONH(CH₂)₂NHCOCH₂— | 2 Na, 4.95 H₂O | 330-339° C. |
| 72 | H | —NHCOPh-3-O* | CCH₃ | CO₂H | NH₂ | [benzene-1,3-disulfonamide: —CH₂CH₂NH—SO₂-(m-C₆H₄)-SO₂—NHCH₂CH₂—] | 2 Na, 4.2 H₂O; 2 Na, 8 H₂O | 308° C. |
| 73 | H | —NHCOPh-3-O* | CCH₃ | CO₂H | NH₂ | —CH₂CH₂NHCOCH₂CONH—CH₂CH₂— | 2 Na, 7 H₂O | 289° C. |
| 74 | H | —NHCOPh-3-O* | CCH₃ | CO₂H | NH₂ | [terephthaloyl bis(NHCH₂CH₂)] linker | 2 Lys, 6 H₂O | 224° C. |
| 75 | H | —NHCOPh-3-O* | CCH₃ | CO₂H | NH₂ | [pyridine-3,5-dicarboxamido bis(NHCH₂CH₂)] linker | 2 Lys, 8 H₂O | 214° C. |
| 76 | H | —NHCOPh-3-O* | CCH₃ | CO₂H | NH₂ | —CH₂CON(Me)CH₂CH₂—N(Me)COCH₂— | 2 Lys | MH+ = 1027, RT = 11.22 min (Method A) |

| # | | | | | | Homodimers | | |
|---|---|---|---|---|---|---|---|---|
| 77 | H | —NHCOPh-3-O* | CCH$_3$ | CO$_2$H | NH$_2$ | | 2 Na 6.5 H$_2$O | 305° C. |
| 78 | H | —NHCOPh-3-O* | CCH$_3$ | CO$_2$H | NH$_2$ | —H$_2$COC—N(H)—(cyclopropyl)—N(H)—COCH$_2$— | 2 Na 7.5 H$_2$O | 297° C. |
| 79 | H | —NHCOPh-3-O* | CCH$_3$ | CO$_2$H | NH$_2$ | —CH$_2$CONHCH$_2$NHCOCH$_2$— | 2 Lys 10 H$_2$O | 209° C. |
| 80 | H | —NHCOPh-3-O* | CCH$_3$ | CO$_2$H | NH$_2$ | —CH$_2$CH$_2$N(Me)CH$_2$N(Me)CH$_2$CH$_2$— | 2 Lys 9 H$_2$O | 198° C. |
| 81 | H | NHCO* | CCH$_3$ | CO$_2$H | NH$_2$ | —CH$_2$CH$_2$CON(CH$_3$)CH$_2$CH$_2$N(CH$_3$)COCH$_2$CH$_2$— | 2 Lys | MH$^+$ = 871.43 RT = 1.24 min (Method B) |
| 82 | H | NHCO* | CCH$_3$ | CO$_2$H | NH$_2$ | —CH$_2$CH$_2$CON(CH$_3$)CH$_2$CH$_2$CH$_2$(OCH$_2$CH$_2$)$_2$N(CH$_3$)COCH$_2$CH$_2$— | 2 Lys | MH+ = 959.51 RT = 1.30 min (Method B) |
| 83 | H | NHCO* | CCH$_3$ | CO$_2$H | NH$_2$ | —CH$_2$CH$_2$CON(CH$_3$)CH$_2$CH$_2$OCH$_2$CH$_2$N(CH$_3$)COCH$_2$CH$_2$— | 2 Lys | MH+ = 915.46 RT = 1.28 min (Method B) |
| 84 | H | NHCO* | CCH$_3$ | CO$_2$H | NH$_2$ | —(CH$_2$)$_2$OC—N(homopiperazine)N—CO(CH$_2$)$_2$— | 2 Lys | MH+ = 883.45 RT = 1.26 min (Method B) |
| 85 | H | NHCO* | CCH$_3$ | CO$_2$H | NH$_2$ | —CH$_2$CH$_2$CON(CH$_3$)(CH$_2$)$_8$N(CH$_3$)COCH$_2$CH$_2$— | 2 Lys | MH+ = 955.54 RT = 1.50 min (Method B) |
| 86 | H | NHCO* | CCH$_3$ | CO$_2$H | NH$_2$ | —CH$_2$CH$_2$CON(CH$_3$)CH$_2$CH$_2$N(CH$_3$)COCH$_2$CH$_2$— | 2 Lys | MH+ = 885.50 RT = 1.49 min (Method B) |
| 87 | H | NHCO* | CCH$_3$ | CO$_2$H | NH$_2$ | —(CH$_2$)$_3$CON(CH$_3$)CH$_2$CH$_2$CH$_2$(OCH$_2$CH$_2$)$_2$N(CH$_3$)CO(CH$_2$)$_3$— | 2 Lys | MH+ = 987.58 RT = 1.32 min (Method B) |
| 88 | H | NHCO* | CCH$_3$ | CO$_2$H | NH$_2$ | —(CH$_2$)$_3$CON(CH$_3$)(CH$_2$)$_8$N(CH$_3$)CO(CH$_2$)$_3$— | 2 Lys | MH+ = 983.62 RT = 1.47 min (Method B) |
| 89 | H | NHCO* | CCH$_3$ | CO$_2$H | NH$_2$ | —(CH$_2$)$_3$CON(CH$_3$)(CH$_2$)$_6$N(CH$_3$)CO(CH$_2$)$_3$— | 2 Lys | MH+ = 955.58 RT = 1.39 min (Method B) |
| 90 | H | NHCO* | CCH$_3$ | CO$_2$H | NH$_2$ | —(CH$_2$)$_3$CON(CH$_3$)CH$_2$CH$_2$OCH$_2$CH$_2$N(CH$_3$)CO(CH$_2$)$_3$— | 2 Lys | MH+ = 943.51 RT = 1.35 min (Method B) |
| 91 | H | NHCO* | CCH$_3$ | CO$_2$H | NH$_2$ | —(CH$_2$)$_3$CON(CH$_3$)(CH$_2$)$_2$N(CH$_3$)CO(CH$_2$)$_3$— | 2 Lys | MH+ = 899.52 RT = 1.32 min (Method B) |

-continued

| | | | | | Homodimers | | |
|---|---|---|---|---|---|---|---|
| 92 | H | NHCO* | CCH₃ | CO₂H | NH₂ | —(CH₂)₃OC—[7-membered N,N ring]—CO(CH₂)₃— | MH+ = 911.48 RT = 1.29 min (Method B) |
| 93 | H | NHCO* | CCH₃ | CO₂H | NH₂ | —CH₂OCH₂CON(CH₃)CH₂CH₂(OCH₂CH₂)₂N(CH₃)COCH₂OCH₂— | MH+ = 991.54 RT = 1.33 min (Method B) |
| 94 | H | NHCO* | CCH₃ | CO₂H | NH₂ | —CH₂OCH₂CON(CH₃)(CH₂)₈N(CH₃)COCH₂OCH₂— | MH+ = 987.53 RT = 1.50 min (Method B) |
| 95 | H | NHCO* | CCH₃ | CO₂H | NH₂ | —CH₂OCH₂CON(CH₃)(CH₂)₆N(CH₃)COCH₂OCH₂— | MH+ = 959.50 RT = 1.40 min (Method B) |
| 96 | H | NHCO* | CCH₃ | CO₂H | NH₂ | —CH₂OCH₂CON(CH₃)(CH₂)₃N(CH₃)COCH₂OCH₂— | MH+ = 917.57 RT = 1.43 min (Method B) |
| 97 | H | NHCO* | CCH₃ | CO₂H | NH₂ | —(CH₂)₃CO—[piperazine]—CO(CH₂)₃— | MH+ = 897.35 RT = 1.36 min (Method B) |
| 98 | H | NHCO* | CCH₃ | CO₂H | NH₂ | —CH₂OCH₂CO—[piperazine]—COCH₂OCH₂— | MH+ = 901.54 RT = 1.43 min (Method B) |
| 99 | H | NHCO* | CCH₃ | CO₂H | NH₂ | —(CH₂)₄CON(CH₃)(CH₂)₃N(CH₃)CO(CH₂)₄— | MH+ = 941.65 RT = 1.53 min (Method B) |
| 100 | H | NHCO* | CCH₃ | CO₂H | NH₂ | —(CH₂)₂CON(CH₃)(CH₂)₆N(CH₃)CO(CH₂)₂— | MH+ = 926.17 RT = 1.73 min (Method C) |
| 101 | H | NHCO* | CCH₃ | CO₂H | NH₂ | —CH₂OCH₂CON(CH₃)CH₂CH₂—OCH₂CH₂N(CH₃)COCH₂OCH₂— | MH+ = 947.37 RT = 1.33 min (Method B) |
| 102 | H | NHCO* | CCH₃ | CO₂H | NH₂ | —(CH₂)₄CON(CH₃)(CH₂)₂N(CH₃)CO(CH₂)₄— | MH+ = 927.63 RT = 1.45 min (Method B) |
| 103 | H | NHCO* | CCH₃ | CO₂H | NH₂ | —(CH₂)₃CON(CH₃)(CH₂)₃N(CH₃)CO(CH₂)₃— | MH+ = 913.61 RT = 1.45 min (Method B) |
| 104 | H | NHCO* | CCH₃ | CO₂H | NH₂ | —CH₂OCH₂CON(CH₃)CH₂CH₂—N(CH₃)COCH₂OCH₂— | MH+ = 903.56 RT = 1.38 min (Method B) |
| 105 | —NHCOPh-3-O* | CCH₃ | CO₂H | NH₂ | | —CH₂CONHCH₂CONHCH₂CH₂— | 2 Na, 6.2 H₂O 313-318° C. |

-continued

Homodimers

| Ex | R | $R_1$ | X | $R_3$ | $R_4$ | L | Salt | Mp (° C.) |
|---|---|---|---|---|---|---|---|---|
| 106 | H | —Ph-4-O* | $CCH_3$ | $CO_2H$ | $NH_2$ | —$(CH_2CH_2O)_2CH_2CH_2$— | 2 Na, 4 $H_2O$ | 257° C. |
| 107 | H | —Ph-4-O* | $CCH_3$ | $CO_2H$ | $NH_2$ | —$(CH_2CH_2O)_3CH_2CH_2$— | 2 Na, 4 $H_2O$ | 245° C. |
| 108 | H | —Ph-3-O* | $CCH_3$ | $CO_2H$ | $NH_2$ | —$(CH_2CH_2O)_2CH_2CH_2$— | 2 Na, 4 $H_2O$ | 258° C. |
| 109 | H | —Ph-3-O* | $CCH_3$ | $CO_2H$ | $NH_2$ | —$(CH_2CH_2O)_3CH_2CH_2$— | 2 Na, 2.5 $H_2O$ | 236° C. |
| 110 | H | —Ph-3-O* | $CCH_3$ | $CO_2H$ | $NH_2$ | —$CH_2CONH(CH_2)_2NHCOCH_2$— | 2 Na, 4 $H_2O$ | 237° C. |
| 111 | H | —Ph-3-O* | $CCH_3$ | $CO_2H$ | $NH_2$ | —$CH_2CONH(CH_2)_6NHCOCH_2$— | 2 Na, 5 $H_2O$ | 224° C. |
| 112 | H | —Ph-4-O* | $CCH_3$ | $CO_2H$ | $NH_2$ | —$CH_2CONH(CH_2)_6NHCOCH_2$— | 2 Na, 3 $H_2O$ | 241° C. |
| 113 | H | —Ph-4-O* | $CCH_3$ | $CO_2H$ | $NH_2$ | —$CH_2CONH(CH_2)_2NHCOCH_2$— | 2 Na, 6 $H_2O$ | 279° C. |
| 114 | 6-$OCH_2$—$CH_2NH^*$ | $OCH_3$ | $CCH_3$ | $CO_2H$ | $NH_2$ | —$COCH_2OCH_2CONHCH_2$—$CH_2NHCOCH_2OCH_2CO$— | 2 Lys | MH = 1023.41 RT = 1.44 min (Method B) |
| 115 | 6-$OCH_2$—$CH_2NH^*$ | $OCH_3$ | $CCH_3$ | $CO_2H$ | $NH_2$ | —$COCH_2OCH_2CONHCH_2CH_2CH_2NHCOCH_2OCH_2CO$— | 2 Lys | MH+ = 1067.42 RT = 1.48 min (Method B) |

| Ex | R | $R_1$ | X | $R_3$ | $R_4$ | L | Salt | Mp (° C.) |
|---|---|---|---|---|---|---|---|---|
| 116 | 6-$OCH_2$—$CH_2NH^*$ | $OCH_3$ | $CCH_3$ | $CO_2H$ | $NH_2$ | —$COCH_2OCH_2CONH(CH_2CH_2O)_2$—$CH_2CH_2NHCOCH_2OCH_2OC$— | 2 Lys | MH+ = 1111.46 RT = 1.46 min (Method B) |
| 117 | H | —NHCOPh-3-O* | $CCH_3$ | $CO_2H$ | $NH_2$ | —$CH_2CONH(CH_2)_2NHCOCH_2$— | 2 Na, 6 $H_2O$ | 278° C. |
| | H | —NHCOPh-3-O* | N | $CO_2H$ | $NH_2$ | | | |
| 118 | H | —NHCOPh-3-O* | $CCH_3$ | $CO_2H$ | $NH_2$ | —$CH_2CONH(CH_2)_2NHCOCH_2$— | 2 Lys, 9.5 $H_2O$ | 213° C. |
| | H | —NHCOPh-4-O* | $CCH_3$ | $CO_2H$ | $NH_2$ | | | |
| 119 | H | —O* | $CCH_3$ | $CO_2H$ | $NH_2$ | —$(CH_2CH_2O)_6CH_2CH_2$— | 2 Na, 4.5 $H_2O$ | 280° C. |
| | 8-O* | $OCH_3$ | $CCH_3$ | $CO_2H$ | $NH_2$ | | | |
| 120 | 8-O* | $OCH_3$ | $CCH_3$ | $CO_2H$ | $NH_2$ | —$(CH_2CH_2O)_6CH_2CH_2$— | 2 Na, 6.4 $H_2O$ 0.1 acetone | 274° C. |
| | 6-O* | $OCH_3$ | $CCH_3$ | $CO_2H$ | $NH_2$ | | | |
| 121 | H | —O* | $CCH_3$ | $CO_2H$ | $NH_2$ | —$(CH_2CH_2O)_6CH_2CH_2$— | 2 Na, 8 $H_2O$ | 196° C. |
| | H | $OCH_3$ | CPh-4-O* | $CO_2H$ | $NH_2$ | | | |

The following examples, given in a nonlimiting manner, illustrate the present invention.

In the following text:

The mass spectra were recorded on chromatography apparatus (Waters Alliance 2695, PDA detector), coupled to a mass spectrometer (Waters Z Q or Waters T of). The chromatographic separations are carried out in C18 reverse-phase at pH=7 or at pH=3. The products detected by mass spectrometry are ionized in the positive electrospray mode (ES+).

The products characterized in terms of their mass (MH$^+$) and their retention time (RT) were analysed either by:

Method A: the mass spectra were recorded on a chromatography apparatus (Agilent series 1100) coupled to a mass spectrometer (MSD Agilent series 1100). The chromatographic separations are carried out in C18 reverse-phase at pH=7 according to the following conditions:

Column: X terra MS C18 (2.1×50 mm) 3.5 μm
Eluent A: ammonium acetate buffer, pH=7.0 (10 mM)>
Eluent B: acetonitrile
Gradient: 0% to 90% of B in 30 min
Flow rate: 0.4 ml/min
Injection: 2 μl—solution at 0.5 mg/ml in DMSO
UV detection: 220 nm
Column temperature: 30° C.

The products detected by mass spectrometry are ionized in the positive electrospray mode (ES+).

Method B: the mass spectra were recorded on a chromatography apparatus (Waters 1525) coupled to a mass spectrometer (Waters LCT electrospray time-of-flight mass spectrometer). The chromatographic separations are carried out in C18 reverse-phase according to the following conditions:

Column: YMC-Pack J'Sphere ODS H80, (33×2.1 mm) 4 μm, 80 A
Eluent A: 0.05% aqueous trifluoroacetic acid
Eluent B: 0.05% trifluoroacetic acid in acetonitrile
Gradient: 5% B to 95% B in 3.4 minutes
Flow rate: 1 ml/min
Injection: 1 μl (solution at 10 mM in DMSO)>
UV detection: 220 and 254 nm
Column temperature: ambient temperature.

The products detected by mass spectrometry are ionized in the positive electrospray mode (ES+).

Method C: the mass spectra were recorded on a chromatography apparatus (Waters 2795) coupled to a mass spectrometer (Electrospray quadrupole mass spectrometer (Waters Ultima)). The chromatographic separations are carried out in C18 reverse-phase according to the following conditions:

Column: YMC-Pack J'Sphere ODS H80, (33×2.1 mm) 4 μm, 80 A
Eluent A: 0.1% aqueous formic acid
Eluent B: 0.08% formic acid in acetonitrile
Gradient: 5% B to 95% B in 2.5 minutes
Flow rate: 1.3 ml/min
Injection: 20 μl (solution at 2 mM in DMSO)>
UV detection: 220 and 254 nm
Column temperature: ambient temperature.

The products detected by mass spectrometry are ionized in the positive electrospray mode (ES+).

Method D: the mass spectra were recorded on a chromatography apparatus (Agilent series 1100) coupled to a mass spectrometer (MSD Agilent series 1100). The chromatographic separations are carried out in C18 reverse-phase according to the following conditions:

Column: YMC-Pack J'Sphere ODS H80, (20×2.1 mm) 4 μm
Eluent A: 0.05% aqueous trifluoroacetic acid
Eluent B: acetonitrile
Gradient: 96% A to 95% B in 2 minutes, 95% B up to 2.40 min then 96% A up to 2.45 min
Flow rate: 1 ml/min
Injection: 2 μl—solution at 0.5 mg/ml in DMSO
UV detection: DAD 220, 254, 324 nm
Column temperature: 30° C.

The products detected by mass spectrometry are ionized in the positive electrospray mode (ES+).

The melting points are determined on the Büchi B-540 device.

The proton NMR spectra were recorded using a Bruker Avance 250 and Bruker Avance 400 spectrometer. The chemical shifts are expressed in ppm relative to DMSO used as internal reference. The abbreviations used for the multiplicity of the signals are, respectively: s, d, t, q and m for singlet, doublet, triplet, quadruplet and multiplet. The $^1$H-NMR spectra are determined in (CD$_3$)$_2$SO.

The flash chromatography purifications were carried out using Merck silica 60 (15-40 μm). The steric exclusion chromatography purifications were carried out using Sephadex™ LH20 gel, Amersham Biosciences.

EXAMPLE 1

Disodium salt of 3,3'-{3,6,9,12,15,18-hexaoxa-icosane-1,20-diylbis[oxy(1-methoxy-2-methyl-indolizine-8,3-diyl)carbonyl]}bis(6-aminobenzoic acid)

Stage A: 3-(Benzyloxy)-2-(chloromethyl)pyridine 25.2 ml of thionyl chloride are added to the solution of 40 g (0.19 mol) of 3-(benzyloxy)-2-(hydroxymethyl)pyridine (CAS 6059-29-6; Desideri, N; Sestili, I; Manarini, S; Cerletti, C; Stein; *Eur. J. Med. Chem. Chim. Ther.;* 26 (4) 1991; 455-460) in 265 ml of dichloromethane. The solution is stirred at ambient temperature under nitrogen, and then concentrated to dryness. The residue obtained is dissolved in water. Sodium bicarbonate is added until a solution at neutral pH is obtained. The aqueous solution is extracted with ethyl acetate. The organic phase is washed with a saturated aqueous solution of sodium chloride, dried over anhydrous sodium sulphate, and then concentrated to dryness. 41 g (95%) of a brown oil are obtained.

MH$^+$=234.2

Stage B: 3-(Benzyloxy)-2-(methoxymethyl)pyridine

The solution of 41 g (0.18 mol) of 3-(benzyloxy)-2-(chloromethyl)pyridine in 100 ml of methanol is added to the solution of sodium methoxide, prepared by adding 5.2 g (0.23 mol) of sodium to 150 ml of methanol. After refluxing for 3 hours under nitrogen, the solution is concentrated to dryness. The oil obtained is taken up in water and extracted with ethyl acetate. The organic solution is washed with a saturated aqueous solution of sodium chloride, dried over anhydrous sodium sulphate, and then concentrated to dryness. 39 g (97%) of a brown oil are obtained.

1H-NMR [(CD$_3$)$_2$SO, 250 MHz]: 8.15 (1H, d), 7.30-07.55 (7H, m), 5.22 (2H, s), 4.55 (2H, s), 3.31 (3H, s).

Stage C:
8-(Benzyloxy)-1-methoxy-2-methylindolizine

The mixture of 17.2 g (75.0 mmol) of 3-(benzyloxy)-2-(methoxymethyl)pyridine, 17.4 g (0.19 mol) of chloroacetone and 16.3 g (0.19 mol) of lithium bromide in 140 ml of acetonitrile is refluxed for 24 hours. The reaction medium is poured into water and the aqueous phase is washed twice with ethyl acetate. The aqueous phase is concentrated to dryness to give 22.9 g of a brown oil.

29 ml (0.19 mol) of triethylamine are added to the solution of quaternized pyridine in 260 ml of acetonitrile that has been refluxed. The solution is refluxed for 3 hours and then concentrated to dryness. The residue is taken up in water and extracted with ethyl acetate. The organic phase is washed with a saturated aqueous solution of sodium chloride, dried over sodium sulphate, and concentrated under reduced pressure. 14.3 g of a green oil are obtained, which oil is used as it is in the acylation stage.

MH+=268.2.

Stage D: Methyl 5-{[8-(Benzyloxy)-1-methoxy-2-methylindolizin-3-yl]carbonyl}-2-[(trifluoroacetyl)amino]benzoate 4.4 ml (54.3 mmol) of pyridine and then 15.0 g (48.4 mmol) of methyl 5-(chlorocarbonyl)-2-[(trifluoro-acetyl)amino]benzoate (described in Patent Application WO2003084956) are added, under argon, to the solution of 13.2 g (49.4 mmol) of 8-(benzyloxy)-1-methoxy-2-methylindolizine in 165 ml of dichloromethane. The reaction medium is stirred at ambient temperature for 3 hours. This is diluted with dichloromethane and this organic solution is washed with a saturated aqueous solution of sodium bicarbonate and then a saturated aqueous solution of sodium chloride, and dried over sodium sulphate. After concentration under reduced pressure, the solid obtained is taken up in ethanol, filtered and washed with ethanol, to give 16.2 g (61%) of an orange powder.

MH$^+$=541.5; melting point: 214° C.

Stage E: Methyl 2-amino-5-{[8-(benzyloxy)-1-methoxy-2-methylindolizin-3-yl]carbonyl}benzoate 1.15 g (8.33 mmol) of potassium carbonate are added to the solution of 0.90 g (1.67 mmol) of methyl 5-{[8-(benzyloxy)-1-methoxy-2-methylindolizin-3-yl]carbonyl}-2-[(trifluoroacetyl)amino]benzoate in 100 ml of methanol and 100 ml of dichloromethane. The mixture is stirred at ambient temperature for 20 hours. The yellow precipitate formed is filtered, washed thoroughly with water and dried, to give 0.61 g (83%) of a yellow powder.

MH$^+$=445.5; melting point: 174° C.

Stage F: Methyl 2-amino-5-[(8-hydroxy-1-methoxy-2-methylindolizin-3-yl)carbonyl]benzoate The mixture of 2.0 g (4.5 mmol) of methyl 2-amino-5-{[8-(benzyloxy)-1-methoxy-2-methylindolizin-3-yl]carbonyl}benzoate and 0.42 g (6.75 mmol) of ammonium formate in the presence of 1.0 g of palladium-on-charcoal (10%) in 20 ml of N,N-dimethylformamide is stirred for 12 hours at ambient temperature under argon. The mixture is filtered under nitrogen and concentrated to dryness so as to obtain 1.51 g of a red oil. The product decomposes on contact with air.

MH+=355.3.

Stage G: 3,3'-{3,6,9,12,15,18-hexaoxaicosane-1,20-diylbis[oxy(1-methoxy-2-methylindolizine-8,3-diyl)carbonyl]}bis(methyl 6-aminobenzoate)

8.0 ml (4.02 mmol) of potassium hexamethyldisilylamide (0.5 M solution in toluene) are added dropwise, at −20° C. under argon, to the solution of 1.30 g (3.66 mmol) of methyl 2-amino-5-[(8-hydroxy-1-methoxy-2-methylindolizin-3-yl)carbonyl]benzoate in 12 ml of tetrahydrofuran. The formation of a red precipitate is observed. The mixture is allowed to return to ambient temperature and 6 ml of N,N-dimethylformamide are added, followed by 1.0 g (1.83 mmol) of 1,20-diiodo-3,6,9,12,15,18-hexaoxaicosane (Example R1). The solution is stirred at 40° C. for 18 hours. The reaction medium is poured into a solution of hydrochloric acid (1 M) and the product is extracted with ethyl acetate. The organic phase is washed with a saturated aqueous solution of sodium chloride, dried over sodium sulphate, and concentrated under reduced pressure. The residue obtained is purified by flash chromatography on silica gel (dichloromethane). 0.92 g (50%) of a green solid is obtained.

MH$^+$=999.8; melting point: 199° C.

Stage H: Disodium salt of 3,3'-{3,6,9,12,15,18-hexaoxaicosane-1,20-diylbis[oxy(1-methoxy-2-methylindolizine-8,3-diyl)carbonyl]}bis(6-aminobenzoic acid)

1.35 ml of sodium hydroxide (1 M) are added to the solution of 0.45 g (0.45 mmol) of the dimer obtained in stage E above in 4.5 ml of 1-methyl-2-pyrrolidinone. The solution is stirred at ambient temperature for 2 hours. The reaction medium is poured into 150 ml of acetone. The yellow precipitate is filtered and dried, to give 356 mg of a yellow powder (disodium salt, 1.5H$_2$O).

Melting point: 265° C. $^1$H-NMR [(CD$_3$)$_2$SO, 250 MHz]: 8.61 (2H, d), 8.15 (2H, d), 7.30-8.00 (4H, broad s), 7.36 (2H, d), 6.53-6.61 (4H, m), 6.38 (2H, dd), 4.20-4.25 (4H, m), 3.83-3.87 (4H, m), 3.78 (6H, s), 3.63-3.67 (4H, m), 3.47-3.57 (16H, m), 1.94 (6H, s).

EXAMPLES 2 TO 6

By following the processes described in Stages G and H of Example 1, Examples 2 to 6 are prepared by dimerization of methyl 2-amino-5-[(8-hydroxy-1-methoxy-2-methylindolizin-3-yl)carbonyl]benzoate (Stage F of Example 1) with the appropriate diiodinated derivatives (Examples R2 to R6).

EXAMPLE 7

Disodium salt of 3,3'-{undecane-1,11-diylbis[imino(2-oxoethane-2,1-diyl)oxy(1-methoxy-2-methylindolizine-8,3-diyl)carbonyl]}bis(6-aminobenzoic acid)

Stage A: Methyl 2-amino-5-{[8-(2-tert-butoxy-2-oxoethoxy)-1-methoxy-2-methylindolizin-3-yl]carbonyl}benzoate 5.4 ml (9.31 mmol) of potassium hexamethyldisilylamide (0.5 M solution in toluene) and then 0.69 ml (4.66 mmol) of tert-butyl 2-bromoacetate are added, dropwise, to the solution of 1.50 g (4.23 mmol) of methyl 2-amino-5-[(8-hydroxy-1-methoxy-2-methylindolizin-3-yl)carbonyl]benzoate (Stage F of Example 1) in 15 ml of tetrahydrofuran at −20° C. under argon. The mixture is stirred for 2 hours, allowing it to return to ambient temperature. The reaction medium is poured into a saturated aqueous solution of potassium hydrogen sulphate and the mixture is extracted with ethyl acetate. The organic phase is washed with a saturated aqueous solution of sodium chloride, dried over sodium sulphate, and concentrated under reduced pressure. The oil obtained is purified by flash chromatography on silica gel (dichloromethane/methanol gradient=100/0 to 90/10). 1.26 g (64%) of a yellow powder are obtained.

$MH^+$=469.5; melting point: 188° C.

Stage B: ({3-[4-Amino-3-(methoxycarbonyl)benzoyl]-1-methoxy-2-methylindolizin-8-yl}oxy)acetic acid The solution of 0.68 g (1.45 mmol) of methyl 2-amino-5-{[8-(2-tert-butoxy-2-oxoethoxy)-1-methoxy-2-methylindolizin-3-yl]carbonyl}benzoate in 4.44 ml of trifluoroacetic acid and 7 ml of dichloromethane is stirred. After stirring at ambient temperature for 48 hours, the reaction medium is concentrated to dryness and the red solid obtained is taken up in ethyl ether. The solid in suspension is filtered and is dried at 50° C. under vacuum so as to obtain 0.58 g (95%) of an orange powder.

$MH^+$=413.4; melting point: 164° C.

Stage C: 3,3'-{Undecane-1,11-diylbis[imino(2-oxoethane-2,1-diyl)oxy(1-methoxy-2-methylindolizine-8,3-diyl)carbonyl]}bis(methyl 6-aminobenzoate)

0.33 ml (2.38 mmol) of triethylamine and 0.56 g (1.75 mmol) of TBTU (O-benzotriazol-1-yl-N,N,N',N'-tetramethyluronium tetrafluoroborate), followed by 0.148 g (0.79 mmol) of 1,11-diaminoundecane, are added successively to the solution of 0.66 g (1.59 mmol) of ({3-[4-amino-3-(methoxycarbonyl)benzoyl]-1-methoxy-2-methylindolizin-8-yl}oxy)acetic acid in 8 ml of N,N-dimethylformamide. The reaction mixture is stirred at ambient temperature under nitrogen for 3 days, diluted with ethyl acetate, and washed with a saturated solution of sodium bicarbonate and then with a saturated solution of sodium chloride. The organic phase is dried over sodium sulphate and concentrated to dryness. The solid obtained is purified by steric exclusion chromatography on Sephadex® LH20 gel (N,N-dimethylformamide), and 0.18 g (23%) of a yellow powder is obtained.

$MH^+$=975.5.

Stage D: 3,3'-{Undecane-1,11-diylbis[imino(2-oxoethane-2,1-diyl)oxy(1-methoxy-2-methylindolizine-8,3-diyl)carbonyl]}bis(6-aminobenzoic acid)

0.35 ml of sodium hydroxide (1 M) is added to the solution of 0.17 g (0.18 mmol) of the dimer obtained in stage C above in 1 ml of 1-methyl-2-pyrrolidinone. The solution is stirred at ambient temperature for 3 days. The reaction medium is poured into an aqueous solution of potassium hydrogen sulphate. The yellow precipitate is filtered, dried, and purified by FPLC chromatography on C8 Kromasyl 10μ gel [gradient of methanol/0.017 M aqueous solution of ammonium acetate/acetonitrile=5/95/0 to 45/5/50]. 28 mg of a yellow powder are obtained.

MH+=947.7.

Stage E

60 μl of sodium hydroxide (1 M) are added to the suspension of 27 mg (0.03 mmol) of the dicarboxylic acid obtained in Stage D above in 3 ml of methanol. The solution is concentrated and the solid obtained is taken up with acetone. The insoluble material is filtered and dried under vacuum at 50° C. so as to obtain 17 mg of a yellow powder (disodium salt, 3.5 mol of water).

Melting point: 220° C. $^1$H-NMR [$(CD_3)_2SO$, 250 MHz]: 8.61 (2H, d), 8.14 (2H, s), 7.98 (2H, t), 7.50-8.00 (4H, broad s), 7.37 (2H, d), 6.53-6.60 (4H, m), 6.35 (2H, dd), 4.67 (4H, s), 3.81 (6H, s), 3.18 (4H, dd), 1.96 (6H, s), 1.40-1.50 (4H, m), 1.20-1.30 (14H, m).

EXAMPLE 8

Disodium salt of 3,3'-(3,6,9,12,15-pentaoxaheptadecane-1,17-diylbis{oxy[3-(4-amino-3-methoxybenzoyl)imidazo[1,5-a]pyridine-8,1-diyl]})dibenzoic acid Stage A: Methyl 3,3'-(3,6,9,12,15-pentaoxaheptadecane-1,17-diylbis{oxy[3-(4-amino-3-methoxybenzoyl)-imidazo[1,5-a]pyridine-8,1-diyl]})dibenzoate 0.2 g (4.60 mmol) of sodium hydride (60% as a dispersion in oil) is added, portionwise, to 1.6 g (3.83 mmol) of methyl 3-[3-(4-amino-3-methoxybenzoyl)-8-hydroxyimidazo[1,5-a]pyridin-1-yl]benzoate (described in Patent Application FR0502590) in solution in 15 ml of N,N-dimethylformamide at 0° C., followed, after 10 minutes, by 0.25 g (1.92 mmol) of 1,17-diiodo-3,6,9,12,15-pentaoxaheptadecane (Example R2). The mixture is stirred at 60° C. for 6 hours. The reaction medium is poured into a solution of hydrochloric acid (0.1 M). The precipitate is filtered, washed with water, and then dried at 50° C. under vacuum. After purification by chromatography on silica gel (dichloromethane/acetone gradient=95/5 to 75/25), 0.6 g (29%) of a yellow powder is obtained.

$MH^+$=1081.7; melting point: 80.2° C.

Stage B: 3,3'-(3,6,9,12,15-pentaoxaheptadecane-1,17-diylbis{oxy[3-(4-amino-3-methoxybenzoyl)-imidazo[1,5-a]pyridine-8,1-diyl]})dibenzoic acid The solution of 0.4 g (0.37 mmol) of the dimer obtained in Stage A above in 0.92 ml of sodium hydroxide (1 M) and 7.4 ml of dimethyl sulphoxide is heated at 100° C. for 5 minutes. After cooling, it is run into 200 ml of water containing 0.13 g of potassium hydrogen sulphate. The precipitate obtained is filtered, washed, and dried under vacuum at 50° C. 0.36 g (92%) of a yellow powder is obtained.

$MH^+$=1053.4.

Stage C 0.60 ml of sodium hydroxide (1 M) is added to the solution of 0.323 g (0.31 mmol) of the dimer obtained in stage B above in 30 ml of methanol. The solution is stirred at ambient temperature for 30 minutes. The solid obtained is taken up in acetone, filtered and dried under vacuum at 50° C., to give 0.33 g of a yellow powder (disodium salt, 5 mol of water).

melting point: 209.6° C. $^1$H-NMR [$(CD_3)_2SO$, 400 MHz]: 9.33 (2H, d), 8.44 (2H, s), 8.19 (2H, s), 8.13 (2H, d), 7.87 (2H, d), 7.82 (2H, d), 7.32 (2H, dd), 7.03 (2H, dd), 6.71 (4H, m), 5.79 (4H, s), 4.20-4.30 (4H, m), 3.90 (6H, s), 3.70-3.85 (4H, dd), 3.30-3.50 (16H, m).

EXAMPLE 9

By following the processes described in stages A to C of Example 8, Example 9 is prepared by dimerization of (4-amino-3-methoxyphenyl)(8-hydroxy-1-pyridin-4-yl-imidazo[1,5-a]pyridin-3-yl)methanone (compound obtained by adapting the protocols described in patent application WO 2006/097625 for the preparation of methyl 3-[3-(4-amino-3-methoxybenzoyl)-8-hydroxy-imidazo[1,5-a]pyridin-1-yl] benzoate) with the appropriate diiodinated derivative (Example R2).

EXAMPLE 10

[3,6,9,12,15-Pentaoxaheptadecane-1,17-diylbis(oxyimidazo[1,5-a]pyridine-8,3-diyl)]bis[(4-amino-3-methoxyphenyl)methanone]hydrochloride Stage A: [3,6,9,12,15-Pentaoxaheptadecane-1,17-diylbis(oxyimidazo[1,5-a]pyridine-8,3-diyl)]bis[(4-amino-3-methoxyphenyl)methanone]

By following the process described in Stage A of Example 8, Example 10 is prepared from (4-amino-3-methoxyphenyl)(8-hydroxyimidazo[1,5-a]pyridin-3-yl)-methanone (described in Patent Application WO2006097625) with 1,17-diiodo-3,6,9,12,15-pentaoxaheptadecane (Example R2). After purification by flash chromatography on silica gel (dichloromethane/acetone gradient=90/10 to 70/30), 0.93 g (27%) of a yellow powder is obtained.
MH$^+$=813.5.

Stage B 0.92 ml of hydrochloric ethyl ether (1M) is added to the suspension of 0.25 g (0.31 mmol) of the dimer obtained in the stage above in 6 ml of methanol. The mixture is concentrated to dryness, the solid is taken up in ethyl ether, and the product is filtered and dried at 50° C. under vacuum, so as to obtain 0.22 g of a yellow powder (dihydrochloride, 5 mol of water).
melting point: 209° C. $^1$H-NMR [(CD$_3$)$_2$SO, 400 MHz]: 9.23 (2H, d), 8.21 (2H, dd), 7.90 (2H, s), 7.74 (2H, s), 7.03 (2H, dd), 6.80 (2H, d), 6.71 (2H, d), 4.00-5.00 (4H, broad s), 4.30-4.35 (4H, m), 3.80-3.90 (8H, m), 3.60-3.70 (4H, m), 3.45-3.60 (12H, m).

EXAMPLE 11

Disodium salt of 3,3'-{3,6,9,12,15,18-hexaoxa-icosane-1,20-diylbis[oxy(1-methoxy-2-methylindolizine-6,3-diyl)carbonyl]}bis(6-aminobenzoic acid).

Stage A: 5-(Benzyloxy)-2-(methoxymethyl)pyridine 50 g (0.21 mol) of 5-benzyloxy-2-chloromethylpyridine (CAS 127590-90-3; D. I. Scopes, N. F. Norman, D. E. Bays, D. Belton, J. Brain et al., *J. Med. Chem.*, 1992, 35, 490-501) in solution in 150 ml of methanol are added to the solution of sodium methoxide prepared by adding 6.4 g (0.28 mol) of sodium to 150 ml of methanol. After refluxing for 3 hours under nitrogen, the solution is concentrated to dryness. The oil obtained is taken up in ethyl acetate. The solution is washed with a saturated aqueous solution of sodium chloride, dried over anhydrous sodium sulphate and then concentrated to dryness. 46 g (94%) of a brown oil are obtained.
MH$^+$=230.1.

Stage B:
6-(Benzyloxy)-1-methoxy-2-methylindolizine 22.5 g (0.098 mol) of 5-(benzyloxy)-2-(methoxymethyl)-pyridine in solution in 10 ml of ethanol are added, dropwise at ambient temperature, to the suspension of 22 g (0.25 mol) of lithium bromide and 20 ml (0.25 mol) of chloroacetone in 250 ml of ethanol at ambient temperature. The mixture is refluxed for 17 hours and then concentrated to dryness. It is taken up in ethyl acetate and extracted with water. The aqueous phase, which contains the quaternized pyridine, is washed with ethyl acetate and then concentrated to dryness.

A brown oil is obtained, which is solubilized in a mixture of 400 ml of acetonitrile and 13 ml of ethanol. The solution is brought to reflux before the dropwise addition of 41 ml (0.30 mol) of triethylamine. The mixture is kept at reflux for 2 hours 30 min. The reaction medium is a homogeneous dark brown colour. It is concentrated and then taken up with ethyl acetate and washed with water and then with a saturated aqueous solution of sodium chloride. The organic phase is dried over anhydrous sodium sulphate and then concentrated to dryness. 12.8 g of a greeny brown solid are obtained, which solid is used as it is in the subsequent stage.
MH$^+$=268.1.

Stage C: 6-{[6-(Benzyloxy)-1-methoxy-2-methylindolizin-3-yl]carbonyl}-2-phenyl-4H-3,1-benzoxazin-4-one 10 ml (71.8 mmol) of triethylamine and 15 g (52.7 mmol) of 4-oxo-2-phenyl-4H-3,1-benzoxazine-6-carbonyl chloride are added portionwise, at ambient temperature and under nitrogen, to the solution of 12.8 g (47.9 mmol) of 6-(benzyloxy)-1-methoxy-2-methylindolizine in 160 ml of dichloromethane. The reaction medium is stirred for 2 hours and is then filtered. The solid obtained is washed with dichloromethane and then with diisopropyl ether and dried. 17.8 g (83%) of an orange powder are obtained.
MH$^+$=517.3; melting point: 224.6° C. (decomposition).

Stage D: 2-Amino-5-[(6-benzyloxy-1-methoxy-2-methylindolizin-3-yl)carbonyl]benzoic acid A solution of 2.17 g (38.7 mmol) of potassium hydroxide in 6 ml of water is added to the suspension of 2.0 g (3.87 mmol) of 6-{[6-(benzyloxy)-1-methoxy-2-methylindolizin-3-yl] carbonyl}-2-phenyl-4H-3,1-benzoxazin-4-one in 15 ml of N-methyl-2-pyrrolidone at ambient temperature. The mixture is brought to reflux for 4 hours. After cooling, the reaction medium is poured into an aqueous solution of hydrochloric acid (0.1 M). The precipitate formed is filtered and washed thoroughly with water and then with diisopropyl ether. 1.15 g (70%) of a yellow powder are obtained after drying under vacuum at 50° C.
MH$^+$=431.4; melting point: 246° C. (decomposition).

Stage E: Methyl 2-amino-5-[(6-benzyloxy-1-methoxy-2-methylindolizin-3-yl)carbonyl]benzoate 0.34 ml (5.53 mmol) of methyl iodide is added to the mixture of 1.19 g (2.76 mmol) of the carboxylic acid obtained in Stage E above and 0.5 g (3.59 mmol) of potassium carbonate in 7.0 ml of N,N-dimethylformamide. The solution is stirred for 4 hours at ambient temperature under nitrogen, and is then poured into a saturated aqueous solution of sodium hydrogen carbonate. The precipitate formed is filtered and washed thoroughly with water and then diisopropyl ether, to give 0.96 g (90%) of a yellow powder after drying.
MH$^+$=445.2; melting point: 189° C. (decomposition).

Stage F: Methyl 2-amino-5-[(6-hydroxy-1-methoxy-2-methylindolizin-3-yl)carbonyl]benzoate The mixture of 0.95 g (2.14 mmol) of methyl 2-amino-5-[(6-benzyloxy-1-methoxy-2-methylindolizin-3-yl)carbonyl]

benzoate, 0.21 g (3.21 mmol) of ammonium formate and 0.19 g of palladium-on-charcoal at 10% in 12 ml of N,N-dimethylformamide is stirred for 4 hours at ambient temperature. It is then filtered and concentrated to dryness. The solid obtained is taken up with diisopropyl ether and then filtered, to give 0.64 g (85%) of a yellow powder.

$MH^+=355.3$; melting point: 216° C.

Stage G: 3,3'-{3,6,9,12,15,18-Hexaoxaicosane-1,20-diylbis[oxy(1-methoxy-2-methylindolizine-6,3-diyl)carbonyl]}bis(methyl 6-aminobenzoate)

5.68 ml (2.84 mmol) of potassium bis(trimethylsilyl)amide (0.5M in toluene) are added to the solution of 0.77 g (1.42 mmol) of methyl 2-amino-5-[(6-hydroxy-1-methoxy-2-methylindolizin-3-yl)carbonyl]benzoate in 30 ml of tetrahydrofuran at −40° C. A precipitate forms. The reaction medium is allowed to return to ambient temperature and then 20 ml of N,N-dimethylformamide and 0.64 g (1.41 mmol) of 1,20-diiodo-3,6,9,12,15,18-hexaoxaicosane (Example R1) are added. The solution is heated for 24 hours at 60° C. The reaction medium is run into a solution of 0.9 g of potassium hydrogen sulphate in 100 ml of water and the mixture is extracted with ethyl acetate. The organic phase is washed with water and then with a saturated aqueous solution of sodium chloride, dried over sodium sulphate and concentrated to dryness. The brown oil obtained is purified by flash chromatography on silica gel (toluene/ethyl acetate gradient=100/0 to 0/100). 0.35 g (24%) of a yellow powder is obtained.

$MH^+=999.4$; melting point: 80° C.

Stage H 0.41 ml of sodium hydroxide (1 M) is added to the suspension of 0.20 g (0.21 mmol) of the dimer obtained in stage F above in 0.5 ml of methanol. The solution is stirred at ambient temperature for 30 minutes and then concentrated to dryness. The solid obtained is taken up in acetone, filtered, and dried under vacuum at 50° C., to give 0.14 g of a yellow powder (disodium salt, 7.4 mol of water).

melting point: 181° C. $^1$H-NMR [$(CD_3)_2SO$, 250 MHz]: 8.89 (2H, s), 8.11 (2H, s), 7.49 (2H, d), 7.40-8.10 (4H, broad s), 7.35 (2H, dd), 6.86 (2H, dd), 6.58 (2H, dd), 4.00-4.10 (4H, m), 3.81 (6H, s), 3.70-3.08 (4H, m), 3.20-3.65 (20H, m), 1.94 (6H, s).

EXAMPLES 12 TO 16

By following the processes described in stages F to H of Example 11, Examples 12 to 16 are prepared by dimerization of methyl 2-amino-5-[(6-hydroxy-1-methoxy-2-methylindolizin-3-yl)carbonyl]benzoate (stage E of Example 11) with the appropriate diodinated derivatives (Examples R2 to R6).

EXAMPLES 17 TO 20

By following the processes described in stages F to H of Example 11, Examples 17 and 18 are prepared by dimerization of methyl 2-amino-5-{[2-(4-hydroxyphenyl)-1-methoxyindolizin-3-yl]carbonyl}benzoate (compound obtained by adapting the protocols described in patent application WO 2003/084956) and Examples 19 and 20 are prepared by dimerization of methyl 2-amino-5-{[2-(3-hydroxyphenyl)-1-methoxyindolizin-3-yl]carbonyl}-benzoate (compound obtained by adapting the protocols described in patent application WO 2003/084956) with the appropriate diiodinated derivatives (Examples R6 and R5).

EXAMPLE 21

Disodium salt of 3,3'-{3,6,9,12,15,18-hexaoxaicosane-1,20-diylbis[oxy(2-methylindolizine-1,3-diyl)carbonyl]}bis(6-aminobenzoic acid)

By following the processes described in stages F and G of Example 1, Example 21 is prepared by dimerization of methyl 2-amino-5-[(1-hydroxy-2-methylindolizin-3-yl)-carbonyl]benzoate (described in Patent Application WO2003084956) with 1,20-diiodo-3,6,9,12,15,18-hexaoxaicosane (Example R1). The disodium salt is obtained ($5.5H_2O$).

melting point: 224° C. $^1$H-NMR [$(CD_3)_2SO$, 400 MHz]: 9.06 (2H, d), 8.14 (2H, s), 7.55 (2H, d), 7.50-8.00 (4H, broad s), 7.35 (2H, dd), 6.97 (2H, dd), 6.73 (2H, dd), 6.58 (2H, d), 4.05-4.15 (4H, m), 3.65-3.70 (4H, m), 3.50-3.60 (20H, m), 1.97 (6H, s).

EXAMPLE 22

Disodium salt of 3,3'-{3,6,9,12,15-pentaoxaheptadecane-1,17-diylbis[oxy(2-methylindolizine-1,3-diyl)carbonyl]}bis(6-aminobenzoic acid)

Stage A: 3,3'-{3,6,9,12,15-Pentaoxaheptadecane-1,17-diylbis[oxy(2-methylindolizine-1,3-diyl)carbonyl]}bis(methyl 6-aminobenzoate)

1.10 g (3.39 mmol) of methyl 2-amino-5-[(1-hydroxy-2-methylindolizin-3-yl)carbonyl]benzoate are added portionwise to the suspension of 148 mg (3.39 mmol) of sodium hydride (60% as a dispersion in oil) at ambient temperature in 14 ml of N,N-dimethylformamide under argon at 0° C. After 5 minutes, 0.85 g (1.70 mmol) of 1,17-diiodo-3,6,9,12,15-pentaoxaheptadecane (Example R2) in solution in 1 ml of N,N-dimethylformamide is added. The mixture is stirred at ambient temperature for 3 hours. The reaction medium is poured into a saturated solution of sodium bicarbonate and extracted with ethyl acetate. After separation by settling out, the organic phase is washed with water and then with a saturated aqueous solution of sodium chloride, dried over sodium sulphate and concentrated under reduced pressure. The residue obtained is purified by flash chromatography on silica gel (dichloromethane/ethyl acetate gradient=70/30 to 40/60). 0.82 g (60%) of a yellow powder is obtained.

$MH^+=895.6$.

Stage B: 3,3'-{3,6,9,12,15-Pentaoxaheptadecane-1,17-diylbis[oxy(2-methylindolizine-1,3-diyl)carbonyl]}bis(6-aminobenzoic acid)

1.33 ml of sodium hydroxide (1 M) are added to the solution of 0.50 g (0.56 mmol) of the dimer obtained in stage A above in 4 ml of methanol and 2 ml of 1,4-dioxane. The solution is heated at 80° C. for 4 hours. The solution is concentrated to dryness. The residue obtained is dissolved in water. 0.2 g of potassium hydrogen sulphate is added. The yellow precipitate formed is filtered and dried, to give 0.42 g (87%) of a yellow powder.

$MH^+=867.5$.

Stage C

The product is salified by the addition of 0.85 ml of sodium hydroxide (1 M) to the suspension of 0.37 g (0.43 mmol) of the dicarboxylic acid obtained in stage B above in 50 ml of methanol. The solution is concentrated to dryness and then the solid obtained is taken up in acetone, filtered and dried under vacuum at 50° C. 0.36 g (93%) of a yellow powder is obtained (disodium salt, 4H$_2$O).

melting point: 165.4° C. $^1$H-NMR [(CD$_3$)$_2$SO, 250 MHz]: 9.09 (2H, d), 8.16 (2H, s), 7.56 (2H, d), 7.37 (2H, dd), 7.00-8.00 (4H, broad s), 6.98 (2H, dd), 6.73 (2H, dd), 6.61 (2H, d), 4.05-4.15 (4H, m), 3.45-3.70 (20H, m), 2.00 (6H, s).

EXAMPLES 23 TO 29

By following the processes described in stages A to C of Example 22, Examples 23 to 29 are prepared by dimerization of methyl 2-amino-5-[(1-hydroxy-2-methylindolizin-3-yl)carbonyl]benzoate (described in Patent Application WO2003084956) with the appropriate alkylating agents (Examples R3 to R9).

EXAMPLE 30

Disodium salt of 3,3'-{ethane-1,2-diylbis[imino(2-oxoethane-2,1-diyl)oxy-3,1-phenylenemethyleneoxy(2-methylindolizine-1,3-diyl)carbonyl]}bis(6-aminobenzoic acid)

Stage A: Methyl 2-amino-5-[(1-{[3-(2-tert-butoxy-2-oxoethoxy)benzyl]oxy}-2-methylindolizin-3-yl)carbonyl]benzoate 5.43 ml (2.71 mmol) of potassium bis(trimethylsilyl)amide at −20° C. are added to the solution of 0.80 g (2.47 mmol) of methyl 2-amino-5-[(1-hydroxy-2-methylindolizin-3-yl)carbonyl]benzoate in 12 ml of tetrahydrofuran. After 15 minutes, 1.49 g (4.93 mmol) of tert-butyl[3-(bromomethyl)phenoxy]acetate (CAS 176673-59-9 described in Patent Application WO2004014366) in solution in 2 ml of tetrahydrofuran are added and the mixture is then heated at 40° C. for 12 hours. The reaction medium is poured into a saturated aqueous solution of potassium hydrogen sulphate, and the mixture is extracted with ethyl acetate. The organic phase is washed with water and then with a saturated aqueous solution of sodium chloride, dried over sodium sulphate and concentrated under reduced pressure. After purification by flash chromatography on silica gel (toluene/ethyl acetate gradient=100/00 to 60/40), 0.92 g (61%) of a yellow oil is obtained.
MH$^+$=543.3.

Stage B: {3-[({3-[4-Amino-3-(methoxycarbonyl)-benzoyl]-2-methylindolizin-1-yl}oxy)methyl]phenoxy}acetic acid The solution of 0.87 g (1.60 mmol) of methyl 2-amino-5-[(1-{[3-(2-tert-butoxy-2-oxoethoxy)benzyl]oxy}-2-methylindolizin-3-yl)carbonyl]benzoate in 3.0 ml of trifluoroacetic acid and 16 ml of dichloromethane at ambient temperature is stirred for 4 hours at ambient temperature. The reaction medium is poured into a saturated aqueous solution of sodium bicarbonate and the mixture is washed with ethyl acetate. The aqueous phase is acidified with a saturated aqueous solution of potassium hydrogen sulphate and then extracted with ethyl acetate. The organic phase is washed with a saturated aqueous solution of sodium chloride, dried over sodium sulphate and concentrated under reduced pressure. 0.69 g (88%) of a green solid is obtained.
MH$^+$=489.2.

Stage C: 3,3'-{Ethane-1,2-diylbis[imino(2-oxoethane-2,1-diyl)oxy-3,1-phenylenemethyleneoxy(2-methylindolizine-1,3-diyl)carbonyl]}bis(methyl 6-aminobenzoate)

0.4 ml (2.87 mmol) of triethylamine and 0.67 g (1.50 mmol) of BOP are added, at 0° C. under argon, to the solution of 0.7 g (1.43 mmol) of {3-[({3-[4-amino-3-(methoxycarbonyl)benzoyl]-2-methylindolizin-1-yl}oxy)methyl]phenoxy}acetic acid in solution in 5 ml of N,N-dimethylformamide. After 30 minutes, 50 μl (0.72 mmol) of ethane-1,2-diamine are added. The reaction medium is stirred at ambient temperature for 48 hours. The reaction medium is poured into a saturated aqueous solution of potassium hydrogen sulphate and the mixture is extracted with ethyl acetate. The organic phase is washed with a saturated aqueous solution of sodium chloride, dried over sodium sulphate and concentrated under reduced pressure. The solid obtained is purified by steric exclusion chromatography on Sephadex® LH20 gel (N,N-dimethylformamide), and 262 mg (36%) of a yellow powder are obtained.
MH$^+$=1001.4.

Stage D: 3,3'-{Ethane-1,2-diylbis[imino(2-oxoethane-2,1-diyl)oxy-3,1-phenylenemethyleneoxy(2-methylindolizine-1,3-diyl)carbonyl]}bis(6-aminobenzoic acid)

0.67 ml of sodium hydroxide (1 M) is added to the solution of 257 mg (0.26 mmol) of the dimer obtained in stage E above in 6 ml of 1-methyl-2-pyrrolidinone. The solution is stirred at ambient temperature for 3 days. The reaction medium is poured into 100 ml of water containing 99 mg of potassium hydrogen sulphate. The precipitate is isolated by ultrafiltration and dried. The residue is purified by steric exclusion chromatography on Sephadex® LH20 gel (N,N-dimethylformamide). 193 mg (76%) of a yellow powder are obtained.
MH$^+$=973.7.

Stage E

The product is salified by the addition of 0.37 ml of a molar solution of sodium hydroxide to the suspension of 185 mg (0.19 mmol) of the dicarboxylic acid obtained in the stage above in 20 ml of methanol. The solution is concentrated to dryness and the solid obtained is then taken up in acetone, filtered and dried under vacuum at 50° C. 113 mg of a yellow powder are obtained (disodium salt, 3H$_2$O, 1 acetone).

melting point: 295.7° C. $^1$H-NMR [(CD$_3$)$_2$SO, 250 MHz]: 9.61 (2H, broad s), 9.02 (2H, d), 8.16 (2H, d), 7.42 (4H, dd), 7.27 (2H, dd), 7.11 (2H, d), 7.02 (2H, s), 7.00-8.00 (4H, broad s), 6.89 (4H, ddd), 6.61-6.70 (4H, m), 4.99 (4H, s), 4.51 (4H, s), 3.25-3.35 (4H, m), 1.96 (6H, s).

EXAMPLES 31 AND 32

By following the processes described in stages C to E of Example 30, Examples 31 and 32 are prepared by dimerization of ({3-[4-amino-3-(methoxycarbonyl)benzoyl]-2-methylindolizin-1-yl}oxy)acetic acid (described in Patent Application WO2003084956) with the appropriate commercial diamines.

EXAMPLE 33

Disodium salt of 3,3'-{3,6,9,12-tetraoxatetradecane-1,14-diylbis[imino(2-methylindolizine-1,3-diyl)carbonyl]}bis(6-aminobenzoic acid)

Stage A 1.60 g (3.78 mmol) of methyl 2-amino-5-({1-[(tert-butoxycarbonyl)amino]-2-methylindolizin-3-yl}carbonyl)benzoate (described in Patent Application WO21003084956) in solution in 13 ml of N,N-dimethylformamide are added to the suspension of 0.15 g (3.78 mmol) of sodium hydride (60% as a dispersion in oil) in 5 ml of N,N-dimethylformamide at 0° C. under argon. After 10 minutes, 0.87 g (1.89 mmol) of 1,14-diiodo-3,6,9,12-tetraoxatetradecane (Example R3) in 1 ml of N,N-dimethylformamide is added. The mixture is stirred at ambient temperature for 20 hours. The reaction medium is diluted with ethyl acetate and washed with a saturated aqueous solution of sodium chloride. The organic phase is dried over sodium sulphate and concentrated under reduced pressure. The residue obtained is purified by flash chromatography on silica gel (dichloromethane/methanol gradient=100/0 to 98/2). 1.15 g (58%) of a yellow powder are obtained.

MH+=1049.4; melting point: 104° C.

Stage B: 3,3'-{3,6,9,12-Tetraoxatetradecane-1,14-diylbis[imino(2-methylindolizine-1,3-diyl)carbonyl]}bis(methyl 6-aminobenzoate)

The solution of 1.06 g (1.01 mmol) of the dimer obtained in stage A above in 10 ml of dichloromethane and 3 ml of trifluoroacetic acid. The solution is stirred at ambient temperature for 2 hours. The solution is run into a saturated aqueous solution of sodium bicarbonate and extracted with dichloromethane. The organic phase is washed with water and with a saturated aqueous solution of sodium chloride, dried over sodium sulphate and concentrated under reduced pressure. The residue obtained is purified by flash chromatography on silica gel (ethyl acetate/methanol gradient=100/0 to 97/3). 0.67 g (78%) of an orange powder is obtained.

MH$^+$=849.3; melting point: 66° C.

Stage C: 3,3'-{3,6,9,12-Tetraoxatetradecane-1,14-diylbis[imino(2-methylindolizine-1,3-diyl)carbonyl]}bis(6-aminobenzoic acid)

The solution of 0.64 g (0.75 mmol) of the dimer obtained in stage B above in the presence of 1.51 ml of sodium hydroxide (1 M) in 4 ml of 1,4-dioxane is refluxed for 17 hours. The reaction mixture is concentrated to dryness and then dissolved in water. After the addition of 226 mg of potassium hydrogen sulphate, an orange precipitate is obtained, which is filtered and thoroughly washed with water and then dried under vacuum at 50° C., to give 0.54 g (60%) of an orange powder.

Stage D

The final product is salified in the form of a disodium salt by the addition of 1.17 ml of sodium hydroxide (1 M) to the suspension of 0.48 g (0.59 mmol) in 20 ml of methanol. The solution is concentrated to dryness. The solid is taken up in acetone, filtered and dried, to give 0.46 g (61%) of a red powder (disodium salt, 4H$_2$O).

melting point: 193° C. (decomposition). $^1$H-NMR [(CD$_3$)$_2$SO, 250 MHz]: 9.11 (2H, d), 8.14 (2H, d), 7.60 (2H, d), 7.36 (2H, dd), 7.00-8.00 (4H, broad s), 6.91 (2H, dd), 6.67 (2H, dd), 6.60 (2H, d), 3.90-4.10 (2H, broad s), 3.50-3.60 (12H, m), 3.44 (4H, t), 3.05-3.15 (4H, m), 1.97 (6H, s).

EXAMPLE 34

Disodium salt of 3,3'-{octane-1,8-diylbis[oxy-3,1-phenylenecarbonylimino(2-methyl-indolizine-1,3-diyl)carbonyl]}bis(6-aminobenzoic acid)

Stage A: Methyl 5-[(1-{[3-(acetyloxy)benzoyl]amino}-2-methylindolizin-3-yl)-carbonyl]-2-aminobenzoate 0.95 ml (6.80 mmol) of triethylamine and 1.50 g (3.40 mmol) of BOP are added, at ambient temperature, to 0.61 g (3.40 mmol) of 3-acetoxybenzoic acid in suspension in 20 ml of N,N-dimethylformamide. After 15 minutes, 1.0 g (3.09 mmol) of methyl 2-amino-5-[(1-amino-2-methylindolizin-3-yl)carbonyl]benzoate (described in Patent Application WO2003084956) in 10 ml of N,N-dimethylformamide is added. The reaction medium is stirred for 16 hours under argon and then diluted with ethyl acetate and washed with a saturated aqueous solution of sodium bicarbonate. The organic phase is washed with a saturated aqueous solution of sodium chloride, dried over sodium sulphate and concentrated under reduced pressure. The solid obtained is taken up in acetone and then filtered and dried. 0.86 g (57%) of a greenish yellow powder is obtained.

MH$^+$=486.3; melting point: 210° C.

Stage B: Methyl 2-amino-5-({1-[(3-hydroxybenzoyl)-amino]-2-methylindolizin-3-yl}carbonyl)benzoate 0.46 g (3.30 mmol) of potassium carbonate dissolved in 4 ml of water is added to the suspension of 0.80 g (1.65 mmol) of methyl 5-[(1-{[3-(acetyloxy)benzoyl]-amino}-2-methylindolizin-3-yl)carbonyl]-2-aminobenzoate in 16 ml of methanol. The reaction medium is stirred at ambient temperature for 1 hour, it gradually becomes homogenized. It is diluted with ethyl acetate and acidified with a molar solution of hydrochloric acid. The two phases are separated. The organic phase is washed with a saturated aqueous solution of sodium chloride, dried over sodium sulphate and concentrated under reduced pressure. The solid obtained is taken up in ethyl ether and then filtered and dried. 0.61 g (84%) of a greenish yellow powder is obtained.

MH$^+$=444.3; melting point: 278° C.

Stage C: 3,3'-{Octane-1,8-diylbis[oxy-3,1-phenylenecarbonylimino(2-methylindolizine-1,3-diyl)carbonyl]}bis(methyl 6-aminobenzoate)

0.72 g (1.63 mmol) of methyl 2-amino-5-({1-[(3-hydroxybenzoyl)amino]-2-methylindolizin-3-yl}carbonyl)-benzoate is added, under argon, to the suspension of 71 mg (1.63 mmol) of sodium hydride (60% as a dispersion in oil) at ambient temperature in 15 ml of N,N-dimethylformamide. After 15 minutes, 0.30 g (0.82 mmol) of 1,8-diiodooctane is added. The mixture is heated at 60° C. for 72 hours. The reaction medium is acidified with a saturated aqueous solution of potassium hydrogen sulphate and then extracted with ethyl acetate. The organic phase is washed with water and then with a saturated aqueous solution of sodium chloride, dried over sodium sulphate and concentrated under reduced pressure. The residue obtained is dissolved in the minimum amount of N,N-dimethylformamide and purified by steric exclusion chromatography on Sephadex® LH20 gel (N,N-di-methyl-formamide). 0.50 g (61%) of a yellow powder is obtained.

MH+=983.4; melting point: 213° C.

Stage D 0.38 ml of sodium hydroxide (1 M) is added to the solution of 185 mg (0.19 mmol) of the dicarboxylic acid obtained in the preceding stage in 5 ml of methanol. The solution is concentrated to dryness and the solid obtained is then taken up in acetone, filtered and dried. 152 mg of a yellow powder are obtained (disodium salt, 5H$_2$O, 0.35 N,N-dimethylformamide).

melting point: 263° C. (decomposition) $^1$H-NMR [(CD$_3$)$_2$SO, 250 MHz]: 9.97 (2H, s), 9.12 (2H, d) 8.20 (2H, s), 7.63 (2H, d), 7.36-7.46 (8H, m), 7.30-8.00 (4H, broad s), 7.15 (2H, dd), 7.05 (2H, dd), 6.81 (2H, dd), 6.62 (2H, d), 4.07 (4H, t), 1.96 (6H, s), 1.70-1.85 (4H, m), 1.35-1.55 (8H, m).

EXAMPLES 35 TO 41

By following the processes described in stages E and F of Example 34, Examples 35 to 41 are prepared by dimerization of methyl 2-amino-5-({1-[(3-hydroxybenzoyl)amino]-2-methylindolizin-3-yl}carbonyl)benzoate (stage D of Example 34) with the appropriate alkylating agents (Examples R2 to R6, R10 and R11).

EXAMPLE 42

Disodium salt of 3,3'={(1,4-dioxobutane-1,4-diyl)bis [iminoethane-2,1-diyloxy-3,1-phenylenecarbon-ylimino(2-methylindolizine-1,3-diyl)carbonyl]}bis (6-aminobenzoic acid)

Stage A: 3-{[(Pyridin-2-ylmethyl)amino]carbonyl}-phenyl acetate 93 ml (0.66 mol) of triethylamine and 160 g (0.36 mol) of benzotriazol-1-yloxytris(dimethylamino)phosphonium hexafluorophosphate (BOP) are added, at ambient temperature under argon, to 65.0 g (0.36 mol) of 3-acetoxybenzoic acid in solution in 600 ml of dichloromethane. After 10 minutes, 32.5 g (0.30 mol) of 2-(aminomethyl)pyridine in solution in 200 ml of dichloromethane are added dropwise at 0° C. The reaction medium is allowed to return to ambient temperature and then stirred for 3 hours.

The reaction medium is diluted with ethyl acetate and extracted with a saturated aqueous solution of sodium bicarbonate. The organic phase is washed with a saturated aqueous solution of sodium chloride, dried over sodium sulphate and concentrated under reduced pressure. The residue obtained is purified by flash chromatography on silica gel (dichloromethane). 36.0 g (44%) of a brown syrup are obtained, which syrup is used as it is in the subsequent stage.

MH+=271.1.

Stage B: 3-Hydroxy-N-(pyridin-2-ylmethyl)benzamide 11.7 g (0.85 mol) of potassium carbonate in solution in 86 ml of water are added to 11.5 g (0.43 mol) of 3-{[(pyridin-2-ylmethyl)amino]carbonyl}phenyl acetate (stage A) in solution in 340 ml of methanol. The mixture is stirred at ambient temperature for 3 hours and then concentrated to dryness. The residue is taken up in ethyl acetate and the product is neutralized with 85 ml of a molar solution of hydrochloric acid. The two phases are separated. The aqueous phase is extracted three times with ethyl acetate. The organic phases are combined and washed with a saturated aqueous solution of sodium chloride, and dried over sodium sulphate. The solid obtained after concentration under vacuum is washed with ethyl ether and filtered. After drying, 6.3 g (65%) of a white solid are obtained.

MH+=229.1.

Stage C: tert-Butyl[2-(3-{[(pyridin-2-ylmethyl)-amino]carbonyl}phenoxy)ethyl]carbamate 3.96 g (90.7 mmol) of sodium hydride (55% dispersion in oil) are added portionwise to the solution of 18.0 g (78.9 mmol) of 3-hydroxy-N-(pyridin-2-ylmethyl)benzamide in 160 ml of N,N-dimethylformamide at 0° C. under argon. After 1 hour, 23.0 g (0.10 mol) of tert-butyl (2-bromoethyl) carbamate are added and the mixture is heated at 90° C. for 16 hours. The reaction medium is poured into water and the mixture is extracted with ethyl acetate. The organic phase is washed with a saturated aqueous solution of sodium chloride, dried over sodium sulphate and concentrated under reduced pressure. The product is purified by flash chromatography on silica gel (dichloromethane/methanol=9/1). 19.0 g (65%) of a colourless oil are obtained.

MH+=372.2.

Stage D: tert-Butyl[2-(3-{[(2-methylindolizin-1-yl) amino]carbonyl}phenoxy)ethyl]carbamate The mixture of 19.0 g (51.1 mmol) of tert-butyl[2-(3-{[(pyridin-2-ylmethyl)amino]carbonyl}phenoxy)ethyl]-carbamate, 7.1 g (76.7 mmol) of chloroacetone and 8.9 g (102 mmol) of lithium bromide in 100 ml of acetonitrile is refluxed for 16 hours. The mixture is poured into water. The aqueous phase is washed four times with ethyl acetate. The aqueous phase is concentrated so as to obtain a greenish oil.

The solution of quaternized pyridine in 100 ml of acetonitrile is refluxed and then 17.8 ml (0.13 mol) of triethylamine are added. After refluxing for 3 hours under argon, the mixture is concentrated to dryness. It is poured into water and the mixture is extracted with ethyl acetate. The organic phase is washed with a saturated aqueous solution of sodium chloride, dried over sodium sulphate and concentrated under reduced pressure. The brown oil obtained is filtered over silica H (toluene) to give 8.95 g (43%) of a white solid.

MH+=410.5; melting point: 128° C.

Stage E: Benzyl 5-({1-[(3-{2-[(tert-butoxycarbonyl) amino]ethoxy}benzoyl)amino]-2-methylindolizin-3-yl}carbonyl)-2-[(trifluoroacetyl)amino]benzoate 4.43 ml (43.7 mmol) of pyridine and 8.95 g (21.9 mmol) of tert-butyl[2-(3-{[(2-methylindolizin-1-yl)amino]-carbonyl}phenoxy)ethyl]carbamate are added to the suspension of 9.27 g (24.0 mmol) of benzyl 5-(chlorocarbonyl)-2-[(trifluoroacetyl)amino]benzoate in 180 ml of dichloromethane. The reaction medium that has turned greenish is stirred at ambient temperature for 16 hours. It is concentrated to dryness and the residue is taken up in diisopropyl ether and ethanol. The solid in suspension is filtered, washed with diisopropyl ether and dried. 6.29 g (38%) of a yellow powder are obtained.

MH+=759.6.

Stage F: Benzyl 5-[(1-{[3-(2-aminoethoxy)benzoyl]-amino}-2-methylindolizin-3-yl)carbonyl]-2-[(trifluoroacetyl)amino]benzoate 16 ml (0.20 mol) of trifluoroacetic acid are added to the suspension of 6.28 g (8.28 mmol) of benzyl 5-({1-[(3-{2-[(tert-butoxycarbonyl)amino]ethoxy}benzoyl)-amino]-2-methylindolizin-3-yl}carbonyl)-2-[(trifluoroacetyl)amino] benzoate in 40 ml of dichloromethane. After stirring at ambient temperature for 30 minutes, the reaction medium is poured into 1 l of a saturated aqueous solution of sodium bicarbonate. The precipitate is filtered, washed thoroughly with water and then with diisopropyl ether and dried, so as to obtain 4.5 g (82%) of a yellow powder.

MH+=659.5; melting point: 219° C.

Stage G: 3,3'-{(1,4-Dioxobutane-1,4-diyl)bis[imino-ethane-2,1-diyloxy-3,1-phenylenecarbonylimino(2-methylindolizine-1,3-diyl)carbonyl]}bis{6-[(trifluoroacetyl)-amino]benzoate}

0.4 ml (2.94 mmol) of triethylamine and 0.62 g (1.47 mmol) of BOP® are added to 82 mg (0.70 mmol) of succinimic acid in solution in 7 ml of N,N-dimethylformamide. After 15 minutes, 0.92 g (1.40 mmol) of benzyl 5-[(1-{[3-(2-aminoethoxy)benzoyl]amino}-2-methylindolizin-3-yl)carbonyl]-2-[(trifluoroacetyl)amino]-benzoate is added. The reaction medium is stirred at ambient temperature for 48 hours. The reaction medium is diluted with ethyl acetate, filtered and washed with ethyl acetate and then dried, to give 0.43 g (44%) of an orange powder.

MH$^+$=1399.7; melting point: 281° C.

Stage H: 3,3'-{(1,4-Dioxobutane-1,4-diyl)bis[imino-ethane-2,1-diyloxy-3,1-phenylenecarbonylimino(2-methylindolizine-1,3-diyl)carbonyl]}bis{6-[(trifluoroacetyl)amino]benzoic acid}

The mixture of 0.42 g (0.30 mmol) of 3,3'-{(1,4-dioxobutane-1,4-diyl)bis[iminoethane-2,1-diyloxy-3,1-phenylenecarbonylimino(2-methylindolizine-1,3-diyl)-carbonyl]}bis{benzyl 6-[trifluoroacetyl)amino]benzoate} and 0.11 g (1.82 mmol) of ammonium formate in the presence of 0.10 g of palladium-on-charcoal (10%) in 3 ml of N,N-dimethylformamide is stirred for 2 hours at ambient temperature. The mixture is filtered and concentrated to dryness so as to obtain 370 mg (quantitative) of a yellow solid.

MH$^+$=1219.5.

Stage I: 3,3'-{(1,4-Dioxobutane-1,4-diyl)bis[iminoethane-2,1-diyloxy-3,1-phenylenecarbonylimino(2-methylindolizine-1,3-diyl)carbonyl]}bis(6-aminobenzoic acid)

1.17 ml of sodium hydroxide (1 M) are added to the suspension of 365 mg (0.30 mmol) of the dimer obtained in stage B above in 10 ml of methanol. The solution is stirred at ambient temperature for 1 hour. The reaction medium is poured into a saturated aqueous solution of potassium hydrogen sulphate. After filtration and drying of the precipitate obtained, 270 mg (88%) of a green powder are obtained.

MH+=1027.7.

Stage J

The final product is salified in the form of a sodium salt by the addition of 264 mg (0.26 mmol) of the dicarboxylic acid obtained above to a solution containing 0.50 ml of sodium hydroxide (1 M) in 5 ml of water. The solution is lyophilized. The lyophilisate is taken up in acetone, filtered and dried, to give 250 mg of a yellow powder (disodium salt, 5H$_2$O).

melting point: 343° C. (decomposition) $^1$H-NMR [(CD$_3$)$_2$SO, 250 MHz]: 10.00 (2H, s), 9.13 (2H, d), 8.22 (4H, s), 7.65 (2H, s), 7.56-7.59 (4H, m), 7.37-7.47 (4H, m), 7.17 (2H, d), 7.06 (2H, dd), 7.00-8.00 (4H, broad s), 6.82 (2H, dd), 6.63 (2H, d), 4.05-4.15 (4H, m), 3.40-3.55 (4H, m), 2.39 (4H, s), 1.97 (6H, s).

EXAMPLE 43

Disodium salt of 3,3'-{carbonylbis[imino-ethane-2,1-diyloxy-3,1-phenylenecarbonylimino(2-methyl-indolizine-1,3-diyl)carbonyl]}bis(6-aminobenzoic acid)

Stage A: 3.3'-{Carbonylbis[iminoethane-2,1-diyloxy-3,1-phenylenecarbonylimino(2-methylindolizine-1,3-diyl)carbonyl]}bis{benzyl 6-[(trifluoroacetyl)amino]benzoate}

0.18 g (0.70 mmol) of N,N'-disuccinimidylcarbonate is added to 0.92 g (1.40 mmol) of benzyl 5-[(1-{[3-(2-aminoethoxy)benzoyl]amino}-2-methylindolizin-3-yl)carbonyl]-2-[(trifluoroacetyl)amino]benzoate (stage F of Example 42) in solution in 10 ml of N,N-dimethylformamide. The solution is stirred for 3 hours at ambient temperature and is then diluted with ethyl acetate. The precipitate obtained is filtered, washed with ethyl acetate and dried, to give 0.49 g (53%) of a yellow powder.

MH$^+$=1346.6.

Stage B: 3,3'-{Carbonylbis[iminoethane-2,1-diyloxy-3,1-phenylenecarbonylimino(2-methylindolizine-1,3-diyl)carbonyl]}bis(6-aminobenzoic acid)

1.45 ml of sodium hydroxide (1 M) are added to the solution of 300 mg (0.22 mmol) of the dimer obtained in stage A above in 1.5 ml of 1-methyl-2-pyrrolidinone. The solution is stirred at ambient temperature for 16 hours. The reaction medium is poured into 100 ml of water containing 120 mg of potassium hydrogen sulphate. The precipitate obtained is filtered, washed with water dried, to give 155 mg (73%) of an orangey-yellow powder.

MH+=971.5.

Stage C

The final product is salified in the form of a disodium salt. 250 mg (0.26 mmol) of the dicarboxylic acid obtained in stage B above are added portionwise to a solution containing 0.51 ml of sodium hydroxide (1 M) in 26 ml of water. The solution is concentrated to dryness. The solid is taken up in acetone, filtered and dried, to give 220 mg of a yellow powder (disodium salt, 4H$_2$O).

melting point: 354-359° C. (decomposition).

$^1$H-NMR [(CD$_3$)$_2$SO, 250 MHz]: 10.02 (2H, s), 9.14 (2H, d), 8.24 (2H, s), 7.64-7.67 (4H, m), 7.34-7.46 (6H, m), 7.17 (2H, d), 7.05 (2H, dd), 7.00-8.00 (4H, broad s), 6.82 (2H, dd), 6.55-6.70 (4H, m), 4.05-4.15 (4H, m), 3.35-3.40 (4H, m), 1.97 (6H, s).

EXAMPLE 44

Disodium salt of 3,3'-ethane-1,2-diylbis-[imino(2-oxoethane-2,1-diyl)oxy-3,1-phenylenecarbonyl-imino(2-methylindolizine-1,3-diyl)carbonyl]}bis(6-aminobenzoic acid)

Stage A: tert-Butyl (3-{[(pyridin-2-ylmethyl)amino]carbonyl}phenoxy)acetate 23.8 g (0.10 mol) of 3-hydroxy-N-(pyridin-2-ylmethyl)-benzamide (stage B of Example 42) are added portionwise to the suspension of 4.5 g (0.10 mol) of sodium hydride (55% dispersion in oil) in 400 ml of N,N-di-methylformamide at 0° C. under argon, followed, after 10 minutes, by 15.4 ml (0.10 mol) of tert-butyl 2-bromo-acetate. The mixture is stirred at ambient temperature for 1 hour. The reaction medium is diluted with ethyl acetate and extracted with water. The organic phase is washed with a saturated aqueous solution of sodium chloride, dried over sodium sulphate and concentrated under reduced pressure. The white solid is taken up in diisopropyl ether, filtered and dried, to give 26.3 g (74%) of a beige powder.

$MH^+$=343.2.

Stage B: tert-Butyl (3-{[(2-methylindolizin-1-yl)amino]carbonyl}phenoxy)acetate The mixture of 26.0 g (75.9 mmol) of tert-butyl (3-{[(pyridin-2-ylmethyl)amino]carbonyl}phenoxy)acetate, 6.65 ml (83.5 mmol) of chloroacetone and 7.9 g (91.1 mmol) of lithium bromide in 100 ml of acetonitrile is refluxed for 16 hours. The mixture is allowed to cool to ambient temperature and 110 ml of water and ethyl acetate are added. The two phases are separated. The aqueous phase is washed twice with ethyl acetate.

26.2 g (0.19 mol) of potassium carbonate are added to the aqueous phase. The solution is heated at 90° C. for 3 hours under argon. It is extracted with ethyl acetate. The organic phase is washed with a saturated aqueous solution of sodium chloride, dried over sodium sulphate and concentrated under reduced pressure. 7.0 g of a beige solid are obtained, which solid is used as it is in the acylation stage.

MH+=381.5.

Stage C: Benzyl 5-[(1-{[3-(2-tert-butoxy-2-oxo-ethoxy)benzoyl]amino}-2-methylindolizin-3-yl)carbonyl]-2-[(trifluoroacetyl)amino]benzoate A solution of 12.4 g (32.6 mmol) of tert-butyl (3-{[(2-methylindolizin-1-yl)amino]carbonyl}phenoxy)acetate and 2.77 ml of pyridine in 100 ml of dichloromethane is added dropwise, under argon, to 13.0 g (34.2 mmol) of benzyl 5-(chlorocarbonyl)1-2-[(trifluoroacetyl)amino]benzoate (described in Patent Application WO2003084956) in suspension in 60 ml of dichloromethane. The reaction medium, which immediately turns green, is stirred at ambient temperature for 19 hours. The reaction medium is diluted with ethyl acetate and poured into a saturated aqueous solution of sodium bicarbonate. After separation by settling out, the organic phase is washed with a saturated aqueous solution of sodium chloride, dried over sodium sulphate and concentrated under reduced pressure. The solid obtained is adsorbed onto silica and purified by flash chromatography on silica gel (dichloromethane/diethyl ether=95.5). 9.0 g (38%) of a yellow powder are obtained.

$MH^+$=730.5; melting point: 200° C.

Stage D: (3-{[(3-{3-[(Benzyloxy)carbonyl]-4-[(trifluoroacetyl)amino]benzoyl}-2-methylindolizin-1-yl)amino]carbonyl}phenoxy)acetic acid 17 ml (0.22 mol) of trifluoroacetic acid are added to the suspension of 7.95 g (10.9 mmol) of benzyl 5-[(1-{[3-(2-tert-butoxy-2-oxoethoxy)benzoyl]amino}-2-methylindolizin-3-yl)carbonyl]-2-[(trifluoroacetyl)amino]benzoate in 55 ml of dichloromethane at ambient temperature. The mixture becomes rapidly homogenized. The solution is stirred for 3 hours and concentrated to dryness. The solid obtained is taken up with ethyl ether, filtered and dried. 7.25 g (99%) of an orange powder are obtained.

MH+=674.4; melting point: 239.5° C.

Stage E: 3,3'-{Ethane-1,2-diylbis[imino(2-oxo-ethane-2,1-diyl)oxy-3,1-phenylenecarbonylimino(2-methylindolizine-1,3-diyl)carbonyl]}bis{benzyl 6-[(trifluoroacetyl)amino]benzoate}

0.3 ml (2.2 mmol) of triethylamine and 0.96 g (2.18 mmol) of BOP® are added, at 0° C. under argon, to 1.4 g (2.08 mmol) of (3-{[(3-{3-[(benzyloxy)carbonyl]-4-[(trifluoroacetyl)amino]benzoyl}-2-methylindolizin-1-yl)amino]carbonyl}phenoxy)acetic acid in solution in 8.5 ml of N,N-dimethylformamide. After 15 minutes, 70 µl (1.04 mmol) of ethane-1,2-diamine are added. The reaction medium is stirred at ambient temperature for 24 hours; it thickens to give a gel (after 1 hour, 4.5 ml of N,N-dimethylformamide are added). The reaction medium is diluted with ethyl acetate and washed with a saturated aqueous solution of sodium bicarbonate. A precipitate forms, it is filtered and washed with water and with ethanol and then dried. 0.72 g of a yellow powder is obtained.

$MH^+$=1371.6.

Stage F: 3,3'-{Ethane-1,2-diylbis[imino(2-oxo-ethane-2,1-diyl)oxy-3,1-phenylenecarbonylimino(2-methylindolizine-1,3-diyl)carbonyl]}bis(6-aminobenzoic acid)

0.52 ml (1.04 mmol) of sodium hydroxide (2 M) is added to the solution of 316 mg (0.23 mmol) of the dimer obtained in stage E above in 4 ml of 1-methyl-2-pyrrolidinone. The solution is stirred at ambient temperature for 3 days. The reaction medium is poured into acetone. The precipitate obtained is filtered and then dissolved in 100 ml of water, to which 140 mg of potassium hydrogen carbonate are added. The mixture is lyophilized. The residue obtained is purified by steric exclusion chromatography on Sephadex® LH20 gel (N,N-dimethylformamide). 153 mg of a yellow powder are obtained.

MH+=999.6.

Stage G 0.30 ml of a molar solution of sodium hydroxide is added to the suspension of 153 mg (0.15 mmol) of the dicarboxylic acid obtained in the preceding stage F in 1.5 ml of methanol. The solution is concentrated to dryness and the solid obtained is then taken up in acetone, filtered and dried. 155 mg of a yellow powder are obtained (disodium salt, $5H_2O$).

melting point: 349-354° C. (decomposition). $^1$H-NMR [$(CD_3)_2SO$, 250 MHz]: 10.02 (2H, s), 9.13 (2H, d), 8.26 (2H, t), 8.18 (2H, s), 7.67-7.69 (4H, m), 7.42-7.49 (4H, m), 7.37

(2H, d), 7.18 (2H, d), 7.06 (2H, dd), 7.00-8.00 (4H, broad s), 6.85 (2H, dd), 6.66 (2H, d), 4.59 (4H, s), 3.10-3.20 (4H, m), 1.97 (6H, s).

EXAMPLES 45 TO 47

By following the processes described in stages E to G of Example 44, Examples 45 to 47 are prepared by dimerization of (3-{[(3-{3-[(benzyloxy)carbonyl]-4-[(trifluoroacetyl)amino]benzoyl}-2-methylindolizin-1-yl)amino]carbonyl}phenoxy)acetic acid (stage D of Example 44) with the appropriate commercial diamines.

EXAMPLES 48 AND 49

By following the processes described in stages E to G of Example 44, Examples 48 and 49 are prepared by dimerization of 3-(4-amino-3-methoxybenzoyl)-1-[3-(methoxycarbonyl)phenyl]imidazo[1,5-a]pyridine-7-carboxylic acid (compound obtained by adapting the protocols described in patent application WO2006097625) with the appropriate commercial diamines.

EXAMPLE 50

By following the processes described in stages E to G of Example 44, Example 50 is prepared by dimerization of 3-[7-(ethoxycarbonyl)-3-{3-methoxy-4-[(trifluoro-acetyl)amino]benzoyl}imidazo[1,5-a]pyridin-1-yl]benzoic acid (compound obtained by adapting the protocols described in patent application WO2006097625) with the appropriate commercial diamine.

EXAMPLE 51

Disodium salt of 3,3'-{ethane-1,2-diylbis-[oxy-3,1-phenylenecarbonylimino(2-methylindolizine-1,3-diyl)carbonyl]}bis(benzoic acid)

Stage A: Methyl 2-amino-5-[(1-{[3-(2-hydroxyethoxy)benzoyl]amino}-2-methylindolizin-3-yl)carbonyl]benzoate 0.043 g (0.99 mmol) of sodium hydride (55% dispersion in oil) is added portionwise to the solution of 0.4 g (0.90 mmol) of methyl 2-amino-5-({1-[(3-hydroxybenzoyl)amino]-2-methylindolizin-3-yl}carbonyl)benzoate (stage B of Example 35) in 4.5 ml of N,N-dimethylformamide under argon at 0° C. After 30 minutes, 0.12 ml (1.08 mmol) of 2-bromoethyl acetate is added and the mixture is heated at 70° C. for 1 hour.

The reaction medium is poured into a molar solution of hydrochloric acid and the mixture is extracted with ethyl acetate. The organic phase is washed with a saturated aqueous solution of sodium bicarbonate and a saturated aqueous solution of sodium chloride, dried over sodium sulphate and concentrated under reduced pressure. 0.35 g (76%) of a yellow powder is obtained (MH$^+$=530.1), which powder is suspended in 100 ml of N,N-dimethylformamide and 20 ml of methanol, to which 0.043 g (0.31 mmol) of potassium carbonate is added. The mixture is stirred at ambient temperature for 3 days, and concentrated to dryness. The residue obtained is washed thoroughly with water and dried, to give 0.30 g (95%) of a yellow powder.

MH$^+$=488.2.

Stage B: Methyl 2-amino-5-({2-methyl-1-[(3-{2-[(methylsulphonyl)oxy]ethoxy}benzoyl)amino]indoliz in-3-yl}carbonyl)benzoate 59 µl (0.77 mmol) of mesyl chloride are added to the solution of 0.34 g (0.69 mmol) of methyl 2-amino-5-[(1-{[3-(2-hydroxyethoxy)benzoyl]amino}-2-methylindolizin-3-yl)carbonyl]benzoate in 9 ml of pyridine at −20° C. under nitrogen. The reaction mixture is stirred for 2 hours at −20° C. and is then run into 100 ml of water. The precipitate obtained is filtered, washed thoroughly with water and dried under vacuum, to give 268 mg (70%) of a yellow powder.

melting point: 171° C., MH+=566.1.

Stage C: 3,3'-{Ethane-1,2-diylbis[oxy-3,1-phenylenecarbonylimino(2-methylindolizine-1,3-diyl)carbonyl]}bis(methyl 6-aminobenzoate)

0.21 g (0.48 mmol) of sodium hydride (60% dispersion in oil) is added to the solution of 0.21 g (0.48 mmol) of methyl 2-amino-5-({1-[(3-hydroxybenzoyl)amino]-2-methylindolizin-3-yl}carbonyl)benzoate (stage B of Example 35) in 15 ml of N,N-dimethylformamide at 0° C. under argon. The reaction medium becomes red. After 15 minutes, 0.25 mg (0.44 mmol) of the compound obtained in stage B above in solution in 3 ml of N,N-dimethylformamide is added. The mixture is heated at 60° C. for 12 hours. The reaction medium is allowed to return to ambient temperature and is then run into a saturated aqueous solution of potassium hydrogen sulphate. The precipitate obtained is filtered, washed thoroughly with water and dried under vacuum, and the residue obtained is purified by steric exclusion chromatography on Sephadex® LH20 gel (N,N-dimethylformamide). 220 mg (54%) of a yellow powder are obtained.

melting point: 278° C. (decomposition), MH$^+$=913.6.

Stage D 0.24 ml of sodium hydroxide (2 M) is added to 0.21 g (0.24 mmol) of the dimer obtained in stage E above in 5 ml of 1-methyl-2-pyrrolidinone and the mixture is stirred at ambient temperature for 72 hours. The reaction medium is poured into 150 ml of acetone. The yellow precipitate is filtered and dried, to give 73 mg (30%) of a yellow powder (disodium salt, 6.35H$_2$O).

melting point: 286° C.

$^1$H-NMR [(CD$_3$)$_2$SO, 250 MHz]: 9.97 (2H, s), 9.12 (2H, d), 8.21 (2H, s), 7.65-7.75 (2H, m), 7.35-7.51 (8H, m), 7.00-8.00 (4H, broad s), 7.25 (2H, dd), 7.07 (2H, dd), 6.82 (2H, dd), 6.63 (2H, d), 4.49 (4H, s), 1.98 (6H, s).

EXAMPLE 52

Disodium salt of 3,3'-[octane-1,8-diylbis(oxy-3,1-phenylenecarbonyliminoimidazo[1,5-a]-pyridine-1,3-diylcarbonyl)]bis(6-aminobenzoic acid)

Stage A: Methyl 2-amino-5-({1-[(diphenylmethylene)amino]imidazo[1,5-a]pyridin-3-yl}carbonyl) benzoate 3.83 g (11.75 mmol) of caesium carbonate, 0.73 g (1.18 mmol) of (±)-2,2'-bis(diphenylphosphino)-1,1'-binaphthyl [Binap], 4.93 ml (29.4 mmol) of benzophenoneimine and 0.54 mg (0.59 mmol) of tris(dibenzylideneacetone)dipalladium(0) [Pd₂(dba)₃] are added to the solution of 2.20 g (5.88 mmol) of methyl 2-amino-5-[(1-bromoimidazo[1,5-a]pyridin-3-yl)carbonyl]benzoate (described in Patent Application WO2006097625) in 35 ml of anhydrous N,N-dimethylformamide under argon, and the mixture is then heated at 110° C. for 3 hours. The reaction medium is then filtered and then diluted with ethyl acetate. The organic phase is washed with water and then with a saturated aqueous solution of sodium chloride. It is dried over sodium sulphate, filtered and concentrated to dryness so as to obtain a red solid. After purification by flash chromatography on silica gel (toluene/ethyl acetate/triethylamine gradient=98/1/1 to 90/9/1), 1.18 g (42%) of an orangey-red powder are obtained.

MH⁺=475.3.

Stage B: Methyl 2-amino-5-[(1-aminoimidazo[1,5-a]-pyridin-3-yl)carbonyl]benzoate hydrochloride 8 ml of hydrochloric ethyl ether (1 M) are added to the solution of 1.92 g (4.05 mmol) of the imine obtained in stage A above in a mixture of 40 ml of dichloromethane and 8 ml of methanol. The clear orange medium becomes dark red and then a precipitate forms. After 1 hour at ambient temperature, the precipitate is filtered and then washed with dichloromethane and dried under vacuum at 50° C., to give 1.18 g (84%) of the hydrochloride in the form of an ochre powder.

MH+=311.2.

Stage C: 3,3'-[Octane-1,8-diylbis(oxy-3,1-phenylenecarbonyliminoimidazo[1,5-a]pyridine-1,3-diylcarbonyl)]bis(methyl 6-aminobenzoate)

0.35 ml (2.5 mmol) of triethylamine, 0.63 g (1.2 mmol) of PyBOP and 0.50 g (1.44 mmol) of methyl 2-amino-5-[(1-aminoimidazo[1,5-a]pyridin-3-yl)carbonyl]benzoate are added successively, under a stream of nitrogen, to the solution of 0.20 g (0.48 mmol) of 3,3'-[octane-1,8-diylbis(oxy)]dibenzoic acid (Example R12) in 2.5 ml of N-methylpyrrolidinone. After stirring at ambient temperature for 3 days, 0.13 g (0.24 mmol) of PyBOP is added. After 24 hours, the reaction medium is poured into hydrochloric acid (1M). The brown precipitate formed is washed with water and then dried under vacuum at 50° C. The crude product is dissolved in the minimum amount of N,N-dimethylformamide and purified by steric exclusion chromatography on Sephadex® LH20 gel (N,N-dimethylformamide). 0.34 g (71%) are obtained in the form of a brown powder.

MH+=1001.8; melting point: 187-207° C.

Stage D: 3,3'-[Octane-1,8-diylbis(oxy-3,1-phenylenecarbonyliminoimidazo[1,5-a]pyridine-1,3-diyl-carbonyl)]bis(6-aminobenzoic acid)

0.53 ml of sodium hydroxide (1 M) is added to the solution of 0.24 g (0.24 mmol) of the dimer obtained in stage C above in 1.5 ml of 1-methyl-2-pyrrolidinone. The solution is stirred at ambient temperature for 3 days. Since the reaction is not complete, 0.24 ml of sodium hydroxide (1 M) is added and then, after 24 hours, the reaction medium is poured into a solution of hydrochloric acid (0.1 M). The yellow precipitate formed is filtered and dried and then purified by HPLC chromatography on Kromasyl C18 10µ gel [gradient of eluent A (80% water/20% 0.1 M aqueous solution of ammonium acetate)/eluent B (80% acetonitrile/20% 0.1 M aqueous solution of ammonium acetate)=65/35 to 35/65]. 40 mg (18%) of a yellow powder are obtained.

MH+=943.4.

Stage E 0.07 ml of sodium hydroxide (1 M) is added to the suspension of 34 mg (0.04 mmol) of the dicarboxylic acid obtained in stage D above. The solution is concentrated and the solid obtained is taken up with acetone. The insoluble material is filtered and dried under vacuum at 50° C., so as to obtain 33 mg of a yellow powder (disodium salt, 4.95 mol of water).

melting point: 249° C.

¹H-NMR [(CD₃)₂SO, 250 MHz]: 10.84 (2H, s), 9.66 (2H, d), 8.82 (2H, s), 8.28 (2H, d), 7.63 (2H, d), 7.66-7.74 (4H, m), 7.43 (2H, dd), 7.11-7.22 (6H, m), 7.00-8.00 (4H, broad s), 6.55 (2H, d), 4.07 (4H, t), 1.70-1.85 (4H, m), 1.30-1.50 (8H, m).

EXAMPLE 53

Disodium salt of 3,3'-{ethane-1,2-diyl-bis[imino(2-oxoethane-2,1-diyl)oxy-3,1-phenylene-carbonyliminoimidazo[1,5-a]pyridine-1,3-diylcarbonyl]}-bis(6-aminobenzoic acid)

By following the processes described in stages C to E of Example 52, Example 53 is prepared by dimerization of methyl 2-amino-5-[(1-aminoimidazo[1,5-a]pyridin-3-yl)carbonyl]benzoate (described in stage B of Example 53) with 3,3'-{ethane-1,2-diylbis[imino(2-oxoethane-2,1-diyl)oxy]}dibenzoic acid (Example R13).

MH+=973.2; melting point: 281-286° C.

EXAMPLE 54

L-Lysine salt of 1,1'-[octane-1,8-diyl-bis(oxy-3,1-phenylenecarbonylimino)]bis[3-(4-amino-3-methoxybenzoyl)imidazo[1,5-a]pyridine-7-carboxylic acid]

Stage A: Ethyl 1,1'-[octane-1,8-diylbis(oxy-3,1-phenylenecarbonylimino)]bis(3-{3-methoxy-4-[(trifluoro-acetyl)amino]benzoyl}imidazo[1,5-a]pyridine-7-carboxylate)

1.24 ml (15.5 mmol) of pyridine are added to the suspension of 1.0 g (2.59 mmol) of 3,3'-[octane-1,8-diylbis(oxy)]dibenzoic acid (Example R12) in suspension in 26 ml of dichloromethane. The reaction medium becomes homogeneous. 0.66 ml (7.77 mmol) of cyanogen fluoride is added. The reaction is exothermic and the formation of a white precipitate is observed. After stirring at ambient temperature for 3 hours, the reaction medium is run into a saturated aqueous solution of sodium bicarbonate, and extracted with dichloromethane. The organic phase is washed with a saturated aqueous solution of sodium chloride, dried over sodium sulphate and concentrated to dryness. The colourless oil obtained crystallizes to give 0.88 g (83%) of a white solid.

0.43 ml (5.32 mmol) of pyridine is added to the solution of 0.6 g (1.33 mmol) of ethyl 1-amino-3-{3-methoxy-4-[(trifluoroacetyl)amino]benzoyl}imidazo-[1,5-a]pyridine-7-carboxylate (obtained by adapting the protocols described in patent application WO 2006/097625) in 14 ml of N,N-dimethylformamide, and then the solution is cooled to 0° C. before adding 0.42 ml (4.0 mmol) of trimethylchlorosilane. The mixture is stirred for 30 min and then 0.25 g (0.67 mmol) of the acid difluoride described above is added. The mixture is stirred for 5 days at 50° C. The reaction medium is run into a saturated aqueous solution of potassium sulphate. The red precipitate obtained is filtered and dried under vacuum and then purified by steric exclusion chromatography on Sephadex® LH20 gel (N,N-dimethylformamide). 0.42 g (49%) of a red powder is obtained.

0.26 g (1.91 mmol) of potassium carbonate is added to the solution of 0.40 g (0.32 mmol) of the compound obtained in stage A above in 1 ml of water and of 1 ml of methanol. The reaction mixture is stirred at ambient temperature for 5 days and then poured into an aqueous solution of potassium sulphate. The precipitate formed is filtered, washed with water and dried under vacuum at 50° C. The product is purified by FPLC chromatography on C8 Kromasyl 10μ gel [gradient of methanol/0.02 M aqueous solution of ammonium acetate/acetonitrile=5/95/0 to 45/5/50]. A yellow wax is obtained, which is dissolved in the minimum amount of N,N-dimethylformamide, and the solution is run into 200 ml of water. The precipitate obtained is filtered, washed with water and dried under vacuum at 50° C., to give 7 mg of a red powder.

$MH^+$=1003.2.

Stage C 0.003 g (0.02 mmol) of L-lysine is added to the suspension of 0.01 g (0.01 mmol) of the compound obtained in stage C above in 1 ml of water. The solution is concentrated to dryness and the solid is taken up in acetone, filtered and dried under vacuum, to give an orange powder.

$MH^+$=1003.2 with RT=15.34 min (method A).

EXAMPLE 55

4,4'-{Ethane-1,2-diylbis[imino(2-oxoethane-2,1-diyl)oxy]}bis{N-[3-(4-amino-3-methoxybenzoyl)-2-methylindolizin-1-yl]benzamide}hydrochloride Stage A: 4,4'-{Ethane-1,2-diylbis[imino(2-oxoethane-2,1-diyl)oxy]}bis{N-[3-(4-amino-3-methoxybenzoyl)-2-methylindolizin-1-yl]benzamide}

0.12 ml (0.85 mmol) of triethylamine and 0.38 g (0.85 mmol) of BOP® are added successively to the suspension of 0.17 g (0.40 mmol) of 4,4'-{ethane-1,2-diylbis[imino(2-oxoethane-2,1-diyl)oxy]}dibenzoic acid (Example R14) in 4 ml of N,N-dimethylformamide. After 20 minutes, 0.24 g (0.81 mmol) of (4-amino-3-methoxyphenyl) (1-amino-2-methylindolizin-3-yl)methanone (described in Patent Application WO2003084956) is added portionwise. The reaction medium is stirred at ambient temperature for 20 hours and then 0.38 g (0.85 mmol) of BOPO is added. After 5 hours, the reaction medium is poured into water and extracted with ethyl acetate. The organic phase is washed with a saturated solution of sodium chloride, dried over sodium sulphate and concentrated to dryness. The residue obtained is purified by steric exclusion chromatography on Sephadex® LH20 gel (N,N-dimethylformamide). 41 mg (43%) of a brown powder are obtained.

$MH^+$=971.3.

Stage B 0.10 ml of hydrochloric ethyl ether (1 M) is added to the suspension of 40 mg (0.04 mmol) of the dimer obtained in the preceding stage. The solution is concentrated to dryness and the solid obtained is taken up in acetone. The insoluble material is filtered and dried under vacuum at 50° C., to give 40 mg of a brown powder.

melting point: 223° C.

$^1$H-NMR [$(CD_3)_2SO$, 250 MHz]: 9.83 (2H, s), 9.30 (2H, d), 8.20-8.40 (2H, m), 8.04 (4H, d), 6.85-7.41 (16H, m), 5.00-6.00 (6H, broad s), 4.60 (4H, s), 3.87 (6H, s), 3.25-3.35 (4H, m), 1.89 (6H, s).

EXAMPLES 56 TO 63

By following the processes described in stages A and B of Example 55, Examples 56 to 63 are prepared by dimerization of (4-amino-3-methoxyphenyl)(1-amino-2-methylindolizin-3-yl)methanone (described in patent application WO2003084956) with the appropriate dicarboxylic acid (Examples R14 to R22).

EXAMPLE 64

Disodium salt of 3,3'-ethane-1,2-diylbis-[imino(2-oxoethane-2,1-diyl)oxy-4,1-phenylenecarbonylimino (2-methylindolizine-1,3-diyl)carbonyl]}bis(6-aminobenzoic acid)

Stage A: 3,3'-{Ethane-1,2-diylbis[imino(2-oxoethane-2,1-diyl)oxy-4,1-phenylenecarbonylimino(2-methylindolizine-1,3-diyl)carbonyl]}bis{benzyl 6-[(trifluoroacetyl)amino]benzoate}

0.55 ml (4.0 mmol) of triethylamine and 0.93 g (2.1 mmol) of BOP® are added to 0.40 g (0.96 mmol) of 4,4'-{ethane-1,2-diylbis[imino(2-oxoethane-2,1-diyl)oxy]}dibenzoic acid (Example R14) in solution in 10 ml of N,N-dimethylformamide. After 15 minutes, 0.95 g (1.92 mmol) of benzyl 5-[(1-amino-2-methylindolizin-3-yl)carbonyl]-2-[(trifluoroacetyl) amino]benzoate (described in Patent WO2003084956) is added. The reaction medium is stirred at ambient temperature for 7 hours. The gel obtained is diluted with N,N-dimethylformamide and the insoluble material is filtered, washed with N,N-dimethylformamide and ethyl acetate and then dried under vacuum, to give 570 mg of an orangey yellow solid.

$MH^+$=1376.6 (−1 uma).

Stage B: 3,3'-{Ethane-1,2-diylbis[imino(2-oxoethane-2,1-diyl)oxy-4,1-phenylenecarbonylimino(2-methylindolizine-1,3-diyl)carbonyl]}bis(6-aminobenzoic acid)

1.46 ml of sodium hydroxide (1 M) are added to the solution of 0.57 g (0.42 mmol) of the dimer obtained in stage A above in 8 ml of 1-methyl-2-pyrrolidinone. The solution is stirred at ambient temperature for 3 days. The reaction medium is poured into 200 ml of water containing 400 mg of potassium hydrogen sulphate. The insoluble material is filtered and dried before being purified by steric exclusion chromatography on Sephadex® LH20 gel (N,N-dimethylformamide). 153 mg of a yellow powder are obtained.

$MH^+$=999.6.

Stage C

The product is salified by the addition of 0.35 ml of sodium hydroxide (1M) to the suspension of 0.18 g (0.15 mmol) of the dicarboxylic acid obtained in stage B above in 2 ml of methanol. The solution is concentrated to dryness and then the solid obtained is taken up in acetone, filtered and dried. 162 mg of a yellow powder are obtained (disodium salt, $5H_2O$).

melting point: 290-297° C. (decomposition).

$^1$H-NMR [(CD$_3$)$_2$SO, 250 MHz]: 9.87 (2H, s), 9.12 (2H, d), 8.37 (2H, broad t), 8.21 (2H, s), 8.06 (4H, d), 7.50-8.00 (4H, broad s), 7.38-7.44 (4H, m), 7.00-7.12 (6H, m), 6.83 (2H, dd), 6.63 (2H, d), 4.60 (4H, s), 3.25-3.40 (4H, m), 1.96 (6H, s).

EXAMPLES 65 TO 70

By carrying out the procedure according to the processes described in stages E to G of Example 64, Examples 65 to 70 are prepared by dimerization of methyl 2-amino-5-[(1-amino-2-methylindolizin-3-yl)carbonyl]benzoate (described in Patent WO2003084956) with the appropriate dicarboxylic acids (Examples R23 to R28).

EXAMPLE 71

By carrying out the processes described in stages A to C of Example 64, Example 71 is prepared by dimerization of methyl 3-[(1-amino-2-methylindolizin-3-yl)carbonyl]-benzoate (compound obtained by adapting the protocols described in patent application WO 2003/084956) with 3,3'-{ethane-1,2-diylbis[imino(2-oxoethane-2,1-diyl)oxy]}dibenzoic acid (Example R13).

Melting point: 330-339° C.
$^1$H NMR [(CD$_3$)$_2$SO, 400 MHz]: 10.10 (2H, s), 9.61 (2H, d) 8.41 (2H, broad s), 8.00-8.10 (4H, m), 7.62-7.70 (4H, m), 7.57 (2H, d), 7.38-7.48 (6H, m), 7.23 (2H, dd), 7.15 (2H, dd), 7.00 (2H, dd), 4.56 (4H, s), 3.26 (4H, m), 1.71 (6H, s).

EXAMPLE 72

Disodium salt of 3,3'-{1,3-phenylene-bis[sulphonyliminoethane-2,1-diyloxy-3,1-phenylene-carbonylimino(2-methylindolizine-1,3-diyl)carbonyl]}-bis(6-aminobenzoic acid)

1.35 ml (9.6 mmol) of triethylamine is added, at ambient temperature and under a nitrogen atmosphere, to a suspension of 0.30 g (0.77 mmol) of 2-amino-5-[(1-amino-2-methylindolizin-3-yl)carbonyl]benzoic acid hydrogen sulphate in 4 ml of tetrahydrofuran. The reaction medium is heterogeneous. It is then cooled to 0° C. and 0.52 ml (4.1 mmol) of trimethylsilyl chloride is slowly added. The reaction medium changes colour from orange to green and remains heterogeneous.

In parallel, 0.20 ml (1.38 mmol) of triethylamine and then 0.40 g (0.76 mmol) of PyBOP are added, at ambient temperature and under a nitrogen atmosphere, to a suspension of 0.20 g (0.34 mmol) of 3,3'-[1,3-phenylenebis(sulphonyliminoethane-2,1-diyloxy)]dibenzoic acid in 2.7 ml of N,N-dimethylformamide. The reaction medium is stirred for 40 minutes and is then added, via a cannula, to the suspension of the silylated amine. After stirring for 20 hours, the reaction mixture is poured into 30 ml of water and 0.54 ml of concentrated sulphuric acid. The precipitate obtained is filtered, and washed with water to neutral pH. The product is purified by FPLC chromatography on C8 Kromasyl 10µ gel [gradient of methanol/0.02 M aqueous solution of ammonium acetate/acetonitrile=5/95/0 to 45/5/50]. 140 mg of a yellow wax are obtained, which wax is dissolved in the minimum amount of N,N-dimethylformamide and this solution is run into 200 ml of water. The precipitate obtained is filtered, washed with water and dried under vacuum at 50° C., to give a yellow powder.

The dicarboxylic acid obtained is salified by adding 2 equivalents of a molar solution of sodium hydroxide; after concentration and drying of the powder under vacuum at 50° C., a yellow powder is obtained (disodium salt, 8 mol of water).

Melting point: 308° C.
$^1$H NMR [(CD$_3$)$_2$SO, 400 MHz]: 10.02 (2H, broad s), 9.10 (2H, d), 8.15-8.19 (4H, m), 7.85 (2H, d), 7.55-7.65 (6H, m), 7.35-7.42 (6H, m), 6.95-7.05 (4H, m), 6.78 (2H, dd), 6.60 (2H, d), 3.98 (4H, broad t), 3.13 (4H, broad t), 1.94 (6H, s) (the —NH$_2$ protons give a broad signal 6.0-9.0 ppm).

EXAMPLES 73 TO 104

By carrying out the process according to the protocol described in Example 72, Examples 73 to 104 are prepared by dimerization of 2-amino-5-[(1-amino-2-methylindolizin-3-yl)carbonyl]benzoic acid (compound obtained by adapting the protocols described in patent application WO 2003/084956) with the appropriate dicarboxylic acid (Examples R31 to R37, R18 and R38 to R61, respectively).

EXAMPLE 105

Stage A: Benzyl 5-{[1-({3-[2-(glycylamino)ethoxy]-benzoyl}amino)-2-methylindolizin-3-yl]carbonyl}-2-[(trifluoroacetyl)amino]benzoate By following the process described in stage G of Example 42, the coupling of benzyl 5-[(1-{[3-(2-aminoethoxy)benzoyl]amino}-2-methylindolizin-3-yl)carbonyl]-2-[(trifluoroacetyl)amino]benzoate (described in stage F, Example 42) with N-tert-butoxycarbonylglycine is carried out. The compound obtained is then deprotected with trifluoroacetic acid to give the amine according to the process described in stage F of Example 42.

MH$^+$=716.1.

Stage B: Benzyl 5-{[1-({3-[2-({[({3-[(3-{3-[(benzyloxy)carbonyl]-4-[(trifluoroacetyl)amino]benzoyl}-2-methylindolizin-1-yl)carbamoyl]phenoxy}acetyl)amino]acetyl}-amino)ethoxy]benzoyl}amino)-2-methylindolizin-3-yl]-carbonyl}-2-[(trifluoroacetyl)amino]benzoate By following the process described in stage G of Example 42, the coupling of the amine obtained in stage A above with (3-{[(3-{3-[(benzyloxy)carbonyl]-4-[(trifluoroacetyl)amino]benzoyl}-2-methylindolizin-1-yl)amino]carbonyl}phenoxy)acetic acid (described in stage D of Example 44) is carried out.

MH$^+$=1371.3.

Stage C

By following the processes described in stages B and C of Example 8, the deprotection of the compound obtained in stage A above is carried out, followed by the salification of the dicarboxylic acid with sodium hydroxide (disodium salt, 6.2 mol of water).

Melting point: 313-318° C.
$^1$H NMR [(CD$_3$)$_2$SO, 400 MHz]: 9.99 (2H, d), 9.15 (2H, d), 8.40 (1H, t), 8.24 (1H, t), 8.15 (2H, d), 7.61-7.69 (4H, m), 7.36-7.49 (6H, m), 7.21 (1H, d), 7.14 (1H, d), 7.07 (2H, dd), 6.83 (2H, dd), 6.69 (2H, d), 4.65 (2H, s), 4.08 (2H, t), 3.81 (2H, d), 3.48 (2H, m), 1.95 (6H, s) (the —NH$_2$ protons give a broad signal 6.0-9.0 ppm).

EXAMPLE 106

Disodium salt of 3,3'-{ethane-1,2-diylbis-[oxy-ethane-2,1-diyloxy-4,1-phenylene(2-methylindolizine-1,3-diyl)carbonyl]}bis(6-aminobenzoic acid)

Stage A: 3,3'-{Ethane-1,2-diylbis[oxyethane-2,1-diyloxy-4,1-phenylene(2-methylindolizine-1,3-diyl)-carbonyl]}bis(methyl 6-aminobenzoate)

5.42 ml of a solution of potassium phosphate (1 M) and 132 mg (0.18 mmol) of $PdCl_2$(dppf) are added to the solution of 0.70 g (1.81 mmol) of methyl 2-amino-5-[(1-bromo-2-methylindolizin-3-yl)carbonyl]benzoate (described in Patent Application WO20055028476) and 0.51 g (0.92 mmol) of 2,2'-[ethane-1,2-diylbis(oxyethane-2,1-diyloxy-4,1-phenylene)]bis(4,4,5,5-tetramethyl-1,3,2-dioxaborolane) (Example R65) in 26 ml of degassed dimethoxyethane. The mixture is heated at 100° C. for 24 hours and 66 mg of $PdCl_2$(dppf) are added after 6 hours. The reaction mixture is diluted with dichloromethane and filtered. The filtrate is washed with water and dried over sodium sulphate and concentrated to dryness. The solid obtained is purified by flash chromatography on silica gel (diisopropyl ether/methanol gradient=100/0 to 90/10). 437 mg (53%) of a yellow solid are obtained.

$MH^+$=915.3; melting point: 186° C.

Stage B: 3,3'-{Ethane-1,2-diylbis[oxyethane-2,1-diyloxy-4,1-phenylene(2-methylindolizine-1,3-diyl)carbonyl]}bis(6-aminobenzoic acid)

The solution of 0.42 g (0.46 mmol) of the dimer obtained in stage A above in the presence of 1.38 ml of sodium hydroxide (1 M) in 5 ml of methanol and 5 ml of 1,4-dioxane is refluxed for 5 hours. The reaction mixture is heterogeneous, it is diluted with methanol and water until a solution is obtained, which is run into 150 ml of water containing 182 mg of potassium hydrogen sulphate. The precipitate obtained is filtered and washed thoroughly with water and then dried under vacuum at 50° C., to give 0.36 g (88%) of an orangey brown powder.

MH+=887.2.

Stage C 0.59 ml of sodium hydroxide (1 M) is added to the suspension of 0.27 g (0.30 mmol) of the dicarboxylic acid obtained in stage B above in 50 ml of methanol. The solution is concentrated to dryness. The solid obtained is taken up in acetone, filtered and dried under vacuum at 50° C., to give 0.25 g (88%) of a yellow powder (disodium salt, 4 mol of water).

melting point: 257° C.

$^1$H-NMR [$(CD_3)_2SO$, 250 MHz]: 9.02 (2H, d), 8.22 (2H, s), 7.43 (4H, d), 7.33 (4H, d), 7.00-8.00 (4H, broad s), 6.97-7.09 (6H, m), 6.78 (2H, dd), 6.60 (2H, d), 4.17 (4H, t), 3.81 (4H, t), 3.68 (4H s), 2.03 (6H, s).

EXAMPLES 107 TO 109

By carrying out the procedure according to the processes described in stages A to C of Example 106, Examples 107 to 109 are prepared by dimerization of methyl 2-amino-5-[(1-bromo-2-methylindolizin-3-yl)carbonyl]benzoate (described in Patent Application WO20055028476) with the appropriate boronic diesters or diboronic acids (Examples R66 to R68).

EXAMPLE 110

Disodium salt of 3,3'-{ethane-1,2-diylbis-[imino(2-oxoethane-2,1-diyl)oxy-3,1-phenylene(2-methyl-indolizine-1,3-diyl)carbonyl]}bis(6-aminobenzoic acid)

Stage A: Methyl 2-amino-5-({1-[3-(2-tert-butoxy-2-oxoethoxy)phenyl]-2-methylindolizin-3-yl}carbonyl)benzoate The mixture of 2.78 g (7.18 mmol) of methyl 2-amino-5-[(1-bromo-2-methylindolizin-3-yl)carbonyl]benzoate (described in Patent Application WO2005028476), 3.6 g (10.8 mmol) of tert-butyl[3-(4,4,5,5-tetramethyl-1,3,2-dioxaborolan-2-yl)phenoxy]acetate (CAS 769968-18-5; described in Patent Application WO2004084813), 0.73 g (1.0 mmol) of $PdCl_2$(dppf) in 22 ml of a molar solution of potassium phosphate and 100 ml of 1,2-dimethoxyethane is heated at 100° C. under argon. After 2 hours and 4 hours, a further 100 mg of $PdCl_2$(dppf) are added. After 6 hours at 100° C. under argon, the reaction medium is allowed to return to ambient temperature and is then filtered. The organic solution is washed with water and with a saturated solution of sodium chloride, dried over sodium sulphate and concentrated to dryness. The residue obtained is purified by flash chromatography on silica gel (dichloromethane/diisopropyl ether gradient=100/0 to 0/100), to give 2.84 g (77%) of a yellow powder.

$MH^+$=515.2; melting point: 81° C.

Stage B: (3-{3-[4-Amino-3-(methoxycarbonyl)-benzoyl]-2-methylindolizin-1-yl}phenoxy)acetic acid The solution of 3.68 g (6.65 mmol) of methyl 2-amino-5-({1-[3-(2-tert-butoxy-2-oxoethoxy)phenyl]-2-methylindolizin-3-yl}carbonyl)benzoate in 11 ml of trifluoroacetic acid and 35 ml of dichloromethane at ambient temperature for 4 hours. The reaction medium is poured into water and the mixture is extracted with dichloromethane. The organic phase is partially concentrated, and the yellow precipitate formed is filtered and washed with diisopropyl ether and then dried, to give 2.75 g (92%) of a yellow powder.

$MH^+$=459.2; melting point: 160° C.

Stage C: 3,3'-{Ethane-1,2-diylbis[imino(2-oxoethane-2,1-diyl)oxy-3,1-phenylene(2-methylindolizine-1,3-diyl)carbonyl]}bis(methyl 6-aminobenzoate)

0.55 ml (3.93 mmol) of triethylamine and 1.12 g (2.16 mmol) of PyBOP at 0° C. under argon in 7 ml of N,N-dimethylformamide are added to 0.9 g (1.96 mmol) of 2-amino-5-({1-[3-(carboxymethoxy)phenyl]-2-methylindolizin-3-yl}carbonyl)benzoic acid. After 10 minutes, 66 μl (0.98 mmol) of ethane-1,2-diamine are added. The reaction medium is stirred at ambient temperature for 22 hours and is then poured into water and extracted with ethyl acetate. The organic phase is washed with a saturated aqueous solution of sodium chloride, dried over sodium sulphate and concentrated under reduced pressure. The solid obtained is purified by flash chromatography on silica gel (dichloromethane/methanol=97/3), to give 0.68 g (73%) of a yellow powder.

MH+=941.8; melting point: 165° C.

Stage D: 3,3'-{Ethane-1,2-diylbis[imino(2-oxoethane-2,1-diyl)oxy-3,1-phenylene(2-methylindolizine-1,3-diyl)carbonyl]}bis(6-aminobenzoic acid)

The solution of 0.61 g (0.65 mmol) of the dimer obtained in stage E above and 1.6 ml of sodium hydroxide (1 M) in 11 ml of dimethyl sulphoxide is heated at 100° C. for 10 minutes and is then run into 500 ml of an aqueous solution containing 0.22 g of potassium hydrogen sulphate. The mixture is extracted with ethyl acetate. The organic phase is washed with a saturated aqueous solution of sodium chloride, dried over sodium sulphate and concentrated under reduced pressure. The residue is purified by steric exclusion chromatography on Sephadex® LH20 gel (N,N-dimethylformamide). 424 mg (72%) of a yellow powder are obtained.

MH+=913.7.

Stage E 0.91 ml of sodium hydroxide (1 M) is added to the suspension of 424 mg (0.46 mmol) of the dicarboxylic acid obtained in the preceding stage D in 40 ml of methanol. The solution is concentrated to dryness and the solid obtained is then taken up in acetone, filtered and dried under vacuum at 50° C. 405 mg of a yellow powder are obtained (disodium salt, $4H_2O$).

melting point: 237° C.

$^1$H-NMR [$(CD_3)_2SO$, 250 MHz]: 9.00 (2H, d), 8.50 (2H, broad t), 8.23 (2H, s), 7.36-7.54 (6H, m), 6.92-7.08 (8H, m), 7.00-8.00 (4H, broad s), 6.80 (2H, dd), 6.62 (2H, d), 4.55 (4H, s), 3.25-3.35 (4H, m), 2.06 (6H, s).

EXAMPLE 111

By following the processes described in stages C to E of Example 110, Example 111 is prepared by dimerization of (3-{3-[4-amino-3-(methoxycarbonyl)benzoyl]-2-methylindolizin-1-yl}phenoxy)acetic acid (stage B of Example 110) with hexane-1,6-diamine.

EXAMPLES 112 AND 113

Stage A: 4-{3-[4-Amino-3-(methoxycarbonyl)benzoyl]-2-methylindolizin-1-yl}phenoxy)acetic acid By following the processes described in stages A and B of Example 110, (4-{3-[4-amino-3-(methoxycarbonyl)benzoyl]-2-methylindolizin-1-yl}phenoxy)acetic acid is prepared from tert-butyl[4-(4,4,5,5-tetramethyl-1,3,2-dioxaborolan-2-yl)phenoxy]acetate (CAS 76998-17-4; described in Patent Application WO2004084813) and from methyl 2-amino-5-[(1-bromo-2-methylindolizin-3-yl)carbonyl]benzoate (described in Patent Application WO2005028476).

MH+=459.1; melting point: 239° C.

Stage B

Examples 112 and 113 are obtained by following the processes described in stages C to E of Example 110, by dimerization of (4-{3-[4-amino-3-(methoxycarbonyl)-benzoyl]-2-methylindolizin-1-yl}phenoxy)acetic acid with ethane-1,2-diamine and hexane-1,6-diamine, respectively.

EXAMPLES 114 TO 116

By adapting the processes described in stages A and B of Example 64 then stage C of Example 54, Examples 114 to 116 are prepared by dimerization of methyl 2-amino-5-{[6-(2-aminoethoxy)-1-methoxy-2-methylindolizin-3-yl]carbonyl}-benzoate (compound obtained by adapting the protocols described in Patent Application WO20055028476) with the appropriate dicarboxylic acids (Examples R62 to R64).

Preparation of FGFR Agonist Heterodimers

EXAMPLE 117

Disodium salt of 2-amino-5-[(1-{[3-(2-{[2-({[3-({[3-(4-amino-3-carboxybenzoyl)imidazo[1,5-a]pyridin-1-yl]amino}carbonyl)phenoxy]acetyl}amino)ethyl]amino}-2-oxoethoxy)benzoyl]amino}-2-methylindolizin-3-yl)carbonyl]dibenzoic acid Stage A: 3-{2-[(2-{[(3-{[(3-{3-[(benzyloxy)carbonyl]-4-[(trifluoroacetyl)amino]-benzoyl}-2-methylindolizin-1-yl)amino]carbonyl}-phenoxy)acetyl]amino}ethyl)amino]-2-oxoethoxy}-benzoic acid 0.73 ml (5.23 mmol) of triethylamine, 0.34 g (0.65 mmol) of PyBOP and, after 15 minutes, 0.32 g (0.65 mmol) of benzyl 5-[(1-amino-2-methylindolizin-3-yl)carbonyl]-2-[(trifluoroacetyl)amino]benzoate (described in Patent Application WO03084956) are added successively to 1.1 g (2.62 mmol) of 3,3'-{ethane-1,2-diylbis[imino(2-oxoethane-2,1-diyl)oxy]}dibenzoic acid (Example R13) suspended in 26 ml of dichloromethane. The reaction mixture is stirred at ambient temperature for 4 hours and then poured into a saturated solution of bicarbonate. The precipitate obtained is filtered and then dissolved in water. The aqueous solution is acidified and extracted with ethyl acetate. The organic phase is washed with water and then dried over sodium sulphate and concentrated to dryness. After purification of the solid obtained by steric exclusion chromatography on Sephadex® LH20 gel (N,N-dimethylformamide), 240 mg (41%) of a yellow powder are obtained.

MH+=894.5; melting point: 196.6° C.

Stage B: Methyl 2-amino-5-({1-[(3-{2-[(2-{[(3-{[(3-{3-[(benzyloxy)carbonyl]-4-[(trifluoroacetyl)amino]benzoyl}-2-methylindolizin-1-yl)amino]carbonyl}phenoxy)acetyl]-amino}ethyl)amino]-2-oxoethoxy}benzoyl)amino]imidazo[1,5,-a]pyridin-3-yl}carbonyl)benzoate 0.12 ml (0.78 mmol) of triethylamine, 0.19 g (0.36 mmol) of PyBOP and, after 15 minutes, 135 mg (0.39 mmol) of methyl 2-amino-5-[(1-aminoimidazo[1,5-a]pyridin-3-yl)carbonyl]benzoate hydrochloride (stage B of Example 53) and 6 ml of N,N-dimethylformamide are added successively to 232 mg (0.26 mmol) of the carboxylic acid obtained in stage A above dissolved in 1.2 ml of N,N-dimethylformamide under nitrogen. After stirring at ambient temperature for 4 hours, 0.14 g of PyBOP is added. After 16 hours, the reaction mixture is diluted with N,N-dimethylformamide and filtered.

To the 100 g of solid obtained (activated ester) in solution in 1.5 ml of N,N-dimethylformamide, are added 42 mg of methyl 2-amino-5-[(1-aminoimidazo[1,5-a]pyridin-3-yl)carbonyl]benzoate hydrochloride and 10 µl of triethylamine. At ambient temperature, the reaction does not evolve; the mixture is heated at 60° C. for 48 hours after having added 14 µl of triethylamine and 52 mg of PyBOP. The reaction mixture is filtered and the solid obtained is purified by steric exclusion chromatography on Sephadex® LH20 gel (N,N-dimethylformamide). 51 mg (17%) of a yellow powder are obtained.

MH+=1187.1.

Stage C: 3-{2-[(2-{[(3-{[(3-{3-[(benzyloxy)-carbonyl]-4-[(trifluoroacetyl)amino]benzoyl}-2-methylindolizin-1-yl)amino]carbonyl}phenoxy)-acetyl]amino}ethyl)amino]-2-oxoethoxy}dibenzoic acid 0.2 ml of sodium hydroxide (1 M) is added to the solution of 71 mg (0.06 mmol) of the heterodimer obtained in stage B above in 1.2 ml of dimethyl sulphoxide and the solution is stirred at ambient temperature. After 48 hours, 0.18 ml of sodium hydroxide (1 M) is again added and the mixture is stirred for 24 hours. The solution is then run into a saturated aqueous solution of potassium hydrogen sulphate, and the precipitate obtained is filtered and dried. The solid obtained is purified by steric exclusion chromatography on Sephadex® LH20 gel (N,N-dimethylformamide), to give 24 mg (41%) of a yellow powder.
MH$^+$=986.8.

Stage D 45.5 μl of sodium hydroxide (1 M) are added to the solution of 23 mg (0.02 mmol) of the dimer obtained in stage C above in 30 ml of methanol. The solution is concentrated to dryness and the solid is taken up in acetone. The solid is filtered and dried under vacuum at 50° C. for 48 hours, to give 16 mg (67%) of a yellow powder (disodium salt, 6H$_2$O).
melting point: 278.3° C.
$^1$H-NMR [(CD$_3$)$_2$SO, 250 MHz]: 10.90 (1H, broad s), 10.05 (1H, broad s), 9.68 (1H, d), 9.12 (1H, d), 8.95 (1H, broad s), 8.35-8.60 (2H, m) 8.28 (1H, d), 8.19 (1H, s), 7.00-8.00 (15H, m), 6.81 (1H, dd), 6.61 (2H, dd), 4.61 (2H, s), 4.57 (2H, s), 3.25-3.42 (4H, m) 1.96 (6H s).

EXAMPLE 118

L-Lysine salt of 2-amino-5-({1-[(3-{2-[(2-{[(4-{[3-(4-amino-3-carboxybenzoyl)-2-methylindolizin-1-yl]carbamoyl}phenoxy)acetyl]amino}ethyl)amino]-2-oxoethoxy}benzoyl)amino]-2-methylindolizin-3-yl}carbonyl)benzoic acid By carrying out the stages A and B of Example 72, Example 118 is prepared by dimerization of 2-amino-5-[(1-amino-2-methylindolizin-3-yl)carbonyl]benzoic acid (compound obtained by adapting the protocols described in patent application WO 2003/084956) with 3-{2-[(2-{[(4-carboxyphenoxy)acetyl]amino}ethyl)amino]-2-oxoethoxy}benzoic acid (Example R69).
Melting point: 213° C.
$^1$H NMR [(CD$_3$)$_2$SO, 400 MHz]: 10.05 (1H, broad s), 9.96 (1H, broad s), 9.13 (2H, dd), 9.12 (1H, d), 8.30-8.38 (2H, m), 8.11-8.15 (2H, m), 8.06 (2H, d), 7.70 (2H, d), 7.46-7.50 (4H, m), 7.35 (3H, dd), 7.19 (2H, dd), 7.00-7.09 (4H, m), 6.85-6.77 (2H, m), 6.66 (2H, d), 4.59 (2H, s), 4.56 (2H, s), 3.13 (4H, t), 2.69 (4H, t), 1.95 (3H, s) 1.93 (3H, s), 1.30-1.74 (10H, m).

EXAMPLE 119

Disodium salt of 2-amino-5-({1-[(20-{[3-(4-amino-3-carboxybenzoyl)-1-methoxy-2-methylindolizin-8-yl]oxy}-3,6,9,12,15,18-hexaoxaicos-1-yl)oxy]-2-methylindolizin-3-yl}carbonyl)benzoic acid Stage A: Methyl 2-amino-5-({8-[(20-iodo-3,6,9,12,15,18-hexaoxaicos-1-yl)oxy]-1-methoxy-2-methylindolizin-3-yl}carbonyl)benzoate 12 ml (6.0 mmol) of potassium hexamethyldisilylamide (0.5 M solution in toluene) at −20° C. under nitrogen is added, dropwise, to the solution of 2.0 g (5.64 mmol) of methyl 2-amino-5-[(8-hydroxy-1-methoxy-2-methyl-indolizin-3-yl)carbonyl]benzoate (described in stage F of Example 1) in 56 ml of tetrahydrofuran. The formation of a red precipitate is observed. The mixture is allowed to return to ambient temperature and 18.5 g (33.9 mmol) of 1,20-diiodo-3,6,9,12,15,18-hexaoxaicosane are added (Example R1). The solution is stirred at ambient temperature for 18 hours. The reaction medium is poured into a solution of hydrochloric acid (1 M) and the mixture is extracted with an ethyl acetate/tetrahydrofuran mixture. The organic phase is washed with a saturated aqueous solution of sodium chloride, dried over sodium sulphate and concentrated under reduced pressure. The residue obtained is purified by flash chromatography on silica gel (gradient of dichloromethane/methanol: 100/0 to 90/10). 2.3 g (53%) of a yellow oil are obtained.
MH$^+$=773.1.

Stage B: Methyl 2-amino-5-({1-[(20-{[3-(4-amino-3-carboxybenzoyl)-1-methoxy-2-methylindolizin-8-yl]oxy}-3,6,9,12,15,18-hexaoxaicos-1-yl)oxy]-2-methylindolizin-3-yl}carbonyl)benzoate 3.88 ml (1.94 mmol) of potassium hexamethyldisilylamide (0.5 M solution in toluene) at −20° C. under nitrogen are added, dropwise, to the solution of 0.63 g (1.94 mmol) of methyl 2-amino-5-[(1-hydroxy-2-methylindolizin-3-yl)carbonyl]benzoate (described in patent application WO 2003/084956) in 7 ml of tetrahydrofuran. The formation of a red precipitate is observed, to which 0.5 g (0.65 mmol) of the iodinated derivative obtained in stage A above is added. The solution is stirred at ambient temperature for 18 hours. The reaction medium is poured into a saturated aqueous solution of potassium sulphate and the mixture is extracted with an ethyl acetate/tetrahydrofuran mixture. The organic phase is washed with a saturated aqueous solution of sodium chloride, dried over sodium sulphate and concentrated under reduced pressure. The residue obtained is purified by flash chromatography on silica gel (gradient of dichloromethane/methanol: 100/0 to 90/10). 0.42 g (67%) of a yellow oil is obtained.
MH$^+$=969.3 with RT=22.05 (method A).

Stage C

By carrying out the process described in stages D and E of Example 7, the saponification of the methyl diester obtained in the preceding stage and the salification with sodium hydroxide are carried out (disodium salt, 4.5 mol of water).
Melting point: 280° C.
$^1$H NMR [(CD$_3$)$_2$SO, 400 MHz]: 9.07 (1H, d), 8.60 (1H, d) 8.12 (2H, d), 7.55 (1H, d), 7.34 (2H, dd), 6.96 (1H, dd), 6.71 (1H, ddd), 6.52-6.60 (3H, m), 6.36 (1H, d), 4.22 (2H, broad t), 4.06 (2H, broad t), 3.83 (2H, broad t), 3.76 (3H, s), 3.46-3.67 (22H, m), 1.98 (3H, s), 1.91 (3H, s) (the —NH$_2$ protons give a broad signal 6.0-9.0 ppm).

EXAMPLE 120

Disodium salt of 2-amino-5-({6-[(20-{[3-(4-amino-3-carboxybenzoyl)-1-methoxy-2-methylindolizin-8-yl]oxy}-3,6,9,12,15,18-hexaoxaicos-1-yl)oxy]-1-methoxy-2-methylindolizin-3-yl}carbonyl)benzoic acid By carrying out the process described in stages B and C of Example 119, Example 120 is prepared from methyl 2-amino-5-({8-[(20-iodo-3,6,9,12,15,18-hexaoxaicos-1-yl)oxy]-1-methoxy-2-methylindolizin-3-yl}carbonyl)benzoate (described in stage A of Example 119) and methyl 2-amino-5-[(6-hydroxy-1-methoxy-2-methylindolizin-3-yl)carbonyl]benzoate (described in stage F of Example 11). (Disodium salt, 6.4 mol of water).

Melting point: 274° C.

$^1$H NMR [(CD$_3$)$_2$SO, 400 MHz]: 8.89 (1H, d), 8.60 (1H, d) 8.12 (2H, dd), 7.48 (1H, dd), 7.34 (2H, m), 6.85 (1H, dd), 6.53-6.60 (3H, m), 6.37 (1H, d), 4.21 (2H, broad t), 4.03 (2H, broad t), 3.83 (2H, broad t), 3.80 (3H, s), 3.70-3.77 (5H, m), 3.46-3.65 (20H, m), 1.93 (3H, s), 1.91 (3H, s) (the —NH$_2$ protons give a broad signal 6.0-9.0 ppm).

EXAMPLE 121

Disodium salt of 2-amino-5-({1-[(20-{4-[3-(4-amino-3-carboxybenzoyl)-1-methoxyindolizin-2-yl]-phenoxy}-3,6,9,12,15,18-hexaoxaicos-1-yl)oxy]-2-methyl-indolizin-3-yl}carbonyl)benzoic acid Stage A: Methyl 2-amino-5-[(2-{4-[(20-iodo-3,6,9,12,15,18-hexaoxaicos-1-yl)oxy]phenyl}-1-methoxy-indolizin-3-yl)carbonyl]benzoate By carrying out the process according to the protocol described in stage A of Example 119, methyl 2-amino-5-[(2-{4-[(20-iodo-3,6,9,12,15,18-hexaoxaicos-1-yl)oxy]-phenyl}-1-methoxyindolizin-3-yl)carbonyl]benzoate (brown oil) is prepared by alkylation of methyl 2-amino-5-{[2-(4-hydroxyphenyl)-1-methoxyindolizin-3-yl]carbonyl}benzoate (compound obtained by adapting the protocols described in patent application WO 2003/084956) with 1,20-diiodo-3,6,9,12,15,18-hexaoxaicosane (Example R1).

MH$^+$=835.2 with RT=21.15 min (method A)

Stage B: Methyl 2-amino-5-({1-[(20-{4-[3-(4-amino-3-carboxybenzoyl)-1-methoxyindolizin-2-yl]phenoxy}-3,6,9,12,15,18-hexaoxaicos-1-yl)oxy]-2-methylindolizin-3-yl}carbonyl)benzoate By carrying out the process according to the protocol described in stage B of Example 119, methyl 2-amino-5-({1-[(20-{4-[3-(4-amino-3-carboxybenzoyl)-1-methoxy-indolizin-2-yl]phenoxy}-3,6,9,12,15,18-hexaoxaicos-1-yl)oxy]-2-methylindolizin-3-yl}carbonyl)benzoate (yellow oil) is prepared by alkylation of methyl 2-amino-5-[(1-hydroxy-2-methylindolizin-3-yl)carbonyl]-benzoate (described in patent application WO 2003/084956) with the iodinated derivative obtained in stage A above.

MH$^+$=1031.3 with RT=22.79 min (method A).

Stage C

Same procedure as in stage C of Example 119 (disodium salt, 8 mol of water).

Melting point: 196° C.

$^1$H NMR [(CD$_3$)$_2$SO, 400 MHz]: 9.04 (1H, d), 8.80 (1H, d), 8.13 (2H, dd), 7.56 (2H, dd), 7.33 (1H, dd), 7.13 (2H, d), 7.04 (1H, dd), 6.93-6.96 (2H, m), 6.70-6.76 (4H, m), 6.56 (1H, dd), 6.12 (1H, d), 4.07 (2H, broad t), 4.00 (2H, broad t), 3.62-3.70 (4H, m), 3.60 (3H, s), 3.45-3.59 (20H, m), 1.98 (3H, s) (the —NH$_2$ protons give a broad signal 6.0-9.0 ppm). Preparation and/or References of the Reactants Used in the Dimerization Stages of Examples 1 to 121 Described Above.

EXAMPLE R1

1,20-Diiodo-3,6,9,12,15,18-hexaoxaicosane

CAS 153399-56-5; J.-F. Nierengarten, C. O. Dietrich-Buchecker and J.-P Sauvage, *J. Am. Chem. Soc.*, 1994, 116 (1), 375-376.

EXAMPLE R2

1,17-Diiodo-3,6,9,12,15-pentaoxaheptadecane

CAS 118798-05-3; C. O. Dietrich-Buchecker and J. P. Sauvage, *Angew. Chem.*, 1989, 101(2), 192-19.

EXAMPLE R3

1,14-Diiodo-3,6,9,12-tetraoxatetradecane

CAS 76871-59-5; L. A. Frederick, T. M. Fyles, N. P. Gurprasad, D. M. Whitfield, *Can. J. Chem.* 1981, 59, 1724-1733.

EXAMPLE R4

1-Iodo-2-{2-[2-(2-iodoethoxy)ethoxy]ethoxy}ethane

CAS 36839-56-2; N. K. Dalley, K. E. Krakowiak, J. S. Bradshaw, M. M. England, X. Kou, R. M. Izatt, *Tetrahedron*, 1994, 50 (9), 2721-2728.

EXAMPLE R5

1-Iodo-2-[2-(2-iodoethoxy)ethoxy]ethane

CAS 36839-55-1: commercial

EXAMPLE R6

1-Bromo-2-(2-bromoethoxy)ethane

CAS 5414-19-7: commercial

EXAMPLE R7

Ethane-1,2-diylbis(oxyethane-2,1-diyloxy-3,1-phenylenemethylene)dimethanesulphonate 0.46 ml (3.31 mmol) of triethylamine and 0.18 ml (2.26 mmol) of mesyl chloride are added to the solution of 0.40 g (1.10 mmol) of [ethane-1,2-diylbis(oxyethane-2,1-diyloxy-3,1-phenylene)]dimethanol (CAS 197573-04-9; J. E. Kickham, S. J. Loeb, S. L. Murphy, *Chemistry—A European Journal*, 1997, 3(8), 1203-1213) in 8 ml of dichloromethane at −20° C. under nitrogen. The solution is stirred at −20° C. for 3 hours and is then run into hydrochloric acid (1 M) and the mixture is extracted with dichloromethane. The organic phase is washed with a saturated aqueous solution of sodium chloride, dried over sodium sulphate and concentrated under reduced pressure. 0.50 g (88%) of a colourless oil is obtained.

MNH4+=536.3.

EXAMPLE R8

1,1'-[Ethane-1,2-diylbis(oxyethane-2,1-diyloxy)]bis[4-(bromomethyl)benzene]

CAS 110911-60-9; B. Cabezon, J. F. Cao, M. Raymo, J. F. Stoddart, A. J. P. White and D. J. Williams, *Chemistry—A European Journal*, 2000, 6(12), 2262-2273.

EXAMPLE R9

1,1'-[octane-1,8-diyloxy)]bis[4-(bromo-methyl)benzene]

CAS 263715-25-9; C. A. Schalley, G. Silva; Nising, F. Carl; P. Linnartz, *Helvetica Chimica Acta*, 2002, 85(6), 1578-1596.

EXAMPLE R10 piperazine-1,4-diyldiethane-2,1-diyl dimethanesulphonate

CAS 48185-66-6; described in Sv. Zikolova, R. Konstantinova, L. Zhelyazkov, G. Sheikova, *Turdove na Nauchnoizsledovatelskiya Khimikofarmatsevtichen Institut*, 1972, 7, 117-22.

EXAMPLE R11

1,3-bis(2-Iodoethyl)-5-methoxybenzene

Stage A: Diethyl 2,2'-[(5-methoxy-1,3-phenylene)-bis(oxy)]diacetate 5.0 g (35.7 mmol) of 5-methoxybenzene-1,3-diol and then, after 10 minutes, 8.7 ml (78.5 mmol) of ethyl 2-bromoacetate are added to the suspension of 3.1 g (71.4 mmol) of sodium hydride (60% dispersion in oil) in 180 ml of 1-methyl-2-pyrrolidinone under argon. The mixture is stirred at ambient temperature for 3 hours. The reaction medium is diluted with ethyl acetate and washed with a saturated aqueous solution of potassium hydrogen sulphate and a saturated solution of sodium chloride and dried over sodium sulphate then concentrated to dryness. The crude product is purified by chromatography on silica gel (dichloromethane/ethyl acetate=95/5). 5.9 g (53%) of a colourless gum are obtained.
MH$^+$=313.1.

Stage B: 2,2'-[(5-Methoxy-1,3-phenylene)bis(oxy)]-diethanol 10 ml of lithium aluminium hydride (1 M in tetrahydrofuran) are introduced into a three-necked flask under argon. After having cooled the solution to 0° C., 1.0 g (3.2 mmol) of diethyl 2,2'-[(5-methoxy-1,3-phenylene)bis(oxy)]diacetate in solution in 6 ml of tetrahydrofuran is added. The formation of a white precipitate is observed. After stirring for one hour at ambient temperature, ethyl acetate is slowly added at 0° C. The mixture is poured into a saturated aqueous solution of potassium hydrogen sulphate and the mixture is extracted with ethyl acetate. The organic phase is washed with a saturated solution of sodium chloride and dried over sodium sulphate, then concentrated to dryness. 1.0 g (78%) of a white powder is obtained.
MH$^+$=229.5.

Stage C 1.28 g (4.88 mmol) of triphenylphosphine and 0.35 g (5.14 mmol) of imidazole are added to the solution of 0.43 g (1.88 mmol) of the diol obtained in the preceding stage in 3 ml of acetonitrile, 4.5 ml of ethyl ether and 2 ml of tetrahydrofuran. After having cooled the solution to 0° C., 1.36 g (5.36 mmol) of iodine are added portionwise. The solution is stirred at 0° C. for 2 hours and then at ambient temperature for 16 hours. It is poured into a solution of sodium bisulphite (10%) and extracted with ethyl acetate. The organic phase is washed with a saturated solution of sodium chloride, dried over sodium sulphate and concentrated to dryness. The crude product is purified by chromatography on silica gel (dichloromethane/ethyl acetate gradient=100/0 to 60/60). 0.75 g (89%) of a white powder is obtained.
MH$^+$=449.0.

EXAMPLE R12

3,3'-[Octane-1,8-diylbis(oxy)]dibenzoic acid

CAS 112763-29-8; D. Ramprasad, W. K. Lin, K. A. Goldsby, D. H. Busch, *J. Am. Chem. Soc.*, 1988, 110(5), 1480-1487.

EXAMPLE R13

3,3'-{Ethane-1,2-diylbis[imino(2-oxoethane-2,1-diyl)oxy]}dibenzoic acid

Stage A: Ethyl 3-(2-chloro-2-oxoethoxy)benzoate 32.5 ml (0.45 mol) of thionyl chloride and 10 μl of N,N-dimethylformamide are added to a solution of 20.0 g (89.2 mmol) of [3-(ethoxycarbonyl)phenoxy]acetic acid (A. Banerjee, M. M. Adak, S. Das, S. Banerjee, S. Sengupta, *Indian Chem. Soc.*, 1987, 64, 1, 34-37) in 200 ml of 1,2-dichloroethane. The mixture is refluxed for 1 hour and is then concentrated to dryness and dried under vacuum at 50° C. overnight and used as it is in the subsequent stage.

Stage B 2.95 ml (44.1 mmol) of ethane-1,2-diamine in solution in 10 ml of dichloromethane and 12.3 ml (88.2 mmol) of triethylamine are added, dropwise, at ambient temperature, to the solution of 21.4 g (88.2 mmol) of the acid chloride obtained in the preceding stage in 170 ml of dichloromethane. The reaction is exothermic (it is cooled using an ice bath) and the formation of a white precipitate is observed. Once the addition is complete, the reaction medium is stirred at ambient temperature for 1 hour. After dilution with dichloromethane, the organic phase is washed with a saturated aqueous solution of potassium hydrogen sulphate and a saturated solution of sodium bicarbonate and is dried over sodium sulphate before being concentrated to dryness. The solid obtained is taken up in heptane, filtered and dried, to give 19.2 g (92%) of a white powder.
MH$^+$=473.3.

Stage C 100 ml of sodium hydroxide (1 M) are added to the suspension of 19.5 g (40.3 mmol) of the ethyl diester in 65 ml of 1,4-dioxane and 65 ml of ethanol, and then the mixture is heated at 100° C. for 1 hour. The clear solution is run into 150 ml of hydrochloric acid (1 M). The precipitate obtained is filtered, thoroughly washed with water and then dried under vacuum at 50° C., to give 14.4 g (85%) of a white powder.
MH$^+$=417.3; melting point: 282° C.

EXAMPLE R14

4,4'-{Ethane-1,2-diylbis[imino(2-oxoethane-2,1-diyl)oxy]}dibenzoic acid

Stage A 4.9 ml (35.4 mmol) of triethylamine and 7.8 g (17.7 mmol) of BOP® are added, under argon at 0° C., to 4.6 g (16.1 mmol) of {4-[(benzyloxy)carbonyl]phenoxy}acetic acid (described in Patent Application WO2001060813) in solution in 50 ml of dichloromethane. After 30 minutes, 0.54 ml (8.03 mmol) of ethane-1,2-diamine is added. The reaction medium is stirred at ambient temperature for 16 hours. The reaction medium is diluted with ethyl acetate and extracted with a saturated aqueous solution of sodium bicarbonate. A precipitate forms, it is filtered, washed with water and then dried. 3.0 g of a white powder are obtained, which powder is used without purification in the subsequent saponification stage.

Stage D 12.6 ml of sodium hydroxide (1 M) are added to the solution of 3.0 g (5.03 mmol) of the ethyl diester obtained in stage C above in 40 ml of 1-methyl-2-pyrrolidinone. The solution is stirred at ambient temperature for 16 hours. The reaction medium is acidified by adding hydrochloric acid (1 M). The precipitate is filtered and washed with water. After drying under vacuum, 1.3 g of a white powder are obtained.

$MH^+$=417.5; melting point: 270° C.

EXAMPLE R15

Sodium salt of 3,3'-{[2-(dimethylamino)-propane-1,3-diyl]bis[imino(2-oxoethane-2,1-diyl)oxy]}dibenzoic acid By following the processes described in stages A to C of Example R13, Example R15 is prepared by dimerization of [3-(ethoxycarbonyl)phenoxy]acetic acid with $N^2,N^2$-dimethylpropane-1,2,3-triamine. For step C, when the saponification of the diester is complete, the reaction medium is concentrated to dryness taken up in toluene and concentrated to dryness, and then dissolved in methanol and concentrated to dryness to give a yellow gum. The product is dissolved in methanol and precipitated from diisopropyl ether. The precipitate is filtered and dried under vacuum at 50° C., to give a white powder.

$MH^+$=474.4; melting point: 280° C.

EXAMPLE R16

Sodium salt of 3,3'-({2-[(dimethylamino)-methyl]propane-1,3-diyl}bis[imino(2-oxoethane-2,1-diyl)oxy])dibenzoic acid By following the processes described in Example R15, Example R16 is prepared by dimerization of [3-(ethoxycarbonyl)phenoxy]acetic acid with 2-(aminomethyl)-N,N-dimethylpropane-1,3-diamine. A white powder is obtained.

$MH^+$=488.4; melting point: 289° C.

EXAMPLE R17

3,3'-{(2-hydroxypropane-1,3-diyl)-bis[imino(2-oxoethane-2,1-diyl)oxy]}dibenzoic acid By following the processes described in stages A to C of Example R13, Example R15 is prepared by dimerization of [3-(ethoxycarbonyl)phenoxy]acetic acid with 1,3-diaminopropan-2-ol. A white powder is obtained.

$MH^+$=447.4; melting point: 201° C.

EXAMPLE R18

Sodium salt of 3,3'-{ethane-1,2-diyl-bis[(methylimino)ethane-2,1-diyloxy]}dibenzoic acid

Stage A

The mixture of 4.0 g (12.5 mmol) of ethyl 3-(2-iodoethoxy)benzoate (see preparation of the methyl ester analogue CAS 225122-62-3: P. D. Greenspan et al., *J. Med. Chem.*, 2001, 44, 4524-4534), 0.78 ml (6.2 mmol) of N,N-dimethylethane-1,2-diamine and 1.73 g (12.3 mmol) of potassium carbonate in 23 ml of N,N-dimethylformamide is heated at 60° C. for 3 hours. The mixture is cooled to ambient temperature, diluted with ethyl acetate and extracted with water. The organic phase is washed with a saturated solution of sodium chloride, dried over sodium sulphate and concentrated to dryness, to give a yellow oil.

$MH^+$=473.2.

Stage B 6.5 ml of sodium hydroxide (1 M) are added to the suspension of 1.53 g (3.24 mmol) of the ethyl diester obtained in stage A above in 20 ml of ethanol. The solution is stirred at ambient temperature for 17 hours. The reaction medium is concentrated to dryness, then taken up in ethanol and concentrated to dryness, to give a white powder, three times. The product is suspended in acetone and filtered and then dried under vacuum at 50° C. to give a white powder.

$MH^+$=417.2; melting point=210° C.

EXAMPLE R19

Sodium salt of 3,3'-{ethane-1,2-diyl-bis[(benzylimino)ethane-2,1-diyloxy]}dibenzoic acid By following the processes described in stages A and B of Example R18, Example R19 is prepared by dimerization of ethyl 3-(2-iodoethoxy)benzoate with N,N-di-benzylethane-1,2-diamine. A white powder is obtained.

$MH^+$=569.3.

EXAMPLE R20

Disodium salt of 4,4'-{ethane-1,2-diyl-bis[(methylimino)ethane-2,1-diyloxy]}dibenzoic acid By following the processes described in stages A and B of Example R18, Example R20 is prepared by dimerization of ethyl 4-(2-iodoethoxy)benzoate [CAS 56703-36-7 described in M. Kanao et al., *Chem. Pharm. Bull.*, 1988, 36(8), 2968-76] with N,N-dimethylethane-1,2-diamine. A white powder is obtained.

$MH^+$=417.1.

EXAMPLE R21

3,3'-[(3,4-dioxocyclobut-1-ene-1,2-diyl)-bis(iminoethane-2,1-diyloxy)]dibenzoic acid

Stage A

Under a nitrogen atmosphere and at ambient temperature, 0.39 g of 3,4-diethoxy-3-cyclobutene-1,2-dione (2.27 mmol)

is added to a solution of 1.04 g of ethyl 3-(2-aminoethoxy) benzoate (4.98 mmol) [see preparation of the methyl ester analogue CAS 153938-41-1 described in C. C. Appeldoorn et al., *Tetrahedron Asymm.*, 2005, 16(2), 361-372] in 23 ml of dichloromethane. The reaction medium thickens after 24 h of reaction. After stirring for 6 days, the reaction medium is filtered. The solid obtained is taken up in diisopropyl ether, filtered and dried under vacuum. After drying, 1.98 g (87%) of ethyl diester is obtained in the form of a white powder.

$MH^+$=497.2; melting point=144.8° C.

Stage B 4.2 ml of sodium hydroxide (1 M) are added to the solution of diester obtained in the preceding stage in 3.8 ml of dimethyl sulphoxide. The solution is stirred at ambient temperature for 24 hours. The reaction medium is poured into an aqueous solution of potassium hydrogen sulphate (2.2 eq.). The dicarboxylic acid precipitates, it is filtered, washed with water to neutral pH and dried under vacuum to give the dicarboxylic acid in the form of a white powder.

$MH^+$=441.3; melting point=281.5° C.

EXAMPLE R22

Sodium salt of 3,3'-[(1,2-dioxoethane-1,2-diyl)bis (iminoethane-2,1-diyloxy)]dibenzoic acid Stage A 2.82 g (8.70 mmol) of 1-benzotriazolyl oxalate are added to a solution of 2.02 g (9.67 mmol) of ethyl 3-(2-aminoethoxy)benzoate [see preparation of the methyl ester analogue CAS 153938-41-1 described in C. C. Appeldoorn et al., *Tetrahedron Asymm.*, 2005, 16(2), 361-372] in 97 ml of N,N-dimethylformamide. The mixture is stirred at ambient temperature for 6 days. The reaction medium is poured into a saturated aqueous solution of sodium hydrogen carbonate and then extracted with an ethyl acetate/tetrahydrofuran (1/1) mixture. The organic phase is washed with water to neutral pH and then with a saturated aqueous solution of sodium chloride, dried with anhydrous sodium sulphate and concentrated to dryness. The solid obtained is taken up in diisopropyl ether, filtered and dried under vacuum to give 1.59 g (70%) of diester in the form of a white powder.

$MH^+$=497.2.

Stage B 5 ml of sodium hydroxide (1 M) are added to the solution of 1.1 g (2.31 mmol) of the diester in 35 ml of N-methylpyrrolidinone. After stirring for 21 hours, the reaction medium is poured into 350 ml of acetone. The sodium salt precipitates, it is filtered, washed with acetone and dried under vacuum to give the dicarboxylic acid in the form of a white powder.

$MH^+$=417.1.

EXAMPLE R23

4,4'-{Ethane-1,2-diylbis[(methylimino)(2-oxoethane-2,1-diyl)oxy]}dibenzoic acid

By following the processes described in stages A and B of Example R14, Example R23 is prepared by dimerization of {4-[(benzyloxy)carbonyl]phenoxy}acetic acid (described in Patent Application WO2001060813) with N,N-dimethylethane-1,2-diamine. A white powder is obtained.

$MH^+$=445.2; melting point: 178° C.

EXAMPLE R24

4,4'-[Oxybis(ethane-2,1-diyloxyethane-2,1-diyloxy)] dibenzoic acid

CAS 111630-85-4; K. N. Wiegel, A. C. Griffin, M. S. Black, D. A. Schiraldi, *Journal of Applied Polymer Science*, 2004, 92(5), 3097-3106.

EXAMPLE R25

4,4'-[Ethane-1,2-diylbis(oxyethane-2,1-diyloxy)] dibenzoic acid

CAS 101678-92-6; B. M. Vogel, S. K. Mallapragada, *Biomaterials*, 2004, Volume Date 2005, 26(7), 721-728.

EXAMPLE R26

4,4'-[Oxybis(ethane-2,1-diyloxy)]benzoic acid

CAS 69984-27-6; D. H. Hua, M. Tamura, M. Masahiro, K. Werbovetz, D. Delfin, M. Salem and P. K. Chiang, *Bioorg. Med. Chem.*, 2003, 11, 20, 4357-4362.

EXAMPLE R27

4,4'-[Ethane-1,2-diylbis(oxy)]dibenzoic acid

CAS 3753-05-7; R. van Helden and A. F. Bickel, *Recl. Trav. Chim. Pays-Bas*, 1961, 80, 1237-1253.

EXAMPLE R28

4,4'-[Propane-1,3-diylbis(oxy)dibenzoic acid

CAS 3753-81-9; F. H. McMillan, *J. Am. Chem. Soc*, 1952, 74, 5229-5230.

EXAMPLE R29

4,4'-[Ethane-1,3-diylbis(oxy)]dibenzoic acid

CAS 3753-05-7; G. Avitabile et al., *J. of Polymer Science, Part B: Polymer Physics*, 1999, 37(14), 1687-1701.

EXAMPLE R30

3,3'-[1,3-phenylenebis(sulphonylimino-ethane-2,1-diyloxy)]dibenzoic acid

Stage A 0.77 ml (5.5 mmol) of triethylamine and 0.61 g (2.2 mmol) of 1,3-benzenedisulphonyl chloride are added to a solution of 1.01 g (4.84 mmol) of ethyl 3-(2-aminoethoxy)benzoate [see preparation of the methyl ester analogue CAS 153938-41-1 described in C. C. Appeldoorn et al., *Tetrahedron Asymm.*, 2005, 16(2), 361-372] in 22 ml of dichloromethane. After stirring at ambient temperature for 5 days, the reaction medium is poured into an aqueous solution of hydrochloric acid (0.1 N) and then extracted with ethyl acetate, and the organic phase is washed with a saturated aqueous solution of sodium hydrogen carbonate, then with water and with a saturated aqueous solution of sodium chloride, dried with anhydrous sodium sulphate and concentrated to dryness. The solid obtained is taken up in diisopropyl ether, filtered and dried under vacuum to give 1.23 g (90%) of diester in the form of a white powder.

$MH^+$=621.2; melting point: 124.7° C.

Stage B

By following the process described in stage B of Example R21, the dicarboxylic acid is obtained in the form of a white powder.

$MH^+$=565.2; melting point: 226.2° C.

EXAMPLE R31

3,3'-[(1,3-Dioxopropane-1,3-diyl)-bis(iminoethane-2,1-diyloxy)]dibenzoic acid

Stage A

Under a nitrogen atmosphere and at ambient temperature, EDCI (1.02 g/5.34 mmol), 1-hydroxybenzotriazole (0.72 g/5.34 mmol), triethylamine (0.75 ml/5.34 mmol) and malonic acid (0.25 g/2.43 mmol) are added respectively to a solution of ethyl 3-(2-aminoethoxy)benzoate see preparation of the methyl ester analogue CAS 153938-41-1 described in C. C. Appeldoorn et al., *Tetrahedron Asymm.*, 2005, 16(2), 361-372] (1.02 g/4.86 mmol) in 24 ml of N,N-dimethylformamide. After stirring for 24 hours, the reaction medium is poured into a saturated aqueous solution of potassium hydrogen sulphate and is then extracted with ethyl acetate. The organic phase is washed with water to neutral pH and then with a saturated aqueous solution of sodium chloride, dried with anhydrous sodium sulphate and concentrated to dryness. The oil obtained is taken up in diisopropyl ether, a white precipitate is obtained, it is filtered and dried under vacuum to give 0.76 g (64%) of diester in the form of a white powder.

$MH^+$=487.3; melting point: 98.9° C.

Stage B

By following the process described in stage B of Example R21, the dicarboxylic acid is obtained in the form of a white powder.

$MH^+$=431.2; melting point: 240.8° C.

EXAMPLE R32

3,3'-[1,4-Phenylenebis(carbonylimino-ethane-2,1-diyloxy)]dibenzoic acid

Stage A

By following the process described in stage C of Example 53, the coupling of ethyl 3-(2-aminoethoxy)benzoate [see preparation of the methyl ester analogue CAS 153938-41-1 described in C. C. Appeldoorn et al., *Tetrahedron Asymm.*, 2005, 16(2), 361-372] with terephthalic acid is carried out.

$MH^+$=549.3; melting point: 153.5° C.

Stage B

By following the process described in stage B of Example R21, the saponification of the diester is carried out so as to obtain the dicarboxylic acid in the form of a white powder.

$MH^+$=493.2; melting point: 284.5° C.

EXAMPLE R33

3,3'-[pyridine-3,5-diylbis(carbonylimino-ethane-2,1-diyloxy)]dibenzoic acid

Stage A

By following the process described in stage C of Example 53, the coupling of ethyl 3-(2-aminoethoxy)benzoate [see preparation of the methyl ester analogue CAS 153938-41-1 described in C. C. Appeldoorn et al., *Tetrahedron Asymm.*, 2005, 16(2), 361-372] with 3,5-pyridinecarboxylic acid is carried out.

$MH^+$=550.3; melting point: 121° C.

Stage B

By following the process described in stage B of Example R21, the saponification of the diester is carried out so as to obtain the dicarboxylic acid in the form of a white powder.

$MH^+$=494.1; melting point: 246.5° C.

EXAMPLE R34

3,3'-{Ethane-1,2-diylbis[(methylimino)-(2-oxoethane-2,1-diyl)oxy]}dibenzoic acid By following the processes described in stages A to C of Example R13, Example R34 is prepared by dimerization of [3-(ethoxycarbonyl)phenoxy]acetic acid with N,N-dimethyl-ethane-1,2-diamine. A white powder is obtained.

$MH^+$=445.2; melting point: 179° C.

EXAMPLE R35

3,3'-{(1R,2R)-cyclopropane-1,2-diyl-bis[imino(2-oxoethane-2,1-diyl)oxy]}dibenzoic acid By following the processes described in stages A to C of Example R13, Example R35 is prepared by dimerization of [3-(ethoxycarbonyl)phenoxy]acetic acid with 1,2-trans-cyclopropanediamine (CAS 758637-65-9). A white powder is obtained.

$MH^+$=429.3; melting point: 121° C.

EXAMPLE R36

3,3'-{(1R,2S)-cyclopropane-1,2-diyl-bis[imino(2-oxoethane-2,1-diyl)oxy]}dibenzoic acid By following the processes described in stages A to C of Example R13, Example R36 is prepared by dimerization of [3-(ethoxycarbonyl)phenoxy]acetic acid with 1,2-cis-cyclopropanediamine (CAS 365996-16-3). A white powder is obtained.

$MH^+$=429.3; melting point: 253° C.

EXAMPLE R37

3,3'-{methylenebis[imino(2-oxoethane-2,1-diyl)oxy]}dibenzoic acid

By following the processes described in stages A to C of Example R13, Example R37 is prepared by dimerization of [3-(ethoxycarbonyl)phenoxy]acetic acid with methylenediamine. A white powder is obtained.

$MH^+$=401.4; melting point: 252° C.

EXAMPLE R38

N,N'-ethylenebis(N-methylsuccinamic acid)

CAS 62538-62-9; described in R. E. Asay et al., *J. Heterocyclic Chem.*, 1977, 14(1), 85-90.

EXAMPLES R39 TO R64

By following the procedure described for the preparation of Example R38, the dicarboxylic acids R39 to R61 are prepared with the diamines and the anhydrides given in the table below.

| | Dicarboxylic acids | Diamines | Anhydrides | MH+/RT (Method D) |
|---|---|---|---|---|
| R39 | HO₂C—CH₂CH₂CON(CH₃)CH₂CH₂—(OCH₂CH₂)₂N(CH₃)COCH₂CH₂CO₂H | (CH₃)HNCH₂CH₂(OCH₂CH₂)₂NH(CH₃) | succinic anhydride | MH+ = 377.2 RT = 0.674 min |
| R40 | HO₂C—CH₂CH₂CON(CH₃)CH₂CH₂—OCH₂CH₂N(CH₃)COCH₂CH₂CO₂H | (CH₃)HNCH₂CH₂OCH₂CH₂NH(CH₃) | succinic anhydride | MH+ = 333.0 RT = 0.635 min |
| R41 | HO₂C—(CH₂)₂OC-N(homopiperazine)N-CO(CH₂)₂CO₂H | homopiperazine (NH-NH ring) | succinic anhydride | MH+ = 301.0 RT = 0.251 min |
| R42 | HO₂C—CH₂CH₂CON(CH₃)(CH₂)₈—N(CH₃)COCH₂CH₂CO₂H | (CH₃)HN(CH₂)₈NH(CH₃) | succinic anhydride | MH+ = 373.2 RT = 0.989 min |
| R43 | HO₂C—CH₂CH₂CON(CH₃)CH₂CH₂—CH₂N(CH₃)COCH₂CH₂CO₂H | (CH₃)HNCH₂CH₂OCH₂CH₂NH(CH₃) | succinic anhydride | MH+ = 303.2 RT = 0.561 min |
| R44 | HO₂C—(CH₂)₃CON(CH₃)CH₂CH₂—(OCH₂CH₂)₂N(CH₃)CO(CH₂)₃CO₂H | (CH₃)HNCH₂CH₂(OCH₂CH₂)₂NH(CH₃) | glutaric anhydride | MH+ = 405.2 RT = 0.740 min |
| R45 | HO₂C—(CH₂)₃CON(CH₃)(CH₂)₈N(CH₃)CO(CH₂)₃CO₂H | (CH₃)HN(CH₂)₈NH(CH₃) | glutaric anhydride | MH+ = 401.2 RT = 1.028 min |
| R46 | HO₂C—(CH₂)₃CON(CH₃)(CH₂)₆N(CH₃)CO(CH₂)₃CO₂H | (CH₃)HN(CH₂)₆NH(CH₃) | glutaric anhydride | MH+ = 373.0 RT = 0.885 min |
| R47 | HO₂C—(CH₂)₃CON(CH₃)CH₂CH₂—OCH₂CH₂N(CH₃)CO(CH₂)₃CO₂H | (CH₃)HNCH₂CH₂OCH₂CH₂NH(CH₃) | glutaric anhydride | MH+ = 361.1 RT = 0.734 min |

-continued

| | Dicarboxylic acids | Diamines | Anhydrides | MH+/RT (Method D) |
|---|---|---|---|---|
| R48 | HO$_2$C—(CH$_2$)$_3$CON(CH$_3$)(CH$_2$)$_2$N(CH$_3$)CO(CH$_2$)$_3$CO$_2$H | (CH$_3$)HN(CH$_2$)$_2$NH(CH$_3$) | ![glutaric anhydride] | MH$^+$ = 317.2 RT = 0.599 min |
| R49 | HO$_2$C—(CH$_2$)$_3$CO—N(azepane)—CO(CH$_2$)$_3$CO$_2$H | azepane (HN) | ![glutaric anhydride] | MH$^+$ = 329.0 RT = 0.623 min |
| R50 | HO$_2$C—CH$_2$OCH$_2$CON(CH$_3$)CH$_2$CH$_2$—(OCH$_2$CH$_2$)$_2$N(CH$_3$)COCH$_2$OCH$_2$CO$_2$H | (CH$_3$)HNCH$_2$CH$_2$(OCH$_2$CH$_2$)$_2$NH(CH$_3$) | ![diglycolic anhydride] | MH$^+$ = 409.2 RT = 0.616 min |
| R51 | HO$_2$C—CH$_2$OCH$_2$CON(CH$_3$)(CH$_2$)$_8$—N(CH$_3$)COCH$_2$OCH$_2$CO$_2$H | (CH$_3$)HN(CH$_2$)$_8$NH(CH$_3$) | ![diglycolic anhydride] | 405.2 RT = 0.953 min |
| R52 | HO$_2$C—CH$_2$OCH$_2$CON(CH$_3$)(CH$_2$)$_6$—N(CH$_3$)COCH$_2$OCH$_2$CO$_2$H | (CH$_3$)HN(CH$_2$)$_6$NH(CH$_3$) | ![diglycolic anhydride] | 377.2 RT = 0.786 min |
| R53 | HO$_2$C—CH$_2$OCH$_2$CON(CH$_3$)(CH$_2$)$_3$—N(CH$_3$)COCH$_2$OCH$_2$CO$_2$H | (CH$_3$)HN(CH$_2$)$_3$NH(CH$_3$) | ![diglycolic anhydride] | 355.2 RT = 0.413 min |
| R54 | HO$_2$C—N(piperazine)—CO(CH$_2$)$_3$CO$_2$H | piperazine (HN/NH) | ![glutaric anhydride] | RT = 0.591 min (315.2) |
| R55 | HO$_2$C—CH$_2$OCH$_2$CO—N(piperazine)—COCH$_2$OCH$_2$CO$_2$H | piperazine (HN/NH) | ![diglycolic anhydride] | 319.2 RT = 0.181 min |

-continued

| | Dicarboxylic acids | Diamines | Anhydrides | MH+/RT (Method D) |
|---|---|---|---|---|
| R56 | HO$_2$C—(CH$_2$)$_4$CON(CH$_3$)(CH$_2$)$_3$N(CH$_3$)CO(CH$_2$)$_4$CO$_2$H | (CH$_3$)HN(CH$_2$)$_3$NH(CH$_3$) | 7-membered cyclic anhydride | 359.2 RT = 0.770 min |
| R57 | HO$_2$C—(CH$_2$)$_2$CON(CH$_3$)(CH$_2$)$_6$N(CH$_3$)CO(CH$_2$)$_2$CO$_2$H | (CH$_3$)HN(CH$_2$)$_6$NH(CH$_3$) | succinic anhydride | 345.2 RT = 0.831 min |
| R58 | HO$_2$C—CH$_2$OCH$_2$CON(CH$_3$)CH$_2$CH$_2$OCH$_2$CH$_2$N(CH$_3$)COCH$_2$OCH$_2$CO$_2$H | (CH$_3$)HNCH$_2$CH$_2$OCH$_2$CH$_2$NH(CH$_3$) | diglycolic anhydride | 365.0 RT = 0.507 min |
| R59 | HO$_2$C—(CH$_2$)$_4$CON(CH$_3$)(CH$_2$)$_2$N(CH$_3$)CO(CH$_2$)$_4$CO$_2$H | (CH$_3$)HN(CH$_2$)$_2$NH(CH$_3$) | 7-membered cyclic anhydride | 345.2 RT = 0.717 min |
| R60 | HO$_2$C—(CH$_2$)$_3$CON(CH$_3$)(CH$_2$)$_3$N(CH$_3$)CO(CH$_2$)$_3$CO$_2$H | (CH$_3$)HN(CH$_2$)$_3$NH(CH$_3$) | glutaric anhydride | 331.2 RT = 0.671 min |
| R61 | HO$_2$C—CH$_2$OCH$_2$CON(CH$_3$)CH$_2$—CH$_2$N(CH$_3$)COCH$_2$OCH$_2$CO$_2$H | (CH$_3$)HNCH$_2$CH$_2$NH(CH$_3$) | diglycolic anhydride | 321.2 RT = 0.210 min |

EXAMPLE R65

2,2'-[Ethane-1,2-diylbis(oxyethane-2,1-diyloxy-4,1-phenylene)]bis(4,4,5,5-tetramethyl-1,3,2-dioxaborolane)

The mixture of 3.0 g (13.6 mmol) of 4-(4,4,5,5-tetramethyl-1,3,2-dioxaborolan-2-yl)phenol, 2.51 g (6.82 mmol) of 1-iodo-2-[2-(2-iodoethoxy)ethoxy]ethane (Example R5) and 8.9 g (27.3 mmol) of caesium carbonate in 30 ml of N,N-dimethylformamide is heated at 60° C. for 5 hours. The solution is run into a saturated aqueous solution of potassium hydrogen sulphate and extracted with ethyl acetate. The organic phase is washed with a saturated solution of sodium chloride, dried over sodium sulphate and concentrated to dryness. The solid obtained is purified by flash chromatography on silica gel (cyclohexane/diisopropyl ether gradient=90/10 to 0/100), to give 1.8 g (47%) of a white powder.
MH+=555.5; melting point: 97° C.

EXAMPLE R66

2,2'-[Oxybis(ethane-2,1-diyloxyethane-2,1-diyloxy-4,1-phenylene)]bis(4,4,5,5-tetramethyl-1,3,2-dioxaborolane)

By following the process described in Example R65, Example R66 is prepared by dimerization of 4-(4,4,5,5-tetramethyl-1,3,2-dioxaborolan-2-yl)phenol with 1-iodo-2-{2-[2-(2-iodoethoxy)ethoxy]ethoxy}ethane (Example R4). A white powder is obtained.
MH+=599.4; melting point: 55° C.

EXAMPLE R67

2,2'-[Ethane-1,2-diylbis(oxyethane-2,1-diyloxy-3,1-phenylene)]bis(4,4,5,5-tetramethyl-1,3,2-dioxaborolane)

By following the process described in Example R65, Example R67 is prepared by dimerization of 3-(4,4,5,5-tetramethyl-1,3,2-dioxaborolan-2-yl)phenol with 1-iodo-2-[2-(2-iodoethoxy)ethoxy]ethane (Example R5). A white powder is obtained.
MNH4+=572.4.

EXAMPLE R68

[Oxybis(ethane-2,1-diyloxyethane-2,1-diyloxy-3,1-phenylene)]diboronic acid

The mixture of 3.0 g (13.6 mmol) of 3-(4,4,5,5-tetramethyl-1,3,2-dioxaborolan-2-yl)phenol, 2.82 g (6.82 mmol) of 1-iodo-2-{2-[2-(2-iodoethoxy)ethoxy]-ethoxy}ethane (Example R4) and 8.88 g (27.3 mmol) of caesium carbonate in 30 ml of N,N-dimethylformamide is heated at 60° C. for 5 hours. The solution is run into a saturated aqueous solution of potassium hydrogen sulphate and extracted with ethyl acetate. The organic phase is washed with a saturated solution of sodium chloride, dried over sodium sulphate and concentrated to dryness. The target boronic diester, partly hydrolysed to boronic acid, is obtained.

The reaction crude is solubilized in a mixture of 20 ml of 1,2-dimethoxyethane and 80 ml of water in the presence of 3.18 g (30.1 mmol) of sodium carbonate. After stirring at ambient temperature for 3 days, the aqueous solution is washed with ethyl acetate and then acidified with a saturated aqueous solution of potassium hydrogen sulphate and extracted with ethyl acetate. The organic phase is washed with water and with a saturated solution of sodium chloride, dried over sodium sulphate and then concentrated to dryness. 0.82 g (28%) of a white powder are obtained.
MH+=435.3.

EXAMPLE R69

3-{2-[(2-{[(4-Carboxyphenoxy)acetyl]-amino}ethyl)amino]-2-oxoethoxy}benzoic acid Stage A: Ethyl 3-{2-[(2-aminoethyl)amino]-2-oxoethoxy}benzoate 1.94 ml (14 mmol) of triethylamine, 5.73 g (11 mmol) of PyBOP and 1.45 ml (9.2 mmol) of N-tert-butyloxy-carbonylethylenediamine are added to 2.06 g (9.2 mmol) of {4-[(benzyloxy)carbonyl]phenoxy}acetic acid (described in patent application WO2001060813) in 46 ml of dichloromethane under a nitrogen atmosphere and at ambient temperature. After stirring for 22 hours, the reaction medium is run into an aqueous solution of hydrochloric acid (0.1 N) and is then extracted with ethyl acetate. The organic phase is washed with a saturated aqueous solution of sodium hydrogen carbonate and then with a saturated aqueous solution of sodium chloride, dried over anhydrous sodium sulphate and concentrated to dryness. The oil obtained is taken up in diisopropylether, the white precipitate obtained is filtered and dried under vacuum, to give 1.95 g (58%) of the carbamate in the form of a white powder.

5.64 ml (76 mmol) of trifluoroacetic acid are added, at ambient temperature, to a solution of 1.39 g (3.80 mmol) of the carbamate in 24 ml of dichloromethane. After stirring for 4 h 30, 100 ml of 1,2-dichloroethane are added to the reaction medium, which is then concentrated to dryness. The oil obtained is poured into a saturated aqueous solution of sodium hydrogen carbonate and extracted with a tetrahydrofuran/ethyl acetate (1/1) mixture. The organic phase is concentrated to dryness, and the oil obtained is dried under vacuum to give 1.09 g (86%) of the amine in the form of a yellow oil.
MH+=267.3.

Stage B: Ethyl 3-{2-[(2-{[(4-carboxyphenoxy)acetyl]amino}ethyl)amino]-2-oxoethoxy}benzoate Under a nitrogen atmosphere and at ambient temperature, 0.86 ml (6.12 mmol) of triethylamine, 2.55 g (4.89 mmol) of PyBOP and 1.09 g (4.08 mmol) of ethyl 3-{2-[(2-aminoethyl)amino]-2-oxoethoxy}benzoate are added respectively to a solution of 0.91 g (4.08 mmol) of {4-[(ethyloxy)carbonyl]phenoxy}acetic acid (CAS 30893-58-4) in 20 ml of dichloromethane. The reaction medium is heterogeneous. After stirring for 5 hours, the reaction medium is filtered. The filtrate obtained is concentrated to dryness. The residue obtained is poured into a saturated aqueous solution of sodium hydrogen carbonate. The solid obtained is filtered, washed with water and dried under vacuum, to give 1.22 g (63%) of the diester in the form of a white powder.
MH+=473.2; melting point: 117.5° C.

Stage C

By following the process described in stage B of Example R21, the saponification of the diester is carried out so as to obtain the dicarboxylic acid in the form of a white powder.

MH⁺=417.2; melting point: 257.1° C.

The results of in vitro and in vivo pharmacological tests carried out with a view to determining properties of the compounds of the invention are listed below:

Baf/3-FGFR1β or FGF-R4α Proliferation Model

Obtaining the Chimeric Receptor Constructs

The chimeric receptors are made up of the intracellular portion of hMp1 (NM_005373) and the transmembrane and extracellular domains of FGF-R1β or FGF-R4α.

For each FGF receptor, the FGF-R (BamHI-SacI) and hMp1 (SacI-NotI) fragments are simultaneously cloned into the vector pEF6 (Invitrogen) digested with BamHI and NotI.

BaF/3 Transfection

Murine BaF/3 cells are transfected by electroporation. 20 μg of plasmid carrying the constructs FGF-R1β-hMp1 or FGF-R4α-hMp1 are mixed with 5×10⁶ cells taken up in 800 μl of RPMI (invitrogen). The mixture is subjected to two electric shocks of 400 V with an interval of 0.1 ms. The cells are taken up for 48 h in an RPMI medium containing 10% FCS (foetal calf serum, gibco), glutamine (invitrogen), NEAA (nonessential amino acids, invitrogen), NaPyr (sodium pyruvate, invitrogen) and 10 ng/ml of IL-3, before being selected with 10 μg/ml of blasticidin (Cayla).

Culture of Transfected Cells

The BaF/3 cell lines transfected with the FGF-R1β-hMp1 or FGF-R4α-hMp1 constructs are maintained in a conventional medium for BaF/3 containing 10 μg/ml of blasticidin supplemented either with 10 ng/ml of IL-3 or with 10 ng/ml of FGF2 combined with 100 μg/ml of heparin.

Cell Proliferation Measurement

A confluent culture of BaF/3 cells carrying the chimeric receptors is passaged one-in-three in culture medium supplemented with IL-3 (10 ng/ml) for 24 h. The cells are then deprived of serum overnight in RPMI, before being stimulated. The stimulation is carried out in a 96-well plate (krystal microplate, Porvair) and in quadruplicate. For each condition, the following are added in this order: 50 μl of a solution of two-times concentrated product in RPMI and 50 μl of a cell suspension at 200 000 cells/ml in RPMI containing 0.2% of FCS, 2×NEAA, 2× NaPyr and 2× glutamine. The plates are incubated for 28 h at 37° C. and then 100 μl of Cell Titer Glo (Promega) are added and the amount of ATP is quantified using a luminometer (Luminoskan Ascent, Labsystems).

The compounds that are subjects of the invention are FGF receptor agonists. In particular, they exhibit, in vitro, a specific activity towards FGFR1β and FGFR4α of between $3×10^{-5}$ and $1×10^{-6}$M. By way of example, compounds 44 and 31 are active at a concentration of 30 μM on the Baf/3-FGFR1β and FGF-R4α.

In vitro Angiogenesis Model

The products are tested in terms of inducing the rearrangement of human vein endothelial cells (HUVECs) on matrigel (Becton dickinson 356230) diluted in collagen (rat tail collagen, type I: Becton dickinson 354236). After 24 hours, the cells are observed under the microscope with a X4 objective and the length of the pseudotubules is measured by means of an image analyser (BIOCOM-Visiolab 2000 software).

For the in vitro angiogenesis test, the compounds of the invention demonstrated a specific activity between $10^{-6}$M and $10^{-12}$M. By way of example, compounds 2, 8 and 50 are active at a concentration of 10 nM on the in vitro angiogenesis model.

Model of Post-Ischaemic Leg Revascularization in Mice

The experiment is carried out on C57 mice (IFFA CREDO France).

The animals are anaesthetized by intraperitonal injection, in a volume of 10 ml/kg, of a solution of 50 mg/kg ketamine (Ketamine 1000 Virbac®, Virbac Carros France) and 10 mg/kg xylazine (Rompun 2%®, Bayer Pharma Puteaux France). The animal is placed so that it is lying on its back, and after shaving and disinfection of the skin by painting with Vetedine® solution (Vetoquinol S.A. Lure France), an incision is made in the inguinal region. The femoral artery is excized, the collateral arteries are cauterized and the external and circumflex iliac arteries are ligatured. The skin is sutured with separate stitches using non-resorbable thread. The animals are placed in the recovery room, the temperature of which is regulated at 25° C., until they are completely awake.

The distal perfusion is measured using a laser Doppler scanner (LDPI Lisca Perimed model PIM II, AB Sweden). This technique makes it possible to measure the cutaneous perfusion of the upper part of the back legs. These measurements are carried out under anaesthesia (ketamine+xylazine), immediately before the surgical induction of ischaemia (T0) and immediately after (T1) in order to verify the severity of the ischaemia. Measurements are carried out successively on the healthy leg and on the leg rendered ischaemic in order to establish a perfusion deficit expressed as %. Measurements, carried out under the same conditions of anaesthesia, are taken 3, 7 and 14 days after the induction of ischaemia in order to evaluate the post-ischaemic perfusion recovery.

In this experiment, the compounds of the invention are active at doses of 1 to 50 mg/kg/day. By way of example, compound 21 has a significant activity at a dose of 30 mg/kg/day administered subcutaneously for 7 days, in the ischaemic leg model.

The invention claimed is:

1. An FGF receptor agonist compound corresponding to the formula:

$$M_1\text{-L-}M_2$$

in which $M_1$ and $M_2$, which may be identical or different, are each, independently of one another, a monomer unit corresponding to the following formula M:

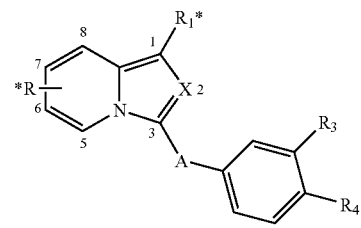

wherein L is a linker group that links $M_1$ and $M_2$ covalently, and L is selected from a linear or branched alkylene radical containing from 2 to 25 carbon atoms, or L is selected from any of the following linker structures:

(A)

(B)

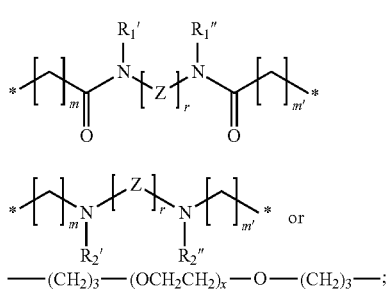

-(CH$_2$)$_3$—(OCH$_2$CH$_2$)$_x$—O—(CH$_2$)$_3$—;

wherein:
x is an integer from 2 to 4;
n is an integer from 1 to 7;
p is an integer from 0 to 11;
r is an integer from 1 to 11;
m and m' are identical or different and are an integer from 0 to 8;
$R_1'$ and $R_1''$, which may be identical or different, are selected from hydrogen atom and linear or branched alkyl radical containing from 1 to 5 carbon atoms;
$R_2'$ and $R_2''$, which may be identical or different, are selected from hydrogen atom, linear or branched alkyl radical containing from 1 to 5 carbon atoms, benzyl radical, and sulfate group, and
Z is a linear alkylene radical containing from 1 to 6 carbon atoms;
X is N or C—$R_2$*, A is a —CO— radical,
* indicates the linkage site of L with, firstly, the monomer unit $M_1$ and, secondly, with the monomer unit $M_2$; said linkage site of each monomer unit $M_1$ or $M_2$ being located on one of the substituents R, $R_1$ or $R_2$;
R is a hydrogen atom, or a radical of formula:

—CO$_2$R$_5$

—CO—NR$_6$R$_7$

—CO—NR$_6$—

—O-Alk

—O-Alk-CO—NR$_6$R$_7$

—O-Alk-CO—NR$_6$—

—O-Alk-NR$_6$R$_7$

—O-Alk-NR$_6$—

8-O* or

6-O*, in which:
$R_5$ is a hydrogen atom, a linear or branched alkyl radical containing from 1 to 5 carbon atoms or a benzyl radical;
$R_6$ and $R_7$, which may be identical or different, are each a hydrogen atom, a linear or branched alkyl radical containing from 1 to 5 carbon atoms or a benzyl radical;
Alk is a linear or branched alkyl radical having from 1 to 5 carbon atoms or a linear or branched alkylene radical having from 1 to 5 carbon atoms;
Ph is a phenyl radical;

$R_1$ is a hydrogen atom or a radical of formula:

—O-Alk

—Ph-3-CO$_2$H 4-pyridine

O*

NH*

—OCH$_2$Ph-3-O*

—OCH$_2$Ph-4-O*

—NHCOPh-3-O*

—NHCOPh-4-O*

—Ph-3-CONH*

NHCO*

—Ph-4-O*or

—Ph-3-O*;

$R_2$ is a linear or branched alkyl radical containing from 1 to 5 carbon atoms or a phenyl radical of the formula CPh-4-O*and CPh-3-O*;

$R_3$ and $R_4$ are, independently of one another, a hydrogen atom, or a radical of formula:

—O-Alk

CO$_2$H or

NH$_2$, in which Alk, $R_5$, $R_6$ and $R_7$ are as defined with respect to the group R;

in the form of a base or an addition salt with an acid or with a base, and/or in the form of a hydrate or a solvate.

2. The compound according to claim 1, comprising the monomer unit of formula M in which:

X=C-R$_2$;

R on the 6-, 7- or 8-position of the indolizine is a hydrogen atom, or a radical of formula:

—CO$_2$R$_5$

—CO—NR$_6$R$_7$

—CO—NR$_6$—

—O-Alk

—O-Alk-NR$_6$R$_7$

—O-Alk-CO-NR$_6$—

—O-Alk-CO-NR$_6$R$_7$

—O-Alk-NR$_6$—

8-O*or

6-O*, in which:
$R_5$ is a hydrogen atom, a linear or branched alkyl radical containing from 1 to 5 carbon atoms or a benzyl radical;

$R_6$ and $R_7$, which may be identical or different, are each a hydrogen atom, a linear or branched alkyl radical containing from 1 to 5 carbon atoms or a benzyl radical;

Alk is a linear or branched alkyl radical containing from 1 to 5 carbon atoms or a linear or branched alkylene radical containing from 1 to 5 carbon atoms;

Ph is a phenyl radical;

$R_1$ is a hydrogen atom or a radical of formula:

—O-Alk

—Ph-3-$CO_2H$ 4-pyridine

O*

NH*

—$OCH_2$Ph-3-O*

—$OCH_2$Ph-4-O*

—NHCOPh-3-O*

—NHCOPh-4-O*

—Ph-3-CONH*

NHCO*

—Ph-4-O* or

—Ph-3-O*;

$R_2$ is a linear or branched alkyl radical containing from 1 to 5 carbon atoms, or a phenyl radical of the formula CPh-4-O* and CPh-3-O*

$R_3$ and $R_4$, which may be identical or different, are each a hydrogen atom, or a radical of formula:

—O-Alk

—$CO_2H$ or $NH_2$, in which Alk is as defined with respect to the group R;

in the form of a base or of an addition salt with an acid or with a base, and also in the form of a hydrate or a solvate.

3. The compound according to claim 1, comprising the monomer unit of formula M in which:

X═C-$R_2$;

R on the 6-, 7- or 8-position of the indolizine is a hydrogen atom, or a radical of formula:

—$CO_2R_5$

—O-Alk

—O-Alk-CO-$NR_6R_7$ or

—O-Alk-$NR_6R_7$, in which:

$R_5$ is a hydrogen atom, a linear or branched alkyl radical containing from 1 to 5 carbon atoms or a benzyl radical;

$R_6$ and $R_7$, which may be identical or different, are each a hydrogen atom, a linear or branched alkyl radical containing from 1 to 5 carbon atoms or a benzyl radical;

Alk is a linear or branched alkyl radical containing from 1 to 5 carbon atoms or a linear or branched alkylene radical containing from 1 to 5 carbon atoms;

Ph is a phenyl radical;

$R_1$ is a halogen atom, or a radical of formula:

—O-Alk

—Ph-3-$CO_2H$ 4-pyridine

O*

NH*

—$OCH_2$Ph-3-O*

—$OCH_2$Ph-4-O*

—NHCOPh-3-O*

—NHCOPh-4-O*

—Ph-3-CONH*

NHCO*

—Ph-4-O* or

—Ph-3-O*;

$R_2$ is a linear or branched alkyl radical containing from 1 to 5 carbon atoms or a phenyl radical of the formula CPh-4-O* and CPh-3-O*;

$R_3$ and $R_4$, which may be identical or different, are each selected from —O-Alk, —$CO_2H$, and $NH_2$, in which Alk is as defined with respect to the group R;

in the form of a base or of an addition salt with an acid or with a base, and also in the form of a hydrate or a solvate.

4. The compound according to claim 3, characterized in that R on the 6- or 8-position of the indolizine is a hydrogen atom;

$R_1$ is a radical of formula:

—O-Alk

—Ph-3-$CO_2H$ 4-pyridine

O*

NH*

—$OCH_2$Ph-3-O*

—$OCH_2$Ph-4-O*

—NHCOPh-3-O*

—NHCOPh-4-O*

—Ph-3-CONH*

NHCO*

—Ph-4-O* or

—Ph-3-O*, in which Alk and Ph, are as defined in claim 3;

$R_2$ is linear or branched alkyl radical containing from 1 to 5 carbon atoms;

$R_3$ is selected from —O-Alk and —$CO_2H$;
$R_4$ is $NH_2$;
in the form of a base or of an addition salt with an acid or with a base, and also in the form of a hydrate or a solvate.

5. The compound according to claim 1, comprising the monomer unit of formula M in which:

X =N;

R on the 5-, 6-, 7- or 8-position of the imidazo[1,5-α]pyridine is a hydrogen atom, or a radical of formula:

—$CO_2R_5$

—CO—$NR_6R_7$

—CO—$NR_6$—

—O-Alk

—O-Alk-CO—$NR_6R_7$

—O-Alk-CO—$NR_6$—

—O-Alk-$NR_6R_7$

—O-Alk-$NR_6$—

8-O* or

6-O*, in which:
$R_5$ is a hydrogen atom, a linear or branched alkyl radical containing from 1 to 5 carbon atoms or a benzyl radical;
$R_6$ and $R_7$, which may be identical or different, are each a hydrogen atom, a linear or branched alkyl radical containing from 1 to 5 carbon atoms or a benzyl radical;
Alk is a linear or branched alkyl radical containing from 1 to 5 carbon atoms or a linear or branched alkylene radical containing from 1 to 5 carbon atoms;
Ph is a phenyl radical;
$R_1$ is a hydrogen atom, or a radical of formula:

—Ph-3-$CO_2H$ 4-pyridine

O*

NH*

—$OCH_2$Ph-3-O*

—$OCH_2$Ph-4-O*

—NHCOPh-3-O*

—NHCOPh-4-O*

—Ph-3-CONH*

NHCO*

—Ph-4-O* or

—Ph-3-O*;

$R_3$ and $R_4$, which may be identical or different, are each a hydrogen atom, or a radical of formula:

—O-Alk $CO_2H$ or $NH_2$;

in the form of a base or of an addition salt with an acid or with a base, and also in the form of a hydrate or a solvate.

6. The compound according to claim 5, comprising the monomer unit of formula M in which:

X =N;

R on the 6-, 7- or 8-position of the imidazo[1,5-α]pyridine is a hydrogen atom, or a radical of formula:

—$CO_2R_5$

—CO—$NR_6R_7$

—CO—$NR_6$—

—O-Alk

8-O* or

6-O*, in which:
$R_5$ is a hydrogen atom, a linear or branched alkyl radical containing from 1 to 5 carbon atoms or a benzyl radical;
$R_6$ and $R_7$, which may be identical or different, are each a hydrogen atom, a linear or branched alkyl radical containing from 1 to 5 carbon atoms or a benzyl radical;
Alk is a linear or branched alkyl radical containing from 1 to 5 carbon atoms or a linear or branched alkylene radical containing from 1 to 5 carbon atoms;
Ph is a phenyl radical;
$R_1$ is a hydrogen atom, or a radical of formula:

—Ph-3-$CO_2H$ 4-pyridine

O*

NH*

—$OCH_2$Ph-3-O*

—$OCH_2$Ph-4-O*

—NHCOPh-3-O*

—NHCOPh-4-O*

—Ph-3-CONH*

NHCO*

—Ph-4-O* or

—Ph-3-O*, $R_3$ and $R_4$, which may be identical or different, are each a radical of the formula:

—O-Alk $CO_2H$, or $NH_2$;

in the form of a base or of an addition salt with an acid or with a base, and also in the form of a hydrate or a solvate.

7. The compound according to claim 6, characterized in that
R on the 8-position of the imidazo[1,5-α]pyridine is a hydrogen atom, or a carboxyl radical of formula —$CO_2R_5$, $R_1$ is a hydrogen atom, or a radical of formula:

—Ph-3-$CO_2$H 4-pyridine

O*

NH*

—$OCH_2$Ph-3-O*

—$OCH_2$Ph-4-O*

—NHCOPh-3-O*

—NHCOPh-4-O*

—Ph-3-CONH*

NHCO*

—Ph-4-O* or

—Ph-3-O*;

$R_3$ is a radical of formula —O-Alk;
$R_4$ is a radical of formula $NH_2$;
in the form of a base or of an addition salt with an acid or with a base, and also in the form of a hydrate or a solvate.

8. The FGF receptor agonist compound according to claim 1, characterized in that $M_1$ is a monomer unit of formula M as defined in claim 1, and $M_2$ is a monomer unit of formula M as defined in claim 5;
in the form of a base or of an addition salt with an acid or with a base, and also in the form of a hydrate or a solvate.

9. The compound according to claim 1, wherein:
L connects the 2 monomer units $M_1$ and $M_2$ by the radical $R_1$ or;
L connects the 2 monomer units $M_1$ and $M_2$ by the radical $R_2$ or;
L connects the 2 monomer units $M_1$ and $M_2$ by the radical R in its 8-position or;
L connects the 2 monomer units $M_1$ and $M_2$ by the radical R in its 7-position or;
L connects the 2 monomer units $M_1$ and $M_2$ by the radical R in its 6-position or;
L connects the 2 monomer units $M_1$ and $M_2$, firstly, by the radical R in its 8-position and, secondly, by the radical R in its 7- or 6-position, or;
L connects the 2 monomer units $M_1$ and $M_2$, firstly, by the radical R in its 7-position and, secondly, by the radical R in its 6-position or;
L connects the 2 monomer units $M_1$ and $M_2$, firstly, by the radical $R_2$ and, secondly, by the radical $R_1$ or;
L connects the 2 monomer units $M_1$ and $M_2$, firstly, by the radical $R_1$ and, secondly, by the radical R in its 8-position;
in the form of a base or of an addition salt with an acid or with a base, and also in the form of a hydrate or a solvate.

10. A pharmaceutical composition containing, as active ingredient, a compound corresponding to the formula $M_1$L-$M_2$ according to claim 1, optionally in combination with one or more inert and suitable excipients.

11. A method for preparing a compound of formula $M_1$-L-$M_2$ according to claim 1, comprising the reaction of at least one monomer unit of formula M-W with a reactant of formula U-L-U', with
M and L being as defined in claim 1,
U and U' being identical or different,
W and U and also W and U' each being a functional group capable of reacting with one another so as to form a covalent bond of C—C, C—O C—N, C—C or C—S type, and
W being located on one of the substituents R, $R_1$ or $R_2$ as defined in claim 1.

12. The method according to claim 11, characterized in that W and U and also W and U' are an amino, hydroxyl, carboxyl, amido, carbamate, halogen, sulphonyl chloride, acid chloride or acid fluoride group, a boronic ester or a boronic acid.

13. The method according to claim 12, comprising the reaction of said monomer units of formula M-W, with R, $R_1$, $R_2$, $R_3$ or $R_4$ being or having a carboxylic acid, and R or $R_1$ being or having an amino group, with a silylation agent and a weak base, followed by an acylation reaction using a diacylating agent and a weak base, and then hydrolysis in an acidic medium.

14. A compound of formula $M_1$-L-$M_2$ as defined in claim 1, selected from:
- disodium salt of 3,3'-{3,6,9,12,15-pentaoxaheptadecane-1,17-diylbis[oxy(l-methoxy-2-methylindolizine -8,3-diyl)carbonyl] }bis(6-aminobenzoic acid);
- disodium salt of 3,3'-(3,6,9,12,15-pentaoxaheptadecane-1,17-diylbis{oxy[3-(4-amino-3-methoxybenzoyl) imidazo[1,5-α]pyridine-8, 1-diyl]})dibenzoic acid;
- disodium salt of 3,3'-{3,6,9,12,15,1 8-hexaoxaicosane-1,20-diylbis[oxy(l-methoxy-2-methylindolizine -6,3-diyl)carbonyl]}bis(6-aminobenzoic acid);
- disodium salt of 3,3'-{3,6,9,12,15-pentaoxaheptadecane-1,17-diylbis[oxy(l-methoxy-2-methylindolizine -6,3-diyl)carbonyl]}bis(6-aminobenzoic acid);
- disodium salt of 3,3'-{3,6,9,12,15,1 8-hexaoxaicosane-1,20-diylbis[oxy(2-methylindolizine -1 ,3-diyl)carbonyl]}bis(6-aminobenzoic acid);
- disodium salt of 3,3'-{ ethane- 1,2-diylbis[oxyethane-2, l-diyloxy-3, 1-phenylenemethyleneoxy (2-methylindolizine-1,3-diyl)carbonyl]}bis(6-aminobenzoic acid);
- disodium salt of 3,3'-{octane-1,8-diylbis[oxy-3,1-phenylenecarbonylimino(2-methylindolizine -1 ,3-diyl) carbonyl]0 }bis(6-aminobenzoic acid);
- disodium salt of 3,3'-{ethane-1,2-diylbis[oxyethane-2,1-diyloxy-3,1- phenylenecarbonylimino (2-methylindolizine-1,3-diyl)carbonyl]}bis(6-aminobenzoic acid);
- disodium salt of 3,3'-{ (1,4-dioxobutane-1,4-diyl)bis [iminoethane-2, 1-diyloxy-3,1-phenylenecarbonylimino (2-methylindolizine-1,3-diyl)carbonyl]}bis(6-aminobenzoic acid);
- disodium salt of 3,3'-{ carbonyl bis[iminoethane-2,1-diyloxy-3,1-phenylenecarbonylimino (2-methylindolizine-1,3-diyl)carbonyl]}bis(6-aminobenzoic acid);
- disodium salt of 3,3'-{ ethane-1,2-diylbis[imino(2-oxoethane-2, l-diyl)oxy-3, 1-phenylenecarbonylimino (2-methylindolizine-1,3-diyl)carbonyl] }bis(6-aminobenzoic acid);
- disodium salt of 3,3'-{propane-1,3-diylbis[imino(2-oxoethane-2,1-diyl)oxy-3,1-phenylenecarbonylimino (2-methylindolizine-1,3-diyl)carbonyl]}bis(6-aminobenzoic acid);

- disodium salt of 3,3'-{butane-1,4-diylbis[imino(2-oxo-ethane-2,1-diyl)oxy-3,1-phenylenecarbonylimino (2-methylindolizine-1,3-diyl)carbonyl]}bis(6-aminobenzoic acid);
- disodium salt of 3,3'-{ethane-1,2-diylbis[imino(2-oxo-ethane-2,1-diyl)oxy-4,1-phenylenecarbonylimino (2-methylindolizine-1,3-diyl)carbonyl]}bis(6-aminobenzoic acid);
- disodium salt of 3,3'-{ethane-1,2-diylbis[oxyethane-2,1-diyloxy-4,1-phenylenecarbonylimino (2-methylindolizine-1,3-diyl)carbonyl]}bis(6-aminobenzoic acid);
- disodium salt of 3,3'-{oxybis[ethane-2,1-diyloxyethane-2,1-diyloxy-4,1-phenylene(2-methylindolizine-1,3-diyl)carbonyl]}bis(6-amino benzoic acid);
- disodium salt of 3,3'-{ethane-1,2-diylbis[oxyethane-2,1-diyloxy-3,1-phenylene(2-methylindolizine-1,3-diyl)carbonyl]bis(6-aminobenzoic acid);
- disodium salt of 3,3'-{oxybis[ethane-2,1-diyloxyethane-2,1-diyloxy-3,1-phenylene(2-methylindolizine-1,3-diyl)carbonyl]}bis(6-aminobenzoic acid);
- disodium salt of 3,3'-{hexane-1,6-diylbis[imino(2-oxo-ethane-2,1-diyl)oxy-3,1-phenylene(2-methylindolizine-1,3-diyl)carbonyl]}bis(6-aminobenzoic acid);
- disodium salt of 3,3'-{hexane-1,6-diylbis[imino(2-oxo-ethane-2,1-diyl)oxy-4,1-phenylene(2-methylindolizine-1,3-diyl)carbonyl]}bis(6-aminobenzoic acid); and
- disodium salt of 2-amino-5-[(1- {[3-(2- {[2-( }[3-({[3 -(4-amino-3-carboxybenzoyl) imidazo[1,5-α]pyridin- 1-yl]amino}carbonyl)phenoxy]acetyl} amino) ethyl]amino} -2-oxoethoxy) benzoyl]amino }-2-methylindolizin-3-yl)carbonyl]dibenzoic acid.

15. The compound according to claim 1, wherein:

X is selected from CCH$_3$, N, CPh-4-O*, and CPh-3-O*;

R is selected from 8-O*, 6-O*, H, 7-CONH*, 7—CO$_2$H, and 6-OCH$_2$CH$_2$NH*;

R$_1$ is selected from OCH$_3$, -Ph-3-CO$_2$H, 4-pyridine, H, O*, —NH*, —OCH$_2$Ph-3-O*, —OCH$_2$Ph-4-O*,-NH-COPh-3-O*, -NHCOPh-4-O*,-Ph-3-CONH*, —NHCO*, -Ph-4-O* and-Ph-3-O*;

R$_3$ is selected from CO$_2$H and OCH$_3$; and

R$_4$ is selected from NH$_2$ or H.

\* \* \* \* \*

UNITED STATES PATENT AND TRADEMARK OFFICE
CERTIFICATE OF CORRECTION

PATENT NO. : 9,120,819 B2  
APPLICATION NO. : 12/171373  
DATED : September 1, 2015  
INVENTOR(S) : Bono et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 803 days.

Signed and Sealed this
Twenty-second Day of March, 2016

Michelle K. Lee
*Director of the United States Patent and Trademark Office*

UNITED STATES PATENT AND TRADEMARK OFFICE
CERTIFICATE OF CORRECTION

PATENT NO. : 9,120,819 B2
APPLICATION NO. : 12/171373
DATED : September 1, 2015
INVENTOR(S) : Francoise Bono et al.

It is certified that error appears in the above-identified patent and that said Letters Patent is hereby corrected as shown below:

Title Page:

In item (56), lines 17-20, please replace: "Rotaru, et al., Synthesis of New Non-Symmetrical Substituted 7,7'-Bisindolizines by the Direct Reaction of 4,4'-Bipyridinium-Ylides with Dimeethyl Acetylenedicarboxylate, J. Hetero. Chem., 41,; 2004; pp. 893-897." with
--Rotaru, et al., Synthesis of New Non-Symmetrical Substituted 7,7'-Bisindolizines by the Direct Reaction of 4,4'-Bipyridinium-Ylides with Dimethyl Acetylenedicarboxylate, J. Hetero. Chem., 41; 2004; pp.893-897.--.

In the Claims:
At column 129, claim number 1, line 41, please replace:
"—CO—NR$_6$—" with -- —CO—NR$_6$— --;

At column 130, claim number 1, lines 26-27, please replace:
"of the formula CPh-4-O*and CPh-3-O*;" with --of the formula CPh-4-O* or CPh-3-O*;--;

At column 130, claim number 2, lines 41-44, please replace:
"monomer unit of formula M in which:
X=C-R$_2$;
R on the 6-, 7- o r 8-position of the indolizine is a hydrogen"
with
--monomer unit of formula M in which:
X = C-R$_2$;

Signed and Sealed this
Second Day of August, 2016

Michelle K. Lee
*Director of the United States Patent and Trademark Office*

CERTIFICATE OF CORRECTION (continued)
U.S. Pat. No. 9,120,819 B2

R on the 6-, 7- or 8-position of the indolizine is a hydrogen--;

At column 130, claim number 2, line 61, please replace:
"8-O*or" with --8-O* or--;

At column 131, claim number 2, line 30, please replace:
"—Ph-4-O*or" with -- —Ph-4-O* or--;

At column 131, claim number 2, line 32, please replace:
"—Ph-3-O*" with -- —Ph-3-O*;--;

At column 131, claim number 2, lines 34-35, please replace:
"of the formula CPh-4-O*and CPh-3-O*" with --of the formula CPh-4-O* or CPh-3-O*;--;

At column 131, claim number 3, lines 48-51, please replace:
    "monomer unit of formula M in which:

$$X = C\text{-}R_2;$$

R on the 6-, 7- or 8-position of the indolizine is a hydrogen" with
--monomer unit of formula M in which:

$$X = C\text{-}R_2;$$

R on the 6-, 7- or 8-position of the indolizine is a hydrogen--;

At column 132, claim number 3, lines 30-31, please replace:
"of the formula CPh-4-O*and CPh-3-O*;" with --of the formula CPh-4-O* or CPh-3-O;*--;

At column 132, claim number 4, line 62: please replace:
"—Ph-4-O*or" with -- —Ph-4-O* or--;

At column 133, claim number 5, lines 6-9, please replace:
    "monomer unit of formula M in which:

$$X = N;$$

R on the 5-, 6-, 7- or 8-position of the imidazo[1,5-α]"
with
    --monomer unit of formula M in which:

R on the 5-, 6-, 7- or 8-position of the imidazo[1,5-*a*]--;

At column 133, claim number 5, line 59, please replace:
"—Ph-4-O*or" with -- —Ph-4-O* or--;

At column 134, claim number 6, lines 4-7, please replace:
"monomer unit of formula M in which:
X =N;
R on the 6-, 7- or 8-position of the imidazo[1,5-α]pyridine" with
--monomer unit of formula M in which:
X = N;
R on the 6-, 7- or 8-position of the imidazo[1,5-*a*]pyridine--;

At column 134, claim number 6, line 18, please replace:
"8-O*or" with --8-O* or--;

At column 134, claim number 6, line 54, please replace:
"—Ph-4-O*or" with -- —Ph-4-O* or--;

At column 135, claim number 7, line 3-5, please replace:
"R on the 8-position of the imidazo[1,5-α]pyridine is a
hydrogen atom, or a carboxyl radical of formula —$CO_2$
$R_5$, $R_1$ is a hydrogen atom, or a radical of formula:" with
--R on the 8-position of the imidazo[1,5-*a*]pyridine is a
hydrogen atom, or a carboxyl radical of formula —$CO_2R_5$;
$R_1$ is a hydrogen atom, or a radical of formula:--;

At column 135, claim number 7, line 27, please replace:
"—Ph-4-O*or" with -- —Ph-4-O* or--;

At column 135, claim number 10, lines 65-66, please replace:
"$M_1L-M_2$" with --$M_1$-L-$M_2$--;

At column 136, claim number 14, lines 27-29, please replace:

"disodium salt of 3,3'-{3,6,9,12,15-pentaoxaheptadecane-1,17-diylbis[oxy(1-methoxy-2-methylindolizine -8,3-diyl)carbonyl] }bis(6-aminobenzoic acid);" with --disodium salt of 3,3'-{3,6,9,12,15-pentaoxaheptadecane-1,17-diylbis[oxy(1-methoxy-2-methylindolizine-8,3-diyl)carbonyl]}bis(6-aminobenzoic acid);--;

At column 136, claim number 14, lines 30-33: please replace:

"disodium salt of 3,3'-(3,6,9,12,15-pentaoxaheptadecane-1,17-diylbis{oxy[3-(4-amino-3-methoxybenzoyl) imi-dazo[1,5-α]pyridine-8, 1-diyl]})dibenzoic acid;" with --disodium salt of 3,3'-(3,6,9,12,15-pentaoxaheptadecane-1,17-diylbis{oxy[3-(4-amino-3-methoxybenzoyl)imi-dazo[1,5-*a*]pyridine-8,1-diyl]})dibenzoic acid;--;

At column 136, claim number 14, lines 34-36: please replace:

"disodium salt of 3,3'-{3,6,9,12,15,1 8-hexaoxaicosane-1,20-diylbis[oxy(1-methoxy-2-methylindolizine -6,3-diyl)carbonyl]}bis(6-aminobenzoic acid);" with --disodium salt of 3,3'-{3,6,9,12,15,18-hexaoxaicosane-1,20-diylbis[oxy(1-methoxy-2-methylindolizine-6,3-diyl)carbonyl]}bis(6-aminobenzoic acid);--;

At column 136, claim number 14, lines 37-39, please replace:

"disodium salt of 3,3'-{3,6,9,12,15-pentaoxaheptadecane-1,17-diylbis[oxy(1-methoxy-2-methylindolizine -6,3-diyl)carbonyl]}bis(6-aminobenzoic acid);" with --disodium salt of 3,3'-{3,6,9,12,15-pentaoxaheptadecane-1,17-diylbis[oxy(1-methoxy-2-methylindolizine-6,3-diyl)carbonyl]}bis(6-aminobenzoic acid);--;

At column 136, claim number 14, lines 40-42, please replace:

"disodium salt of 3,3'-{3,6,9,12,15,1 8-hexaoxaicosane-1,20-diylbis[oxy(2-methylindolizine -1 ,3-diyl)carbonyl]}bis(6-aminobenzoic acid);" with --disodium salt of 3,3'-{3,6,9,12,15,18-hexaoxaicosane-1,20-diylbis[oxy(2-methylindolizine-1,3-diyl)carbonyl]}bis(6-aminobenzoic acid);--;

At column 136, claim number 14, lines 43-45, please replace:

"disodium salt of 3,3'-{ ethane- 1,2-diylbis[oxyethane-2,1-diyloxy-3, 1-phenylenemethyleneoxy (2-methylin-dolizine-1,3-diyl)carbonyl]}bis(6-aminobenzoic acid);" with --disodium salt of 3,3'-{ethane-1,2-diylbis[oxyethane-2,1-diyloxy-3,1-phenylenemethyleneoxy(2-

At column 136, claim number 14, lines 46-48, please replace:

"disodium salt of 3,3'-{octane-1,8-diylbis[oxy-3,1-phe-nylenecarbonylimino(2-methylindolizine -1 ,3-diyl)carbonyl]0 }bis(6-aminobenzoic acid);" with --disodium salt of 3,3'-{octane-1,8-diylbis[oxy-3,1-phe-nylenecarbonylimino(2-methylindolizine-1,3-diyl)carbonyl]}bis(6-aminobenzoic acid);--;

At column 136, claim number 14, lines 49-51, please replace:

"disodium salt of 3,3'-{ethane-1,2-diylbis[oxyethane-2,1-diyloxy-3,1- phenylenecarbonylimino (2-methylin-dolizine-1,3-diyl)carbonyl]}bis(6-aminobenzoic acid);" with --disodium salt of 3,3'-{ethane-1,2-diylbis[oxyethane-2,1-diyloxy-3,1-phenylenecarbonylimino(2-methylin-dolizine-1,3-diyl)carbonyl]}bis(6-aminobenzoic acid);--;

At column 136, claim number 14, lines 52-56, please replace:

"disodium salt of 3,3'-{ (1,4-dioxobutane-1,4-diyl)bis[iminoethane-2, 1-diyloxy-3,1-phenylenecarbon-ylimino (2-methylindolizine-1,3-diyl)carbonyl]}bis(6-aminobenzoic acid);" with --disodium salt of 3,3'-{(1,4-dioxobutane-1,4-diyl)bis[iminoethane-2,1-diyloxy-3,1-phenylenecarbon-ylimino(2-methylindolizine-1,3-diyl)carbonyl]}bis(6-aminobenzoic acid);--;

At column 136, claim number 14, lines 57-59, please replace:

"disodium salt of 3,3'-{ carbonyl bis[iminoethane-2,1-diyloxy-3,1-phenylenecarbonylimino (2-methylin-dolizine-1,3-diyl)carbonyl]}bis(6-aminobenzoic acid);" with --disodium salt of 3,3'-{carbonylbis[iminoethane-2,1-diyloxy-3,1-phenylenecarbonylimino(2-methylin-dolizine-1,3-diyl)carbonyl]}bis(6-aminobenzoic acid);--;

At column 136, claim number 14, lines 60-63, please replace:

"disodium salt of 3,3'-{ ethane-1,2-diylbis[imino(2-oxoethane-2, 1-diyl)oxy-3, 1-phenylenecarbonylimino(2-methylindolizine-1,3-diyl)carbonyl] }bis(6-ami-nobenzoic acid);" with --disodium salt of 3,3'-{ethane-1,2-diylbis[imino(2-oxoethane-2,1-diyl)oxy-3,1-phenylenecarbonylimino(2-methylindolizine-1,3-diyl)carbonyl]}bis(6-ami-nobenzoic acid);--;

At column 137, claim number 14, lines 1-4, please replace:

"disodium salt of 3,3'-{ butane-1 ,4-diylbis[imino(2-oxo-ethane-2,1-diyl)oxy-3,1-phenylenecarbonylimino(2-methylindolizine-1,3-diyl)carbonyl]}bis(6-ami-nobenzoic acid);" with --disodium salt of 3,3'-{butane-1,4-diylbis[imino(2-oxo-ethane-2,1-diyl)oxy-3,1-

CERTIFICATE OF CORRECTION (continued)
U.S. Pat. No. 9,120,819 B2

At column 137, claim number 14, lines 5-8, please replace:
"disodium salt of 3,3'-{ ethane-1,2-diylbis[imino(2-oxo-ethane-2,1-diyl)oxy-4,1-phenylenecarbonylimino(2-methylindolizine-1,3-diyl)carbonyl]}bis(6-ami-nobenzoic acid);" with
--disodium salt of 3,3'-{ethane-1,2-diylbis[imino(2-oxo-ethane-2,1-diyl)oxy-4,1-phenylenecarbonylimino(2-methylindolizine-1,3-diyl)carbonyl]}bis(6-ami-nobenzoic acid);--;

At column 137, claim number 14, lines 9-11, please replace:
"disodium salt of 3,3'-{ ethane-1,2-diylbis[oxyethane-2,1-diyloxy-4,1-phenylenecarbonylimino (2-methylin-dolizine-1,3-diyl)carbonyl]}bis(6-aminobenzoic acid);" with
--disodium salt of 3,3'-{ethane-1,2-diylbis[oxyethane-2,1-diyloxy-4,1-phenylenecarbonylimino(2-methylin-dolizine-1,3-diyl)carbonyl]}bis(6-aminobenzoic acid);--;

At column 137, claim number 14, lines 13-15, please replace:
"disodium salt of 3,3'-{ oxybis[ethane-2,1-diyloxyethane-2,1-diyloxy-4,1 -phenylene(2-methylindol izine-1,3-diyl)carbonyl]}bis(6-amino benzoic acid);" with
--disodium salt of 3,3'-{oxybis[ethane-2,1-diyloxyethane-2,1-diyloxy-4,1-phenylene(2-methylindolizine-1,3-diyl)carbonyl]}bis(6-aminobenzoic acid);--;

At column 137, claim number 14, lines 16-18, please replace:
"disodium salt of 3,3'-{ ethane-1,2-diylbis[oxyethane-2,1-diyloxy-3,1-phenylene(2-methylindolizine -1,3-diyl)carbonyl]bis(6-aminobenzoic acid);" with
--disodium salt of 3,3'-{ethane-1,2-diylbis[oxyethane-2,1-diyloxy-3,1-phenylene(2-methylindolizine-1,3-diyl)carbonyl]bis(6-aminobenzoic acid);--;

At column 137, claim number 14, lines 19-21, please replace:
"disodium salt of 3,3'-{ oxybis[ethane-2,1-diyloxyethane-2,1-diyloxy-3,1-phenylene(2-methylindolizine -1,3-diyl)carbonyl]}bis(6-aminobenzoic acid);" with
--disodium salt of 3,3'-{oxybis[ethane-2,1-diyloxyethane-2,1-diyloxy-3,1-phenylene(2-methylindolizine-1,3-diyl)carbonyl]}bis(6-aminobenzoic acid);--;

At column 138, claim number 14, lines 1-3, please replace:
"disodium salt of 3,3'-{hexane-1,6-diylbis[imino(2-oxo-ethane-2,1-diyl)oxy-3,1-phenylene(2-methylindoli-zine -1,3-diyl)carbonyl]}bis(6-aminobenzoic acid);" with
--disodium salt of 3,3'-{hexane-1,6-diylbis[imino(2-oxo-ethane-2,1-diyl)oxy-3,1-phenylene(2-

At column 138, claim number 14, lines 7-11, please replace:

"disodium salt of 2-amino-5-[(1- {[3-(2- {[2-( }[3-({[3 -(4-amino-3-carboxybenzoyl) imidazo[1,5-α]pyri-din- 1-yl]amino}carbonyl)phenoxy]acetyl} amino)ethyl]amino} -2-oxoethoxy) benzoyl]amino }-2-meth-ylindolizin-3-yl)carbonyl]dibenzoic acid." with --disodium salt of 2-amino-5-[(1-{ [3-(2-{[2-({[3-({[3-(4-amino-3-carboxybenzoyl)imidazo[1,5-$a$] pyri-din-1-yl]amino}carbonyl)phenoxy]acetyl}amino)ethyl]amino}-2-oxoethoxy)benzoyl]amino}-2-meth-ylindolizin-3-yl)carbonyl]dibenzoic acid.--;

At column 138, claim number 15, lines 15-18, please replace:

"$R_1$ is selected from $OCH_3$, -Ph-3-$CO_2$H, 4-pyridine, H, O*, —NH*, —$OCH_2$Ph-3-O*, —$OCH_2$Ph-4-O*,-NH-COPh-3-O*, -NHCOPh-4-O*,-Ph-3-CONH*, —NHCO*, -Ph-4-O* and-Ph-3-O*;" with --$R_1$ is selected from $OCH_3$, —Ph-3-$CO_2$H, 4-pyridine, H, O*, —NH*, —$OCH_2$Ph-3-O*, —$OCH_2$Ph-4-O*, —NH-COPh-3-O*, —NHCOPh-4-O*, —Ph-3-CONH*, —NHCO*, —Ph-4-O* and —Ph-3-O*;--.